US 9,289,627 B2

(12) United States Patent
Otto

(10) Patent No.: US 9,289,627 B2
(45) Date of Patent: Mar. 22, 2016

(54) SYSTEM AND METHOD FOR ESTIMATING AND MANIPULATING ESTIMATED RADIATION DOSE

(75) Inventor: Karl Otto, Salt Spring Island, CA (US)

(73) Assignee: Varian Medical Systems International AG (CH)

( * ) Notice: Subject to any disclaimer, the term of this patent is extended or adjusted under 35 U.S.C. 154(b) by 42 days.

(21) Appl. No.: 13/806,677

(22) PCT Filed: Jun. 22, 2011

(86) PCT No.: PCT/CA2011/050385
§ 371 (c)(1),
(2), (4) Date: Dec. 21, 2012

(87) PCT Pub. No.: WO2011/160235
PCT Pub. Date: Dec. 29, 2011

(65) Prior Publication Data
US 2013/0102830 A1    Apr. 25, 2013

Related U.S. Application Data

(60) Provisional application No. 61/398,286, filed on Jun. 22, 2010.

(51) Int. Cl.
*A61N 5/10* (2006.01)
*A61N 5/00* (2006.01)
*G01T 1/29* (2006.01)

(52) U.S. Cl.
CPC ............... *A61N 5/1031* (2013.01); *A61N 5/00* (2013.01); *A61N 5/10* (2013.01); *G01T 1/29* (2013.01); *H05K 999/00* (2013.01)

(58) Field of Classification Search
CPC ......... A61N 5/1031; A61N 5/10; A61N 5/00; G01T 1/29
USPC ............................................................ 600/1
See application file for complete search history.

(56) References Cited

U.S. PATENT DOCUMENTS

| | | | |
|---|---|---|---|
| 7,831,289 B2 | 11/2010 | Riker et al. | |
| 2006/0274885 A1* | 12/2006 | Wang et al. | 378/65 |

(Continued)

FOREIGN PATENT DOCUMENTS

| | | |
|---|---|---|
| CN | 101014383 | 8/2007 |
| CN | 101247852 | 8/2008 |

(Continued)

OTHER PUBLICATIONS

Pardo-Montero et al., An approach to multiobjective optimization of rotational therapy, Med. Phys. 36(7), Jul. 2009, 3292-3303.

(Continued)

*Primary Examiner* — Christine H Matthews
*Assistant Examiner* — Joshua D Lannu
(74) *Attorney, Agent, or Firm* — Chernoff Vihauer McClung & Stenzel, LLP

(57) ABSTRACT

Methods are provided for permitting manipulation of an achievable dose distribution estimate deliverable by a radiation delivery apparatus for proposed treatment of a subject. One such method comprises: determining a dose modification voxel for which it is desired to modify the dose value and a corresponding magnitude of desired dose modification; for each of a plurality of beams: (i) characterizing the beam as a two-dimensional array of beamlets, wherein each beamlet is associated with a corresponding intensity value and a ray line representing the projection of the beamlet into space; and (ii) identifying one or more dose-change beamlets which have associated ray lines that intersect the dose modification voxel; modifying the intensity values of at least one of the dose-change beamlets; and updating the achievable dose distribution estimate to account for the modified intensity values of the at least one of the dose-change beamlets.

49 Claims, 27 Drawing Sheets

(56) References Cited

U.S. PATENT DOCUMENTS

| | | | |
|---|---|---|---|
| 2007/0034812 A1* | 2/2007 | Ma et al. | 250/492.21 |
| 2008/0298550 A1* | 12/2008 | Otto | 378/65 |
| 2010/0183121 A1 | 7/2010 | Riker et al. | |
| 2012/0136677 A1 | 5/2012 | Ziegenhein et al. | |

FOREIGN PATENT DOCUMENTS

| CN | 101422640 | 5/2009 |
|---|---|---|
| WO | 2007012185 | 2/2007 |

OTHER PUBLICATIONS

Chanyavanich et al., Knowledge-based IMRT treatment planning for prostate cancer, Med. Phys. 38(5), May 2011, 2515-2522.

Craft et al., Multicriteria VMAT optimization, Med. Phys. 39(2), Feb. 2012, 686-696.

Cotrutz et al., Using voxel-dependent importance factors for interactive DVH-based dose optimization, Phys. Med. Biol., 47 (2002), 1659-1669.

Cotrutz et al., IMRT dose shaping with regionally variable penalty scheme, Med. Phys. 30 (4), Apr. 2003, 544-551.

* cited by examiner

SYSTEM AND METHOD FOR ESTIMATING AND MANIPULATING ESTIMATED RADIATION DOSE

RELATED APPLICATIONS

This application claims priority from, and claims the benefit under 35 USC 119(e) of, U.S. application No. 61/398,286 filed 22 Jun. 2010 which is hereby incorporated herein by reference.

TECHNICAL FIELD

The invention relates to planning and delivery of radiation. Particular embodiments provide methods and systems for planning and delivering does distributions for radiation therapy.

BACKGROUND

Radiation is used in the treatment of cancer as well as some other medical conditions. When radiation interacts with tissue, energy from the radiating particles is transferred and deposited within the tissue. The energy is normally deposited in the vicinity of the transfer. The maximum deposition is normally close to the point of interaction. The energy deposited causes damage to cells that may eventually lead to cell death. The quantity of energy deposited is normally described as radiation dose and has the units of Gray (Gy). 1 Gray is equal to 1 Joule per kilogram of medium. The primary goal of radiation treatment is to eradicate cancerous cells in a subject by depositing sufficient radiation dose.

Radiation dose can damage or kill both cancerous and healthy tissue cells. It is typical that some healthy tissue will receive radiation dose during a radiation treatment. For example, a radiation beam originating from a radiation source and projecting through a subject will deposit radiation dose along its path. Any healthy tissue located within the path will normally receive some radiation dose. Additionally, some radiation dose will typically be deposited outside of the beam path into healthy tissue due to radiation scatter and other radiation transport mechanisms. One of the challenges of radiation therapy is to deposit dose in cancerous tissue while minimizing dose received by healthy tissue. Furthermore, some healthy tissues are more sensitive to radiation dose than others making it more important to avoid radiation dose in those tissues.

Modern radiation delivery systems are capable of delivering complex dose distributions. There is a desire for the radiation therapy clinician to be capable of evaluating, determining and/or optimizing trade-offs between delivering dose to a tumor and minimizing dose delivered to healthy tissue. Current techniques for evaluating these trade-offs (treatment plan optimization, for example) are cumbersome and disconnect the operator from quick and direct manipulation and evaluation of achievable dose distributions. There is a desire for improvement of systems and methods for estimating achievable dose distributions and possibly improving the evaluation of trade-offs between radiation dose to cancerous and healthy tissue.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a method for permitting manipulation of an achievable dose distribution estimate deliverable by a radiation delivery apparatus for proposed treatment of a subject, the achievable dose distribution estimate defined over a three-dimensional range of voxels with a dose value for each voxel. The method comprises: determining a dose modification voxel for which it is desired to modify the dose value and a corresponding magnitude of desired dose modification; for each of a plurality of beams: (i) characterizing the beam as a two-dimensional array of beamlets, wherein each beamlet is associated with a corresponding intensity value and a ray line representing the projection of the beamlet into space; and (ii) identifying one or more dose-change beamlets which have associated ray lines that intersect the dose modification voxel; modifying the intensity values of at least one of the dose-change beamlets; and updating the achievable dose distribution estimate to account for the modified intensity values of the at least one of the dose-change beamlets.

Another aspect of the invention provides a method for permitting manipulation of an achievable dose distribution estimate deliverable by a radiation delivery apparatus for proposed treatment of a subject, the achievable dose distribution estimate defined over a three-dimensional range of voxels with a dose value for each voxel. The method comprises: determining a dose modification voxel for which it is desired to modify the dose value and a corresponding magnitude of desired dose modification; for each of a plurality of beams: (i) characterizing the beam as a two-dimensional array of beamlets, wherein each beamlet is associated with a corresponding intensity value; (ii) associating a ray line with each voxel, the ray line projecting from the voxel and intersecting the two dimensional array of beamlets; and (iii) identifying a dose-change beamlet to be the beamlet intersected by the ray line associated with the dose modification voxel; modifying the intensity values of one or more of the dose-change beamlets; and updating the achievable dose distribution estimate to account for the modified intensity values of the one or more of the dose-change beamlets.

Another aspect of the invention provides a method for estimating a dose distribution over a three-dimensional range of voxels resulting from a beam having a spatially varying two-dimensional intensity distribution characterized by a two-dimensional array of beamlets wherein each beamlet is associated with a corresponding intensity value. The method comprises: associating a ray line with each beamlet, the ray line representing the projection of the beamlet into space; convolving the two-dimensional intensity distribution with a two-dimensional dose estimate kernel to obtain a two-dimensional convolved intensity distribution, the two-dimensional convolved intensity distribution comprising a convolved intensity value for each beamlet; and for each beamlet in the two-dimensional array of beamlets: identifying voxels in the three-dimensional range of voxels that are intersected by the ray line associated with the beamlet; and adding a dose contribution to the intersected voxels, the dose contribution based on the convolved intensity value of the beamlet.

Other aspects of the invention provide systems comprising one or more controllers configured to perform the methods of various embodiments of the invention. Other aspects of the invention provide computer program products carrying instructions embodied in a non-transitory computer-readable medium, the instructions when executed by a suitable processor cause the processor to perform the methods of various embodiments of the invention. Other aspects of the invention provide methods, systems and/or computer program products that use the methods of various embodiments for planning and/or delivery of radiation treatment to subjects.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive. In drawings which illustrate non-limiting embodiments:

FIG. 7A shows an example of an operator communicating a desired dose change directly on a representation (e.g. a graphical representation) of a dose distribution. FIG. 7B shows a cross-section of the updated dose distribution determined in accordance with the method of FIG. 4B as a result of the FIG. 7A desired dose change.

FIG. 9A shows the dose modification voxels determined in accordance with the method of FIG. 4B and corresponding to the FIG. 8A desired dose quality metric change. FIG. 9B shows a cross-section of the updated dose distribution determined in accordance with the method of FIG. 4B as a result of the FIG. 9A desired dose change.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
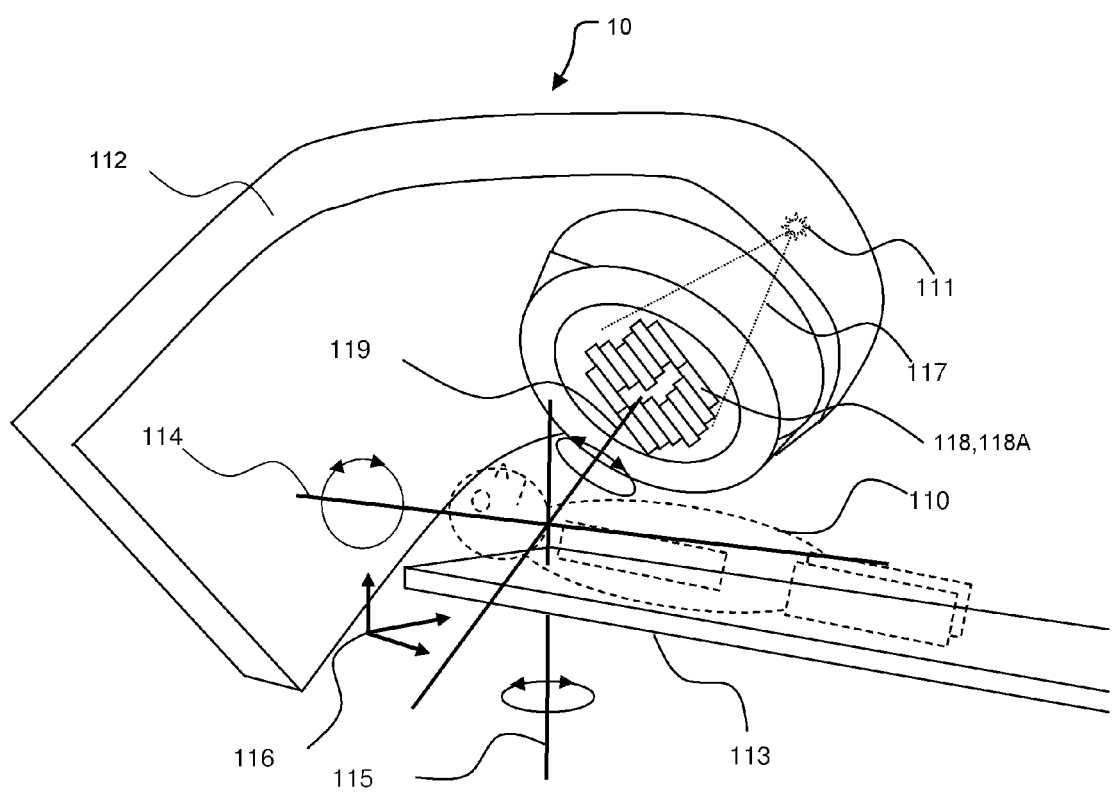
FIG. 1 schematically depicts an example radiation delivery apparatus that may be used in delivering radiation dose to a subject.

FIG. 1 schematically depicts an example radiation delivery apparatus 10 containing a radiation source 111 for delivery of radiation to a subject 110 (e.g. a cancer patient). In some embodiments, radiation source 111 may comprise, or may be generated by, a linear accelerator. In general, radiation source 111 may be generated using any suitable technique. For example, radiation source 111 may comprise decaying matter (e.g. Cobalt-60 or the like) or other types of source(s) which may emit radiation comprising neutrons, electrons, protons, other charged particles and/or the like.

In the exemplary FIG. 1 radiation delivery apparatus 10, radiation source 111 is mounted to a gantry 112 and subject 110 is placed on table 113. Gantry-mounted radiation source 111 and table 113 with subject 110 may rotate and/or translate with respect to each other. For example, gantry 112 may rotate about a longitudinal axis 114 and table 113 holding subject 110 may rotate about a vertical axis 115. Table 113 may also translate relative to gantry 112 and source 111 in one or more of the three dimensions shown by axes 116. Radiation from a radiation source may be emitted in all directions. An enclosure 117 surrounds most of radiation source 111, so that the majority of radiation emitted by source 111 is absorbed within enclosure 117.

Radiation emitted toward subject 110 is permitted to pass through enclosure 117 and through a beam-shaping system 118. Beam-shaping system 118 may comprise one or more collimators which may be used to define a beam of radiation that emanates from radiation source 111 and into subject 110. The collimators of beam-shaping system 118 may be motorized and their position and/or movement may be controlled (e.g. by a suitably configured computer control system or the like). The collimators of beam-shaping system 118 may be controllably configured so that the shape of the radiation beam entering subject 110 preferentially intersects cancerous tissue. In the illustrated example radiation delivery apparatus 10 of FIG. 1, beam-shaping system 118 comprises a multi-leaf collimator (MLC) 118A having a plurality of individually controllable leaves. MLC 118A may also be controllably moved to rotate about beam axis 119.

The FIG. 1 exemplary radiation delivery apparatus 10 can be used to deliver radiation therapy treatment to subject 110. A number of techniques are known for using radiation delivery apparatus 10 in manners which attempt to provide desired dose to diseased tissue (e.g. cancerous tumor) while attempting to minimize the dose to healthy tissue. A first such technique involves moving gantry 112 and/or table 113 to a configuration wherein the radiation beam emitted from source 117 preferentially passes through relatively more diseased tissue and relatively less healthy tissue. This first technique may be improved by treating subject 110 with a first beam at a first configuration of gantry 112 and table 113, moving the gantry 112 and table 113 relative to one another, and then treating subject 110 with a second beam which projects from a different direction than the first beam. Using this two-beam technique, the diseased tissue (tumor) may receive a dose that is a combination of the dose from the two beams, while much of the healthy tissue surrounding the tumor would receive dose from primarily a single one of the beams. This two-beam technique may be extended to multiple (e.g. more than two) beams. Each different relative orientation of gantry 112 and table 113 may correspond to a different beam direction and may be referred to simply as a "beam".

Another example of a technique for using radiation delivery apparatus 10 in a manner which attempts to provide desired dose to a tumor of diseased tissue while minimizing dose to healthy tissue involves collimating each radiation beam (i.e. the beam from each relative configuration of gantry 112 and table 113) so that the projection of the tumor from the view of the radiation source (Beam's eye view) closely approximates the outline of the tumor. In this way dose to healthy tissue surrounding the tumor will be reduced. Collimation system 118 (e.g. MLC 118A) may be used to collimate the individual beams. This collimation technique may be improved by selectively (partially or fully) blocking portions of a radiation beam (from a first direction) that intersect both tumor and sensitive healthy tissue and then compensate for the blocked portion of the tumor by selectively (partially or fully) unblocking portions of one or more radiation beams from one or more other directions. A radiation beam (from a particular direction) comprising spatially non-uniform transmitted portions may be referred to as "Intensity Modulated" in reference to the spatially varying intensity of radiation across the two-dimensional beam projection. Intensity modulation can further improve the difference between dose received by healthy tissue and dose received by tumor, particularly in circumstances where some healthy tissue is of relatively high importance (e.g. healthy organs) and/or is in relatively close proximity to the target tissue and it is desired to impart even less dose to such highly important tissues.

In accordance with other techniques, it may be beneficial to dynamically move one or more components of radiation delivery apparatus 10 during the delivery of radiation. For example, collimation system 118 can change the shape of a radiation beam while source 117 is emitting radiation, thereby providing dynamically varying collimation shapes for intensity modulation. Additionally or alternatively, gantry 112 and table 113 can move relative to one another while source 117 is emitting radiation, thereby providing continuously varying beam directions (in contrast to a finite number of discrete beam directions). Some techniques may involve dynamically varying the position of radiation source 117 through a motion trajectory (e.g. relative movement of gantry 112 and table 113) while simultaneously dynamically varying the collimated beam shape and/or the intensity of radiation source 117.

Figure 2:
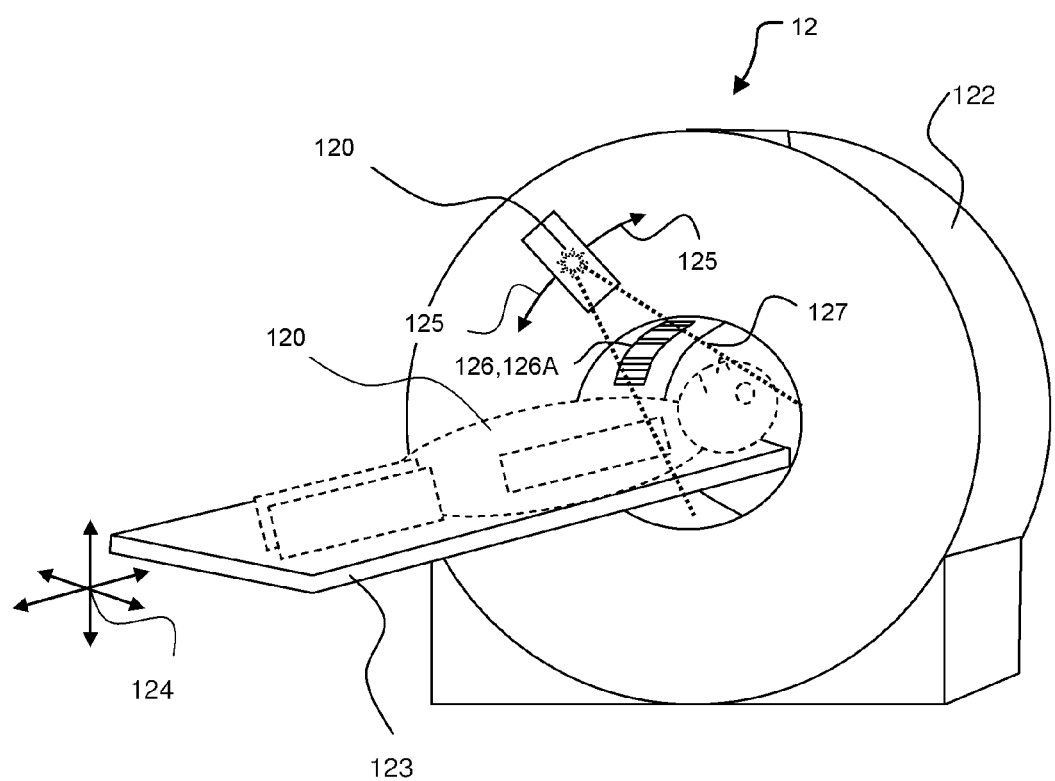
FIG. 2 schematically depicts another example radiation delivery apparatus that may be used in delivering radiation dose to a subject.

Radiation delivery apparatus 10 represents only one example of a radiation delivery apparatus. Other types of radiation delivery apparatus may be used to deliver therapeutic radiation to a subject. A number of non-limiting examples of radiation delivery apparatus include CyberKnife™ (Accuracy Incorporated), Tomotherapy™ (Tomotherapy Incorporated) and Gammaknife™ (Elekta AB). FIG. 2 schematically depicts an example of a Tomotherapy™ radiation delivery apparatus 12. In apparatus 12, radiation source 121 moves in a toroid-shaped gantry 122 about subject 120 who is laying on table 123. Subject 120 and table 123 may be translated relative to gantry 122 (and/or gantry 122 may be translated relative to subject 120 and table 123) in one or more of the directions indicated by axes 124. For example, table 123 may be moved into and out of gantry 122 while radiation source 121 moves in circumferential direction(s) 125 within gantry 122. Radiation emitted by source 121 may project through collimation system 126 (e.g. a MLC 126A or the like). Collimation system 126 may move circumferentially (with source 121) within gantry 122 to create a fan beam 127 impinging on subject 120. As source 121 and collimation system 126 move in circumferential directions 125 around subject 120, table 123 and subject 120 may move relative to gantry 120 and MLC 126A may be configured to provide intensity modulated beams from varying directions around subject 120.

Using radiation delivery apparatus (like exemplary apparatus 10, 12 of FIGS. 1, 2) to deliver therapeutic radiation treatment involves treatment planning. Treatment planning may involve determining the information used to control the radiation delivery apparatus during radiation delivery. Such information may include, by way of non-limiting example, beam configuration parameters (e.g. a number of beams, directions of beams, radiation energy and/or the like) and beam delivery parameters (e.g. collimation shape(s) and corresponding collimation system configuration(s), radiation intensity(s) and/or the like).

Since the size, shape and position of a tumor with respect to the surrounding healthy tissue are different for each subject, a diagnostic imaging procedure is typically used prior to (or as a part of) treatment planning for the purposes of determining the spatial locations of diseased and healthy tissue. Computed Tomography (CT), Magnetic Resonance Imaging (MRI) and Positron Emission Tomography (PET) are common imaging methods used for this diagnostic imaging process. The result of CT, MRI and PET imaging may comprise 3-dimensional images which contain anatomical and functional information. In some embodiments, diagnostic imaging may involve procuring 4-dimensional images, which incorporate time varying image information (e.g. to account for breathing).

The locations of diseased and healthy tissue may be identified on these images prior to (or as a part of) treatment planning. Identification of the locations of diseased and healthy tissue can be performed manually although methods for automatic and semi-automatic identification may also be used. Treatment planning may involve using well known methods to model the radiation dose resulting from a radiation beam. The dose that a subject would receive from a particular radiation beam may be evaluated by overlaying the dose distribution modeled for the particular radiation beam on the subject's images. The dose that a subject would receive from a proposed treatment plan (e.g. a plurality of radiation beams) may be evaluated by superposing dose distributions modeled for the individual beams of the plan and overlaying the superposed dose distribution on the subject's images.

A proposed treatment plan may be characterized or otherwise specified by a set of radiation delivery parameters. As used in this specification and the accompanying claims, radiation delivery parameters may comprise: beam configuration parameters which may relate to the geometric positioning of the radiation source with respect to the subject (e.g. numbers of beams, directions of beams, radiation energy of beams, motion of beams (e.g. for continuously varying beams) and/or the like) and/or beam delivery parameters which may relate to the characteristics of one or more beam configurations (e.g. collimation shape(s) and corresponding collimation system configuration(s), motion of collimation shape(s) and corresponding collimation system configuration(s) (e.g. for continuously varying collimation shapes), radiation intensity(s), and/or the like). By estimating/modeling the dose distributions from multiple different treatment plan proposals (as characterized by multiple corresponding sets of radiation delivery parameters), the multiple different treatment plan proposals can be compared against one another. Once a proposed treatment plan is selected (e.g. because it is determined to be superior to others or is otherwise determined to be satisfactory), the radiation delivery parameters associated with the selected treatment plan may be transferred to the radiation delivery apparatus for delivery of the selected treatment plan to the subject.

Treatment planning for intensity modulated radiation therapy (IMRT) may be more complex because of the permissible spatial variation of intensity distribution across a two-dimensional cross section of each beam or each portion of a beam. Because of the spatial varying intensity distributions of beams associated with IMRT, IMRT treatment planning typically involves dividing each beam into a two-dimensional matrix of spatially varying intensity portions which may be referred to as beamlets. Each beamlet may be effectively treated as a separate beam element that follows a ray line from the source into the subject. In a typical non-limiting IMRT plan, there may be 5 to 9 beams each with a matrix that may comprise more than 100 beamlets.

IMRT planning by a human observer is normally considered impractical due to the large number of beamlets. Several computer algorithms have been developed to determine the spatially varying intensity distributions of each beam in IMRT plans—e.g. the intensities for each of the beamlets in each portion of each beam of the IMRT plan. These algorithms typically involve iterative optimization. For example, at each iteration, a particular set of radiation delivery parameters is proposed, the corresponding dose distribution is calculated (e.g. modeled) and the corresponding dose distribution is evaluated by comparing a quality metric associated with the corresponding dose distribution to some objective. The next iteration may then attempt to propose a set of radiation delivery parameters whose dose distribution is superior to the previous iteration (when evaluated in relation to the same objective). The iterative process normally repeats until an optimization termination criterion is achieved. The iterative optimization process may be relatively time consuming, computationally expensive and/or temporally inefficient, because of the need to model/calculate a dose distribution at each iteration.

Figure 3:
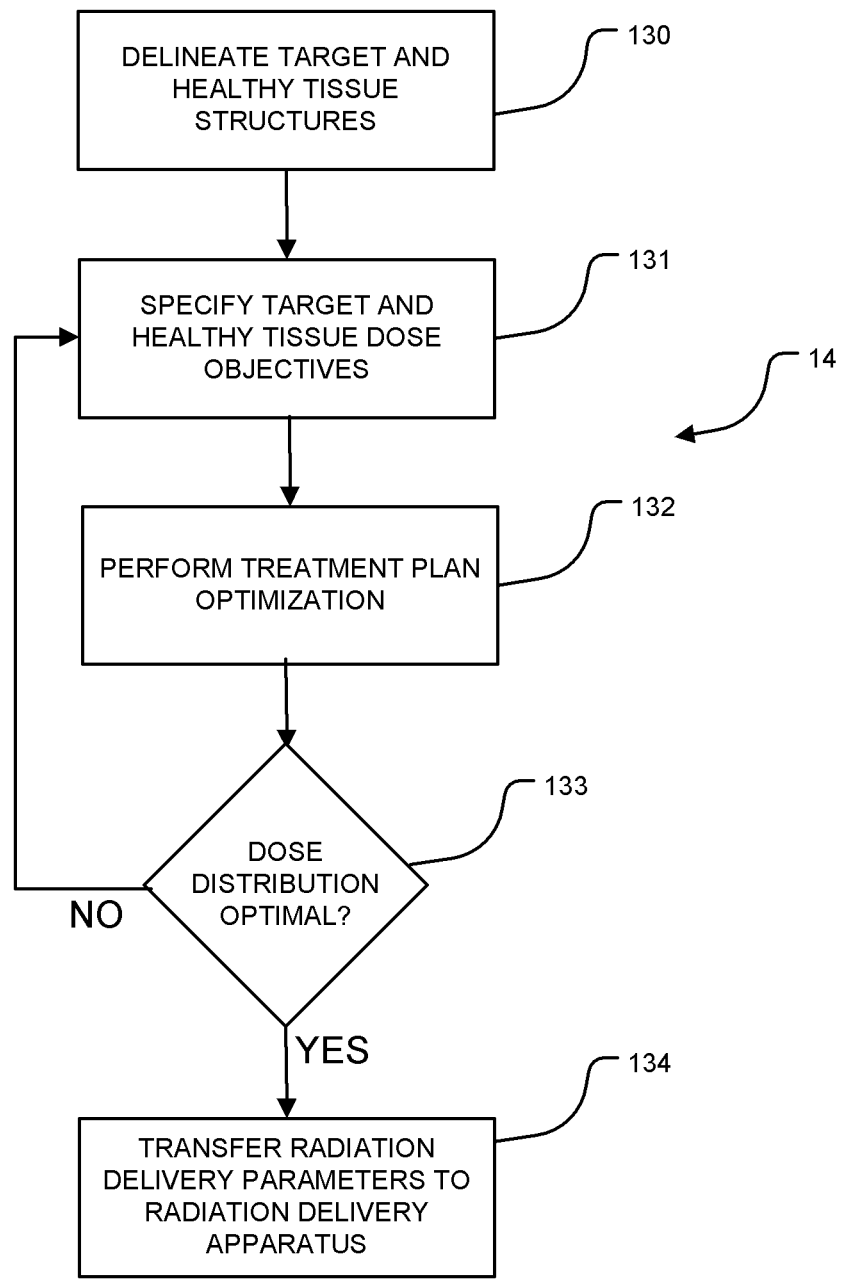
FIG. 3 is a flowchart depicting a method for treatment planning comprising an optimization process which is suitable for use with intensity modulated radiation treatment according to a particular embodiment.

FIG. 3 schematically depicts a method 14 for treatment planning suitable for use with IMRT according to a particular embodiment. Method 14 commences in block 130 which involves delineating target (e.g. diseased) tissue and healthy tissue within the subject using whatever diagnostic image information may be available. In some embodiments, block 130 may involve sub-dividing healthy tissue into one or more levels of relatively important healthy tissue (e.g. organs) and relatively less important healthy tissue. In some embodiments, block 130 may involve acquiring image information from (or through effecting) an imaging procedure. Such image information may be obtained by any suitable technique, including (without limitation): Computed Tomography (CT), Magnetic Resonance Imaging (MRI), Positron Emission Tomography, Ultrasound and/or any other suitable imaging procedure. The image information may be used in block 130 to determine spatial anatomical and functional information regarding diseased and healthy tissue in the subject. This delineation between target and healthy tissues and structure identification may be performed manually, by an operator, and/or using automatic or semi-automatic image segmentation methods.

Block 131 involves specifying dose objectives for target and healthy tissues. Ideally, the dose objectives might be: (i) 100% of the tumor volume receives at least the prescription dose; (ii) 0% of the tumor volume receives dose greater than the prescription dose; and (iii) 0% of the healthy tissue volume receive any dose. Such an ideal objective is not realizable in practice. Instead, achieving a prescription dose to the tumor must be balanced against providing a low dose to healthy tissue structures. Also, there are commonly many healthy tissue structures of concern that vary in importance which can make the number of possible trade-offs cumbersome. By way of non-limiting example: a healthy tissue objective may comprise maximum 20% of the healthy tissue structure volume receives 30% of the dose prescribed to the target; and a target tissue objective may comprise minimum of 90% of the tumor target volume receives 95% of the dose prescribed to the target. Block 131 may also involve specifying a dose quality metric which may be used to evaluate proposed treatment plan iterations against the block 131 dose distribution objectives. Such dose quality metrics may additionally or alternatively be used to indirectly specify dose distribution objectives.

Method 14 then proceeds to block 132 which involves performing an iterative optimization process to arrive at a set of radiation delivery parameters. A typical iterative optimization process which may be implemented as a part of block 132 was discussed above. At the conclusion of the block 132 iterative optimization process, method 14 proceeds to block 133 which involves evaluating the treatment plan (e.g. the calculated/modeled dose distribution) which results from using the radiation delivery parameters output by the block 132 optimization. The block 133 evaluation may be performed by one or more human operators. In some embodiments, however, the block 133 evaluation may be automated. For example, constraints could be developed that specify a minimum number of objectives that must be achieved in order to achieve a positive block 133 evaluation. The number of achieved objectives might be more important for some target structures or for some specified healthy tissue structures. Even in the case of an automated block 133 evaluation, the resulting dose distribution would likely be evaluated by a clinician before actually delivering radiation.

If the block 131 dose distribution objectives are not achievable in practice, then the block 132 optimization may fail to determine an acceptable treatment plan. Conversely, if the block 131 dose distribution objectives are too easily achieved, the treatment plan specified by the block 132 optimization may not achieve the best trade-offs that could be realized in practice. In these circumstances (block 133 NO output path), method 14 may loop back to block 131, where a different optimization may be performed with different dose distribution objectives. Typically, to ensure that the dose distribution achieved in treatment planning method 14 is close to optimal, it is desirable to perform multiple block 132 optimizations with multiple sets of block 131 dose distribution objectives. Once it is determined in block 133 that a particular plan is optimal (block 133 YES output path), then method 14 may proceed to block 134 where the radiation delivery parameters may be transferred to the radiation delivery apparatus for delivery to the subject.

Other methods of providing complex treatment plans and corresponding dose distributions may involve similar iterative optimization. Any combination of radiation delivery parameters may be used in an optimization process for deriving a treatment plan. Such complex treatment plans and corresponding dose distributions may include, by way of non-limiting example, so-called direct aperture optimization techniques, radiation treatment techniques involving dynamic variation of the direction of radiation (e.g. movement of the radiation source during treatment) and/or dynamic variation of collimation shapes and/or intensities within particular beams during treatment and radiation treatment techniques using radiation delivery apparatus such as CyberKnife™ (Accuracy Incorporated), Tomotherapy (Tomotherapy Incorporated) and Gammaknife™ (Elekta AB). The iterative optimizations involved in treatment planning for all of these radiation delivery techniques suffer from similar drawbacks as those discussed above for the iterative optimization associated with IMRT treatment planning. More particularly, such optimizations are time consuming and computationally expensive because of the need for calculating/modeling a dose distribution at each iteration.

One aspect of the invention provides systems and methods for permitting manipulation of achievable dose distribution estimates. In particular embodiments, estimated dose distributions and associated dose quality metrics may be manipulated without the cumbersome and computationally expensive calculations involved in simulating dose for specific radiation delivery parameters (e.g. without the need for iterative optimization). These methods and systems may be simple to use and may permit operator manipulation of estimated dose distributions and associated dose quality metrics. By way of non-limiting example, an operator may select a graphical representation of a dose quality metric using a computer mouse or similar computer pointing device, drag it to the left or right, up or down as desired. As another non-limiting example, an operator may modify a graphical representation of a dose distribution using a computer mouse or similar computer pointing device, to "paint" or "erase" dose from a region of subject anatomy. As these operator-directed manipulations are made, the achievable dose distribution estimate and corresponding dose quality metrics may be updated in near real-time.

The range of physically achievable dose distributions may be limited. Particular embodiments involve the imposition of limits or restrictions on available manipulations, so that the estimated dose distributions (after operator manipulation) are at least approximately achievable. In this way operators are able to rapidly explore trade-offs between dose delivery to target tissues (e.g. tumor(s)) and healthy tissues (e.g. organ(s)) while ensuring that the subject will ultimately receive a dose distribution substantially similar to the estimated one.

Figure 4A:
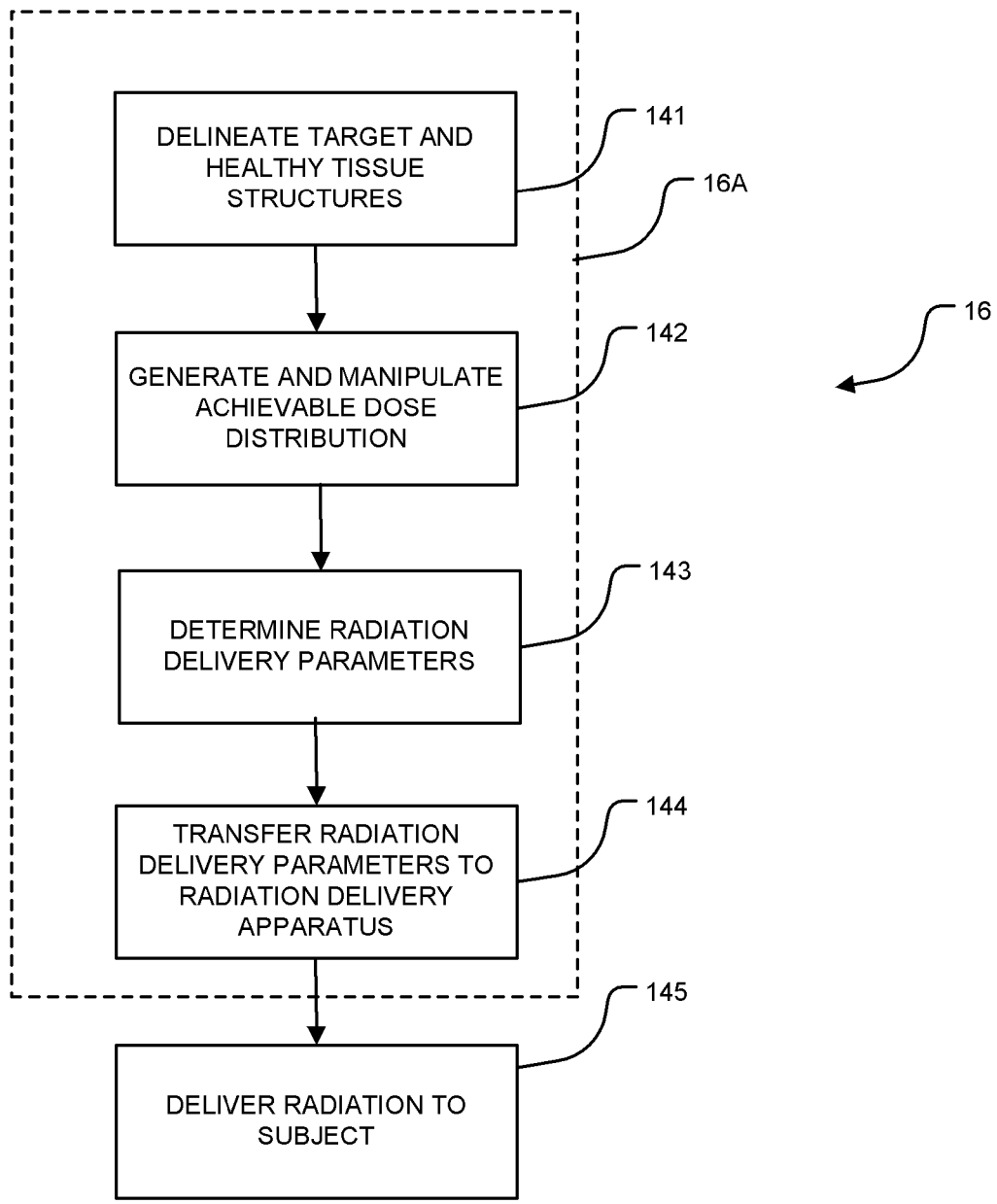
FIG. 4A is a flowchart depicting a method for planning radiation treatment and treating a subject using radiation therapy involving generating, and permitting operator manipulation of, estimated dose distribution according to a particular embodiment of the invention.

FIG. 4A schematically depicts a method 16 for planning radiation treatment and treating a subject using radiation therapy involving manipulation of estimated dose distribution according to a particular embodiment of the invention. Method 16 may generally be divided into two parts: a first part 16A which involves planning the radiation treatment and a second part 145 which involves delivering radiation treatment to the subject. As discussed further herein, planning part 16A may involve determining radiation delivery parameters which may be provided to a radiation delivery apparatus to permit block 145 delivery of radiation in accordance with the plan.

Method 16 commences in block 141 which involves delineating target (e.g. diseased) tissue and healthy tissue within the subject using whatever diagnostic image information may be available. Block 141 may be substantially similar to block 130 described above for method 14 (FIG. 3). Method 16 then proceeds to block 142 which involves generating and permitting operator manipulation of an achievable dose distribution. Operator manipulation of the achievable dose distribution permitted as a part of block 142 may be analyzed directly, effectively in real-time, facilitating a rapid and more comprehensive understanding of the compromises between target tissue dose and healthy tissue dose. Operator manipulation of the achievable dose distribution permitted as a part of block 142 may comprise modification of or additions to target tissue and/or healthy tissue. Block 142 of method 16 is described in more detail below.

At the conclusion of block 142 (e.g. where the operator is satisfied with the manipulated version of the achievable dose distribution or otherwise), method 16 proceeds to optional block 143 which involves determining radiation delivery parameters capable of permitting a radiation delivery apparatus to deliver the estimate of achievable dose as output from block 142. Block 143 may involve performing an iterative optimization process or the like to derive radiation delivery parameters (e.g. beam configuration parameters and/or beam delivery parameters). The block 143 iterative optimization may involve processes similar to those described in blocks 131 and 132 of treatment planning process 14 described above (FIG. 3). The block 143 optimization may also involve an evaluation similar to that of block 133 of treatment planning process 14 described above (FIG. 3). Advantageously, because of the availability of dose distribution manipulation in block 142, it may not be necessary to perform multiple optimizations with different dose distribution objectives as a part of block 143 or fewer optimizations with different dose distributions may be performed as a part of block 143 when compared to the optimization process (blocks 131, 132, 133) of method 14 (FIG. 3)—i.e. the availability of dose distribution manipulation in block 142 of method 16 may reduce or eliminate the need for multiple iterative optimization loops (analogous to loops through blocks 131, 132 and 133 (NO output path) of the method 14 optimization process).

After optimization to obtain the radiation delivery parameters in block 143, method 16 proceeds to block 144 which involves transferring the block 143 radiation delivery parameters to the controller of a radiation delivery apparatus. These radiation delivery parameters may then be used by the controller of the radiation delivery apparatus in block 145 to cause the radiation delivery apparatus to deliver radiation to the subject in accordance with the radiation treatment plan corresponding to the radiation delivery parameters.

Figure 4B:
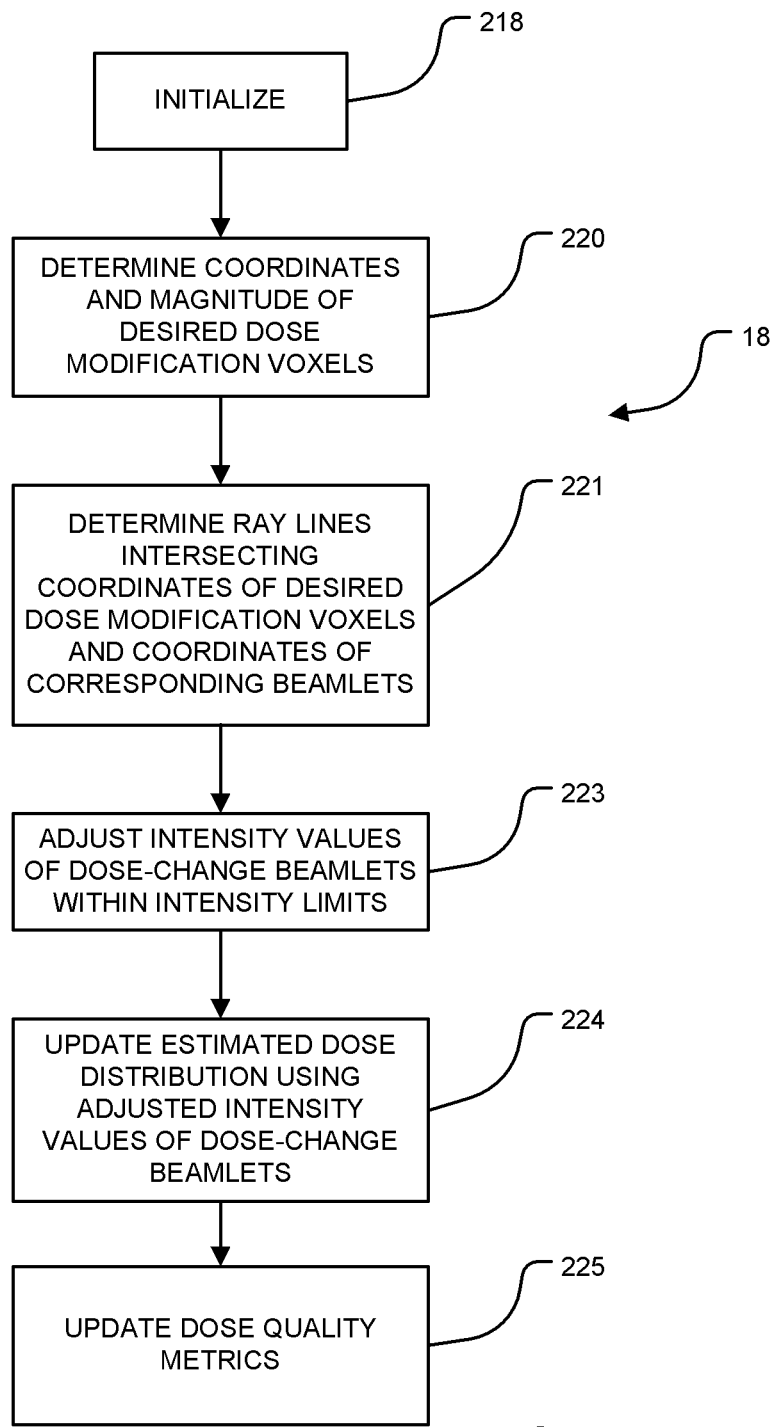
FIG. 4B is a flowchart depicting a method for generating, and permitting operator manipulation of, an estimated dose distribution according to a particular embodiment.

As discussed briefly above, block 142 of radiation treatment method 16 involves generating, and permitting operator manipulation of, an achievable dose distribution. FIG. 4B schematically illustrates a method 18 for generating, and permitting operator manipulation of, an achievable dose distribution according to a particular embodiment. Method 18 of FIG. 4B may be used to implement block 142 of radiation treatment method 16 (FIG. 4A).

Method 18 commences with initialization in block 218. The block 218 initialization may involve: establishing a calculation grid over a region of interest in the delineated image information; defining a configuration of beams; defining an initial intensity distribution of beamlets for each beam; generating an initial estimate of an achievable dose distribution using the beam configuration and beamlet intensity distributions; and, optionally, determining an initial estimate of one or more dose quality metrics based on the initial estimated dose distribution.

Figure 4C:
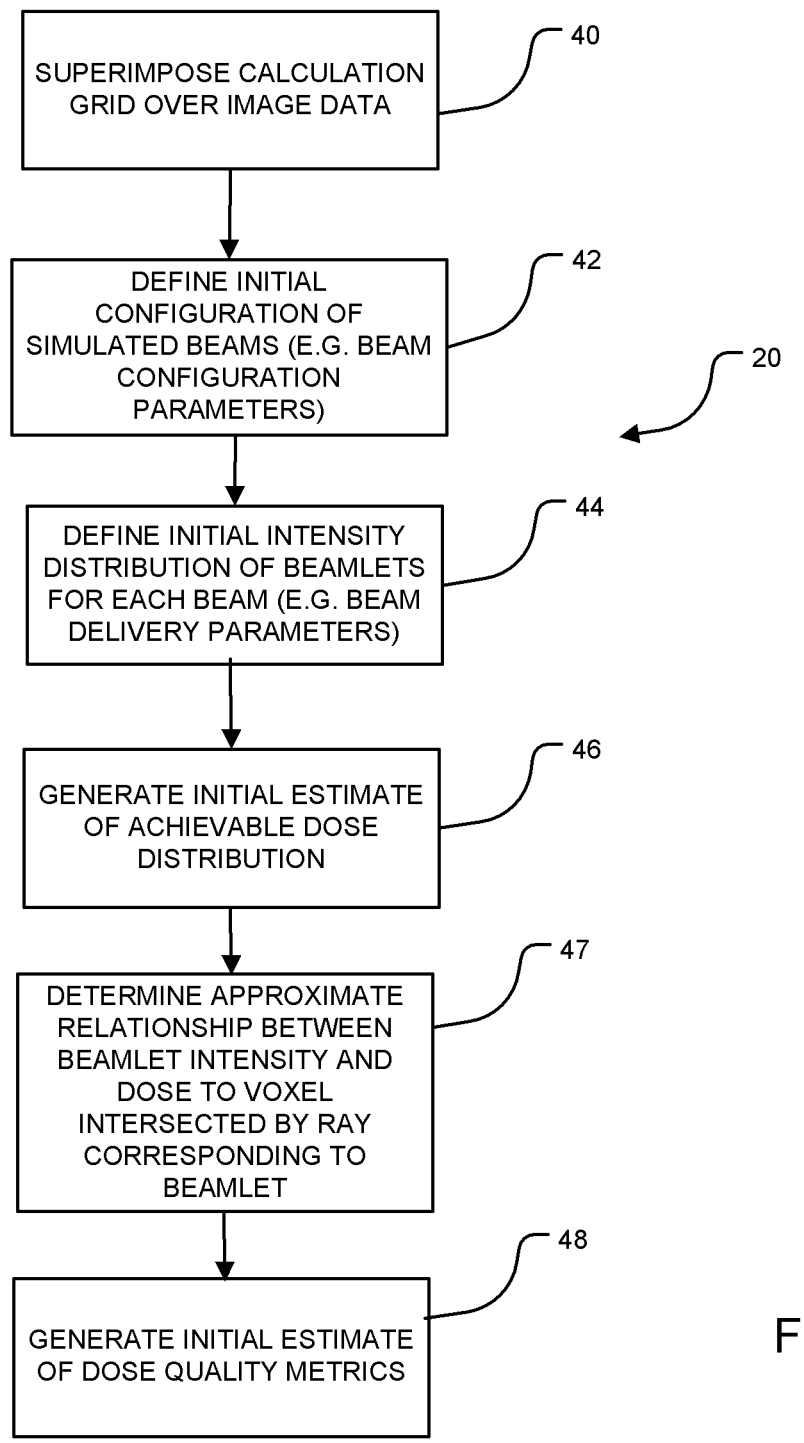
FIG. 4C is a flowchart depicting an initialization method suitable for use in the method of FIG. 4B.

FIG. 4C schematically illustrates an initialization method 20 suitable for use in block 218 of method 18 according to a particular embodiment. Initialization method 20 commences in block 40 which involves creating a calculation grid and superimposing the calculation grid over the delineated image data and segmented healthy and target tissue structures. The delineated image data may be obtained as a part of block 141 (FIG. 4A) discussed above. The superimposed calculation grid may comprise a three-dimensional grid of voxels that spans a region of interest within a subject. The three-dimensional grid of voxels may be characterized by a suitable coordinate system which may permit indexing and/or identifying individual voxels within the grid by their corresponding coordinates.

Figure 5A:
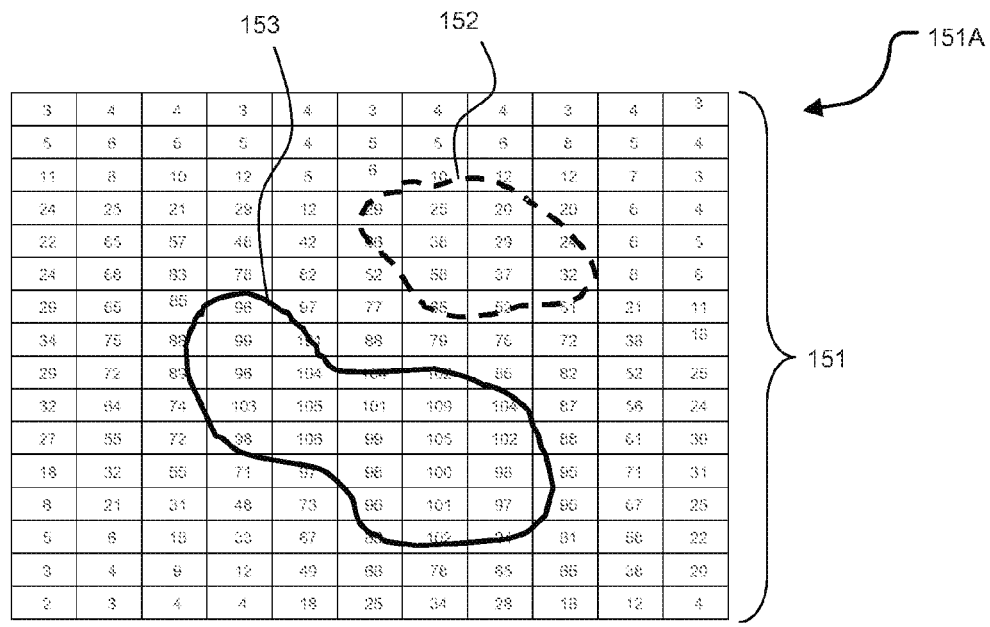
FIG. 5A shows a schematic depiction of a two-dimensional cross section of a calculation grid superimposed on image data which includes exemplary healthy tissue and target structures together with the estimated dose for each voxel in the calculation grid.

FIG. 5A shows a schematic depiction of a two-dimensional cross sectional portion 151 of a three-dimensional calculation grid 151A superimposed on image data comprising exemplary anatomical structures including healthy tissue structure 152 (shown in dashed lines) and target structure 153 (shown in full lines). Only two anatomical tissue structures are shown in the FIG. 5A example. In practice, there may be different numbers of structures (target structures and/or healthy tissue structures) associated with a region of interest in a subject. While the illustrated portion 151 of calculation grid 151A may be referred to as a two-dimensional cross-section, each box of grid portion 151 shown in FIG. 5A actually represents a corresponding voxel in the overall three-dimensional calculation grid 151A for the subject. In this sense, the FIG. 5A grid portion 151 is actually three-dimensional grid portion 151 with a depth of one voxel. As will be explained in more detail below, the numerical values in each voxel of grid portion 151 represent example values of the dose distribution expected to be delivered to these voxels, although these dose distribution estimates will not typically be known when calculation grid is established in block 40.

Returning to FIG. 4C, initialization method 20 proceeds to block 42 which involves defining a configuration of beams. The block 42 initial configuration of beams may comprise defining parameters similar to those beam configuration parameters discussed above—e.g. numbers of beams, directions of beams, radiation energy of beams and/or the like. The block 42 beam configuration may be identified manually or through an independent optimization process. The block 42 beam configuration may comprise one or more static beams, one or more continuously moving beams or a combination of static and moving beams. Continuously moving beams may be characterized by a motion path (trajectory) of the beam direction together with a suitable sampling of multiple stationary beams with positions along the motion path.

Figure 6:
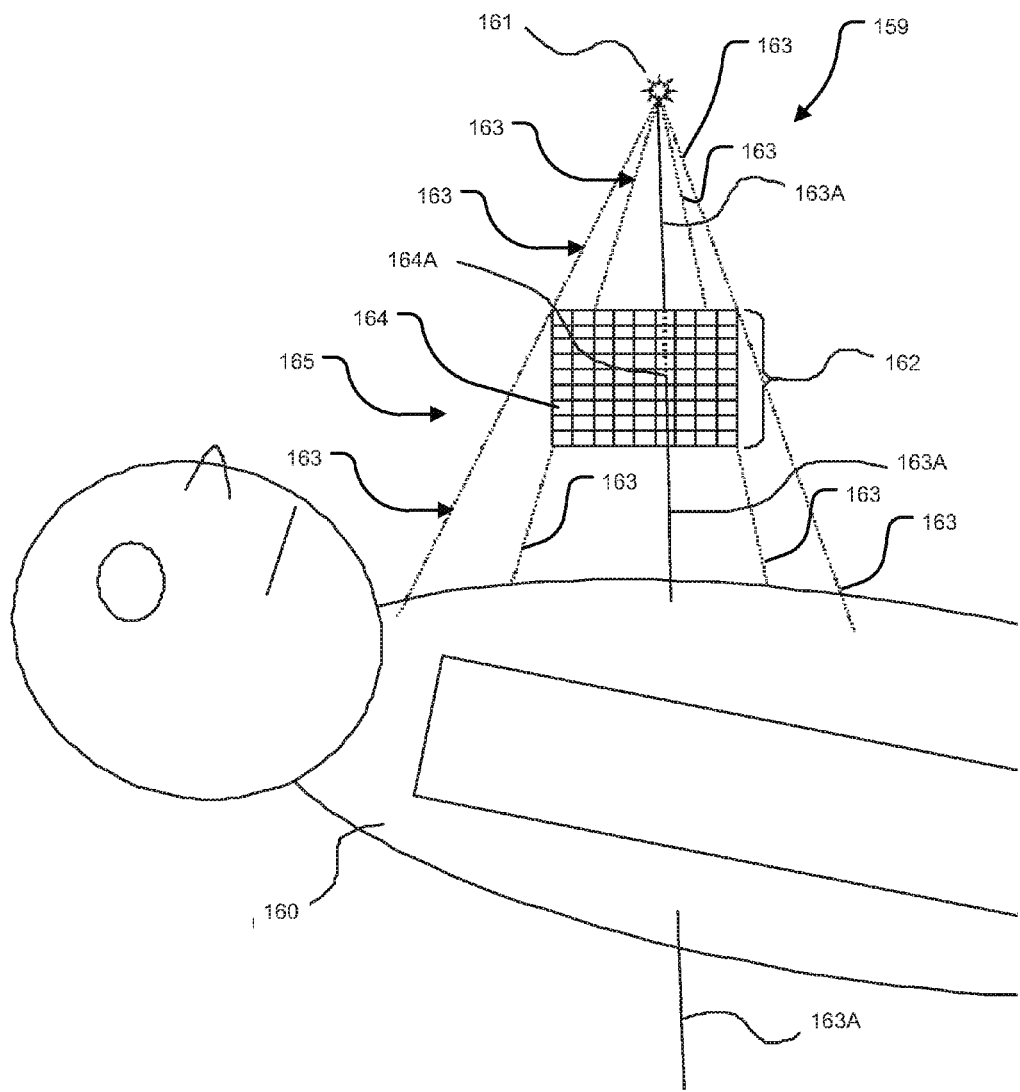
FIG. 6 is an illustration of a beam between a radiation source and subject including associated intensity grid and example ray lines.

Initialization method 20 then proceeds to block 44 which involves defining an initial intensity distribution of beamlets for each of the block 42 beams. Such initial intensity distributions may be similar to initial values for parameters similar to beam delivery parameters discussed above. FIG. 6 schematically depicts a representative beam 159 from the block 42 beam configuration. Beam 159 is directed from a radiation source 161 and delivered toward a subject 160. Each beam in the block 42 beam configuration may be characterized, at least in part, by the position of radiation source 61 with respect to subject 60 (as defined by the block 40 calculation grid and the corresponding image data for subject 60). Each beam 159 is associated with a corresponding intensity distribution 165 which is defined in block 44. In block 44, the intensity distribution 165 corresponding to each beam 159 may be segmented into a two-dimensional grid 162 of intensity beamlets 164. Two dimensional intensity distribution grid 162 may be characterized by a suitable coordinate system which may permit indexing and/or identifying individual beamlets 164 within grid 162 by their corresponding coordinates. Each beamlet 164 may be associated with a corresponding ray line 163 which originates from radiation source 161 and passes through intensity distribution 165 and grid 162 at the location of the beamlet 164. In the FIG. 6 illustration, a particular ray line 163A is shown to correspond with a particular beamlet 164A.

Block 44 also involves assigning initial intensity values to the individual beamlets 164 for each beam 159—i.e. initializing the intensity distribution 165 for each beam 159. The initial intensity distributions 165 may be defined in block 44 using a variety of different techniques. By way of non-limiting example:

Intensity distribution 165 is zero for all beamlets 164 and all beams 159. This initial intensity assignment corresponding to zero dose for all structures.

Intensity distribution 165 is random over each grid 162 of beamlets 164 for each beam 159, intensity of each beamlet 164 is random over all intensity distributions 165 for all beams 159 or some other suitable scheme involving at least some form of random assignment of intensities to corresponding beamlets 162.

Intensity distributions 165 for all or a subset of beams 159 are assigned so that an approximate sphere of dose encompasses target structure(s) 153.

Intensity distributions 165 for all or a subset of beams 159 are assigned such that beamlets 162 corresponding to ray lines 163 that intersect target structure(s) 153 are assigned an initial positive intensity value (e.g. unity) and beamlets 162 are otherwise assigned a different initial value (e.g. zero or some other relatively low value).

Intensity distributions 165 for all or a subset of beams 159 are rescaled (e.g. by an equal amount) so that the resultant estimated dose distribution would have a maximum dose corresponding to some dose threshold (e.g. a dose threshold equal to a highest prescription dose for target structure(s) 153).

Intensity distributions 165 for all or a subset of beams 159 are proportional or correlated with a desired (e.g. prescription) dose for target structure(s) 153.
  Intensity distributions 165 are generated for all or a subset of beams 159 where beamlets 162 corresponding to ray lines 163 that intersect target structure(s) 153 are assigned an intensity value proportional to or correlated with a desired dose for each such target structure 153.
  A margin (e.g. offset) may be added to the intensity distributions 165 (or to individual beamlets 162 corresponding to ray lines 163 that intersect target structure(s) 153) to ensure proper coverage of the target structure(s) 153 by the resulting dose distribution.
  For target structures 153 that overlap in a given beam 159 (e.g. a ray line 163 intersects multiple target structures 153), the intensity of the corresponding beamlet 164 may be assigned an intensity proportional to or correlated with the desired dose for the target structure with the highest desired dose and/or the corresponding beamlet 164 may have its assigned intensity weighted by the target structure 153 that has the highest desired dose.
  For target structures that overlap in a given beam 159, the intensity of the corresponding beamlet 164 may be assigned an intensity proportional to or correlated with the desired dose for the target structure with the lowest desired dose and/or the corresponding beamlet 164 may have its assigned intensity weighted by the target structure 153 that has the lowest desired dose.

Returning to FIG. 4C, after defining intensity distributions 165 in block 44, method 20 proceeds to block 46 which involves generating an initial estimate of the dose distribution based on the block 42 beam configuration and the block 44 intensity distributions. Block 46 may involve known methods of dose estimation, such as by way of non-limiting example, Monte Carlo, collapsed cone convolution, pencil beam, anisotropic analytical algorithm, Boltzman equation solvers and/or the like. The block 46 dose estimation may comprise independently estimating the dose for each beam 159 of the block 42 beam configuration and then adding these dose contributions to arrive at an overall initial dose distribution estimate. The block 46 dose estimation may involve assigning a dose value to each voxel in the block 40 calculation grid 151A. These dose estimate values are represented in FIG. 5A by the numbers in the boxes corresponding to voxels, it being understood that higher numbers correspond generally to higher estimated dose amounts. Initialization method 20 may optionally involve a procedure (in block 47) for establishing an approximate relationship between the intensities of beamlet(s) 164 having ray line(s) 163 that intersect a particular voxel and the corresponding dose delivered to the particular voxel. This block 47 approximate relationship may be determined using one or more suitable calibration procedures, may be determined based on empirical testing and/or data and/or the like. This block 47 relationship is explained in more detail below.

Method 20 may then proceed to block 48 which involves optionally determining one or more initial dose quality metrics based on the block 46 initial dose distribution estimate. Dose quality metrics determined in block 48 may generally comprise any function of the estimated dose distribution. Some dose quality metrics include:
  The average dose to a structure;
  Dose volume histogram(s)—often referred to as DVHs;
  Rate of dose fall-off outside target structure(s) 153;
  Dose conformity indices—e.g. how closely the prescription dose matches the shape of target structure(s) 153);
  Radiobiological objective(s)—e.g. tumor control probability, normal tissue complication probability, equivalent uniform dose, and/or the like.

Figure 5B:
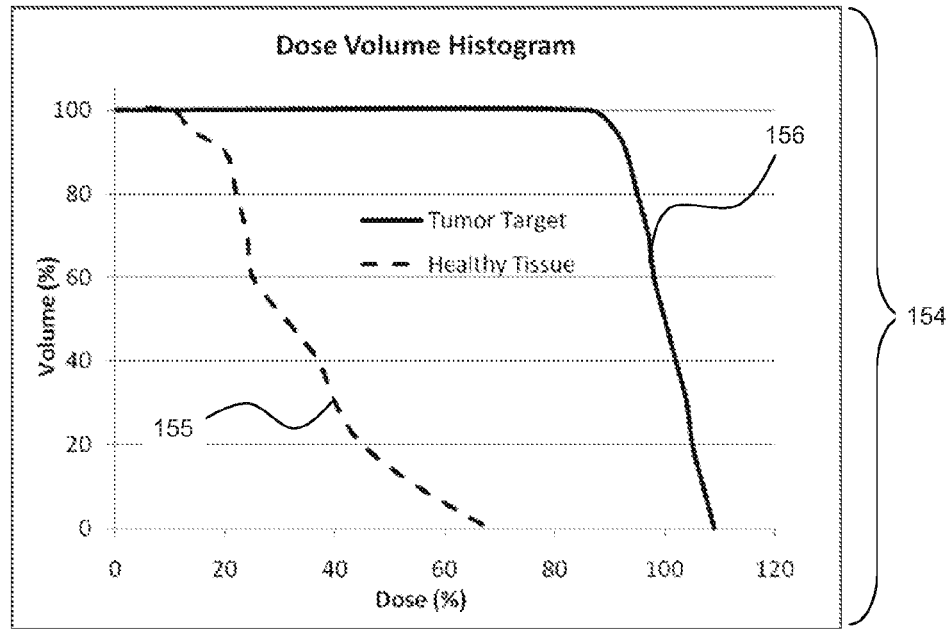
FIG. 5B shows a dose volume histogram (DVH) corresponding to the FIG. 5A dose distribution.

DHVs represent one popular and widely used dose quality metric. A DVH is a graphical plot of structure volume (target tissue or healthy tissue) on the Y-axis versus dose on the X-axis. It is common to use cumulative DVHs (which are typically referred to simply as 'DVHs') when evaluating treatment plans. FIG. 5B shows a plot 154 of two typical DVHs corresponding to the estimated dose distribution shown in the three-dimensional calculation grid 151A for which a cross-sectional portion 151 is shown in FIG. 5A. DVH 156 corresponds to target structure 153 and DVH 155 corresponds to healthy tissue structure 152.

Returning to the FIG. 4B method 18 for generating and permitting manipulation of achievable dose distributions, after completion of the block 218 initialization, method 18 proceeds to block 220 which involves determining the coordinates and estimated magnitude of desired dose modifications. The coordinates determined in block 220 to be associated with desired dose changes may be referred to as the desired dose modification coordinate(s)/voxel(s) and the associated magnitudes may be referred to as the desired dose modification magnitude(s). Block 218 may involve receiving operator input which is indicative of desired dose modifications. By way of non-limiting example, an operator may indicate a desired dose modification (increase or decrease) to a particular dose modification voxel in calculation grid 151A, an operator may communicate a desired modification to a dose quality metric and/or the like. Various embodiments may comprise one or more of a variety of different techniques for receiving such operator input. Such techniques may include (without limitation):
  Keyboard entry (e.g. typing a spatial location (e.g. calculation grid coordinates) of the desired dose modification voxel and the amount of the desired dose modification or typing a desired modification to a dose quality metric).
  Manipulation of graphical representations of dose distributions and/or dose quality metrics via a graphical user interface.
  Specifying a location on a graphical representation of the subject using a mouse or similar computer pointing device and, using a mouse button or keyboard input to indicate whether to increase or decrease the dose at that location and/or to indicate the magnitude of the desired dose modification.

Figures 7A, 7B:
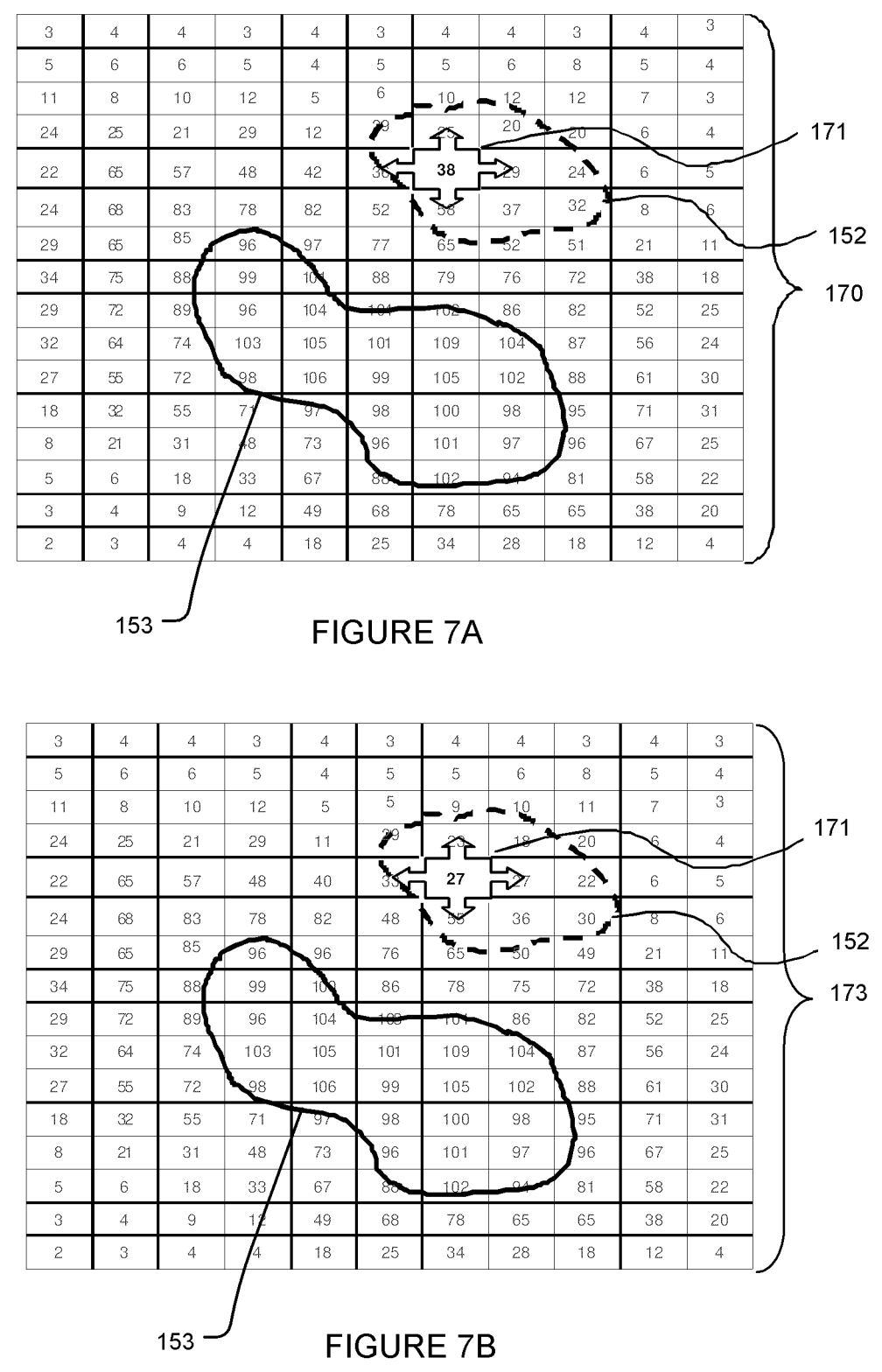

Other computer input devices (trackball, touch screen, voice command, video command and/or the like) may also be used FIG. 7A shows an example of an operator communicating a desired dose modification directly on a representation (e.g. a graphical representation) of a dose distribution 170. In the FIG. 7A example, the operator selects a dose modification location (e.g. dose modification voxel) 171 inside a healthy tissue structure 152 and then communicates a desired dose reduction at that dose modification voxel 171.

Figure 8A:
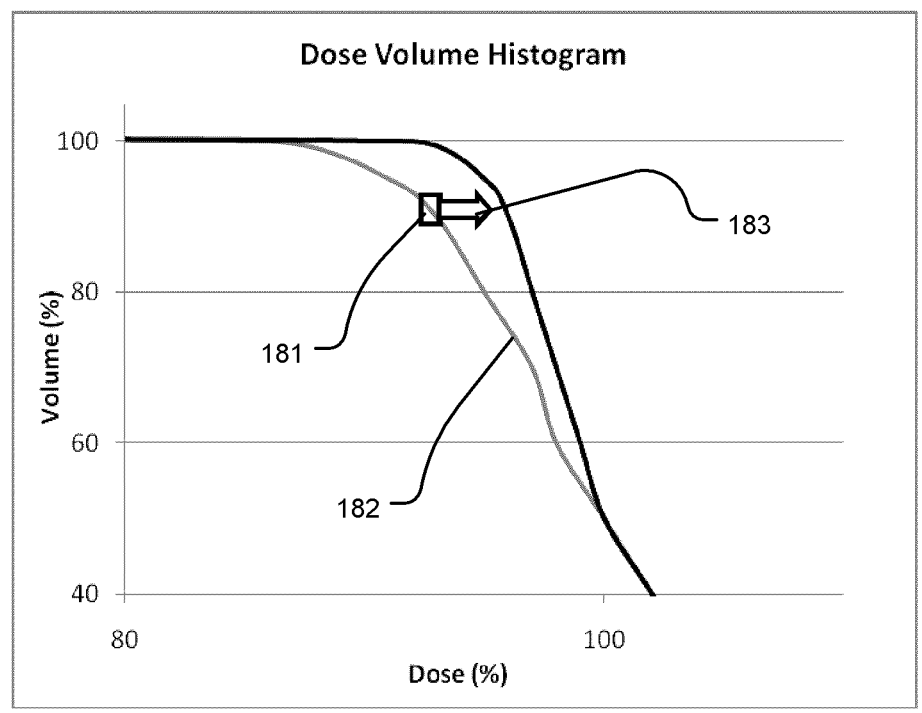
FIG. 8A shows an example of an operator communicating a desired dose quality metric change on a representation (e.g. a graphical representation) of a DVH.

FIG. 8A shows an example of an operator communicating a desired dose modification on a representation (e.g. a graphical representation) of a DVH. In the FIG. 8A example, the operator selects a point 181 on the DVH 182 corresponding to a target structure and indicates that an adjustment corresponding to a higher dose 183. As discussed above, block 220 involves determining coordinates (e.g. voxel locations) and estimated magnitudes of desired dose modifications. Accordingly, block 220 may involve a process for converting the DVH input of FIG. 8A to corresponding dose modification coordinates/voxels and desired dose modification magnitudes. Similarly, block 220 may involve process(es) for converting other input relating to other dose quality metric(s) to corresponding dose modification coordinates/voxels and desired dose modification magnitudes. In particular embodiments, the coordinates and magnitudes of desired dose modifications may be determined in block 220 by processes which comprise:
  inverting the dose quality metric function, so that dose magnitude and dose coordinates become function(s) of the dose quality metric; and
  calculating the required dose distribution modification (magnitude and location) by applying the operator-indicated modifications to the dose quality metric value in the inverted dose metric function.

Figures 9A, 9B:
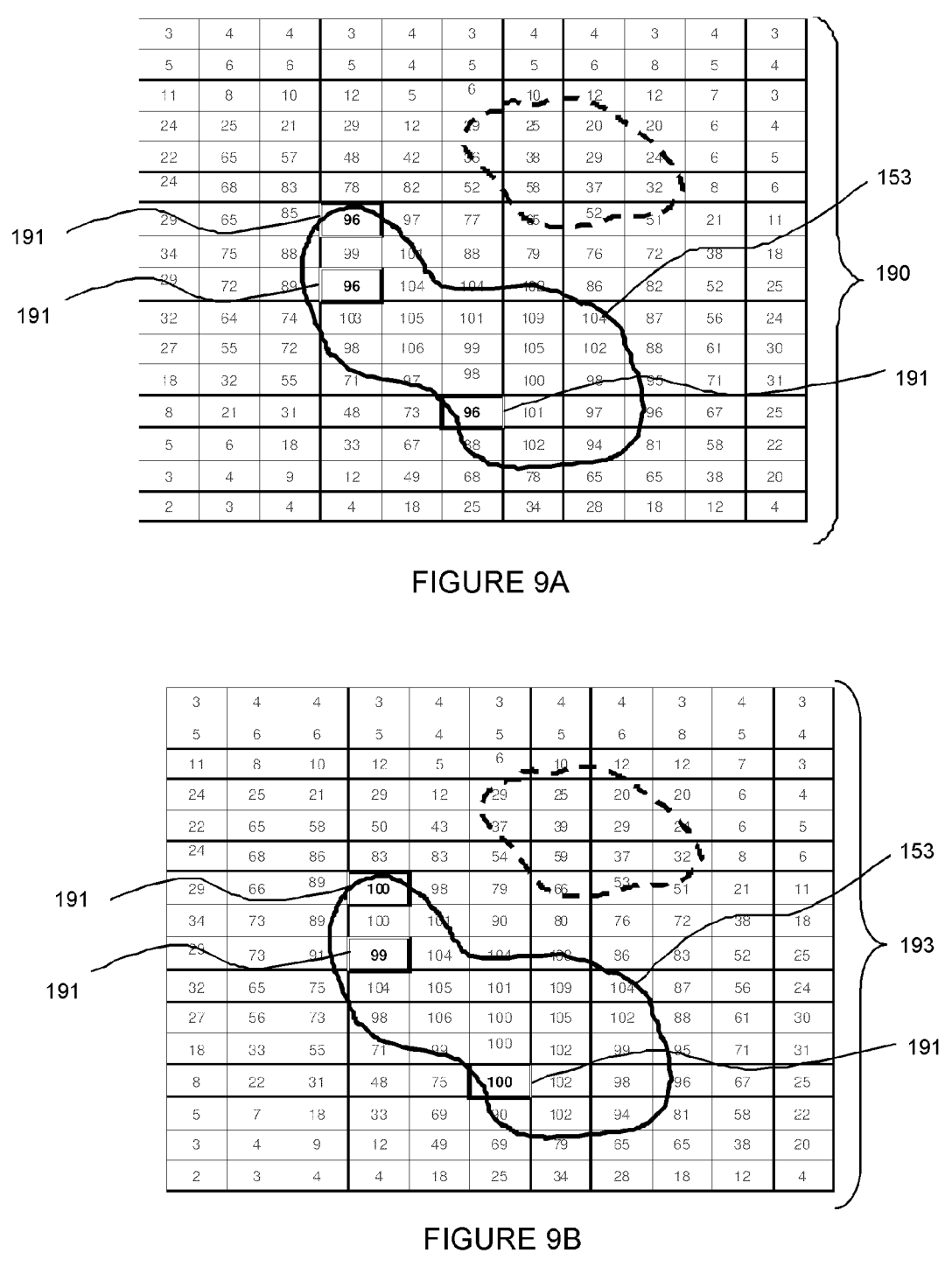

FIG. 9A shows part of the result of this block 220 inversion procedure which includes the dose modification coordinates (e.g. voxel locations) 191 of the dose modifications corresponding to the FIG. 8A operator manipulation of the DVH. In the illustrative example of FIG. 9A, the FIG. 8A DVH manipulation corresponds to desired increases in the dose magnitude of coordinates (voxel locations) 191 inside target structure 153. Although the magnitudes of the corresponding dose modifications are also determined as part of the block 220 inversion procedure, they are not explicitly shown in the schematic depiction of FIG. 9A.

Figure 10:
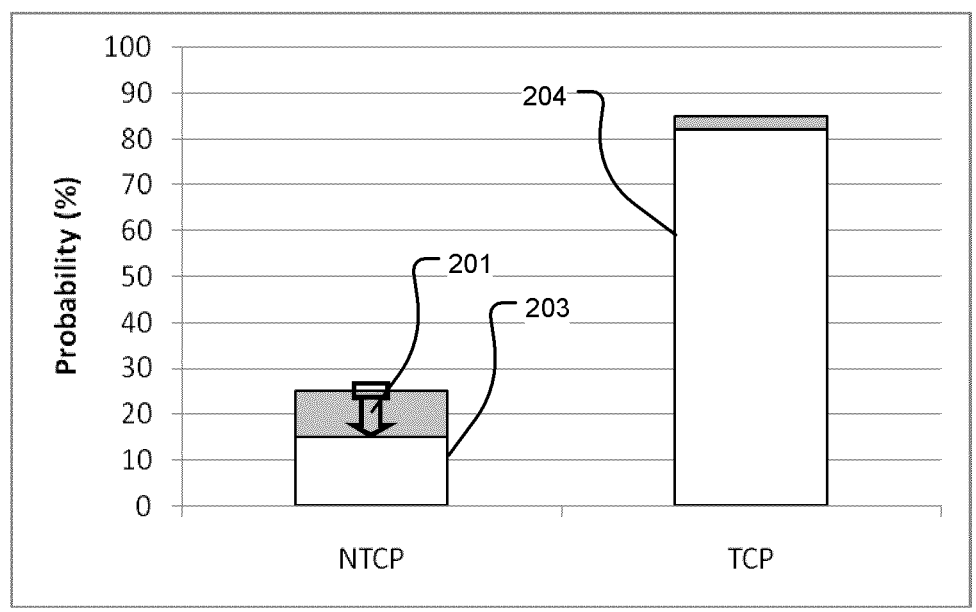
FIG. 10 shows an example of an operator communicating a desired dose quality metric change on a representation (e.g. a graphical representation) of a biological index.
Figure 11A:
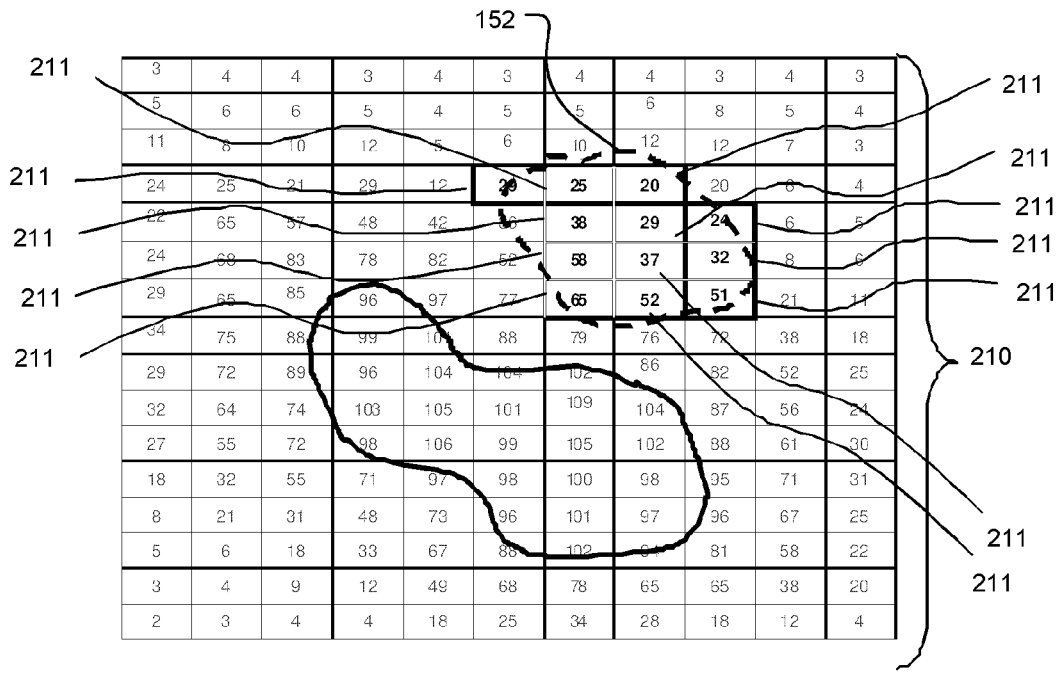
FIG. 11A shows the dose modification voxels determined in accordance with the method of FIG. 4B and corresponding to the FIG. 10 desired dose quality metric change.

FIG. 10 shows an example of an operator communicating a desired dose modification on a representation (e.g. a graphical representation) of another type of dose quality metric (in the illustrated example, a biological index known as the Normal Tissue Complication Probability (NTCP) and Tumor Control Probability (TCP)). In the FIG. 10 example, the NTCP and TCP are displayed in the form of a bar histogram, the operator selects NTCP 203 and indicates (at 201) that NTCP 203 should be reduced. As discussed above, when the operator input is a desired modification in a dose quality metric, block 220 may involve performing an inversion procedure to determine the coordinates (e.g. voxel locations) and magnitudes of the desired dose modifications corresponding to the operator manipulation. The results of this block 220 inversion are depicted in FIG. 11A which shows the coordinates (e.g. voxel locations) 211 of the dose modification corresponding to the FIG. 10 operator manipulation of the NTCP. In the illustrative example of FIG. 11A, the FIG. 10 NTCP manipulation corresponds to desired decreases in the dose magnitude of coordinates (voxel locations) 211 inside healthy tissue structure 152. Although the magnitudes of the corresponding dose modifications are also determined as part of the block 220 inversion procedure, they are not explicitly shown in the schematic depiction of FIG. 11A.

In some embodiments, where desired dose modification input is received in the form of manipulation of dose quality metrics, techniques other than inversion may be used to predict desired dose modification voxels and corresponding dose modification magnitudes. In one particular example, a change to a DVH is received as input which comprises a change to a point on a DVH curve which may be identified by a corresponding dose (D_selected) and a corresponding volume (V_selected). The dose modification voxels may then be identified (in block 220) using a number of techniques including: identifying voxels to be dose modification voxels if the voxels have values falling within D_selected+/-$\Delta$, where $\Delta$ may be a fixed value (which may be operator-selectable), a fraction of D_selected (which may be an operator-selectable fraction), a value determined by calibration or empirical evidence and/or the like. If no voxels are identified to be dose modification voxels, then $\Delta$ may be expanded and voxels may be re-identified until at least one dose modification voxel is identified. If a large number of voxels (e.g. all voxels for that structure or a number of voxels greater than a threshold number or a threshold percentage of the voxels in a structure) are identified to be dose modification voxels, then $\Delta$ may be reduced and voxels may be re-identified. In some embodiments, all voxels inside the structure for which the DVH is changed may be identified as dose modification voxels. By way of non-limiting example, the magnitudes of dose modifications may be determined on the basis of: a fraction of the D_selected value; a fraction of the maximum dose for the structure to which the DVH corresponds; a fraction of a prescription dose assigned to the structure to which the DVH corresponds; a fraction of the maximum prescription dose assigned to all structures; a fraction correlated with (e.g. proportional to) the amount of mouse or similar computer pointing device movement by an operator; a operator-selected quantity; a fixed quantity which may be an operator-configurable parameter or may be a "hard coded" constant; a combination of the above; and/or the like.

Block 220 involves determining the coordinates (e.g. voxel location(s)) and magnitudes of desired dose changes. The coordinates determined in block 220 to be associated with desired dose changes may be referred to as the desired dose modification coordinate(s)/voxel(s) and the associated magnitudes may be referred to as the desired dose modification magnitude(s). Typically, although not necessarily, such desired dose modification coordinate(s) and magnitude(s) are determined on the basis of operator input, but could additionally or alternative be generated based on other forms of input (e.g. computer-generated automated test input and/or the like). Such operator input may involve direct specification of desired dose modification coordinates and magnitudes or indirect specification of desired dose modification coordinates and magnitudes through specification of desired changes to one or more dose quality metrics. The examples shown in FIGS. 7A, 8A, 9A, 10A and 11A are for illustrative purposes only and are not meant to limit the scope of the invention. There are many other dose quality metrics that could be used. Furthermore, each dose quality metric could be represented in many different formats (graphical or otherwise). The block 220 procedure may involve the manipulation of any dose quality metric and representation that is a function of the dose distribution.

In some embodiments, block 220 may involve determining secondary dose modification coordinates/voxels and corresponding dose modification magnitudes in addition to the primary dose modification coordinates/voxels and corresponding dose modification magnitudes determined in accordance with the techniques described above. Secondary dose modification voxels may be defined in a marginal region proximate to the primary dose modification voxels. By way of non-limiting example, such secondary dose modification voxels could be determined to be in a marginal region less than or equal to a threshold number of voxels away from the primary dose modification coordinates. The threshold number of voxels that define the marginal region may be operator-configurable, may be a system parameter which may be determined by one or more suitable calibration procedures, may be a system parameter which may be determined based on empirical testing and/or data and/or the like.

The secondary dose modification magnitudes of the secondary dose modification voxels may be less than the primary dose modification magnitudes of their corresponding primary dose modification voxels. For example, the secondary dose modification magnitudes may be a fraction a of the primary dose modification magnitudes (where $0<=a<=1$). This fraction may be a function of the distance between a given secondary dose modification voxel and its corresponding primary dose modification voxel—e.g. within a marginal region of 3 voxels around a primary dose modification voxel, the fraction a may be relatively high for the secondary dose modification voxels that are nearest neighbors to the primary dose modification voxel; lower for the secondary dose modification voxels that are spaced by one voxel from the primary dose modification voxel; and lowest for the secondary dose modification voxels that are spaced by two voxels from the primary dose modification voxel.

In other respects (e.g. for the purposes of other procedures involved in the methods and systems described herein), secondary dose modification voxels determined as a part of block 220 may be treated, for the most part, in the same manner as primary dose modification voxels determined in block 220. Accordingly, both primary dose modification voxels and secondary dose modification voxels determined in block 220 may be referred to simply as dose modification voxels.

Returning to FIG. 4B, method 18 then proceeds to block 221 which involves determining, for each beam 159 in the block 42 beam configuration, the ray lines 163 that intersect the voxels corresponding to the block 220 desired dose modification coordinates. As discussed above, each of these ray lines 163 is associated with a corresponding beamlet 164 of a corresponding intensity distribution 165. Block 221 may also involve determining the coordinates of these beamlets 164. The ray lines 163 that intersect the voxels corresponding to the block 220 desired dose modification coordinates may be referred to as dose-change ray lines 163 and their corresponding beamlets 164 may be referred to as the dose-change beamlets 164.

Method 18 then proceeds to block 223, which involves adjusting the intensities of the dose-change beamlets 164 identified in block 221. For example, if it is determined in block 220 that the dose corresponding to a particular desired dose modification voxel is to be decreased, then block 223 will typically involve decreasing intensities of the corresponding dose-change beamlets 164. Conversely, if it is determined in block 220 that the dose corresponding to a particular desired dose modification voxel is to be increased, then block 223 will typically involve increasing intensities of the corresponding dose-change beamlets 164.

Changes to the intensities of the dose-change beamlets 164 in block 223 may be effected using a wide variety of techniques. By way of non-limiting example:

- identical magnitude intensity changes or identical percentage intensity changes may be applied to each dose-change beamlet 164;
- identical intensity changes may be applied to one or more subsets of dose-change beamlets 164. Such subsets of dose-change beamlets 164 could correspond, for example, to consecutive dose-change ray lines 163, to dose-change beamlets 164 from every $n^{th}$ (e.g. every second or third) beam 159, to randomly selected dose-change beamlets 164 and/or the like;
- different magnitude or percentage intensity changes may be applied for all or a subset of dose-change beamlets 164; and/or
- the like.

The magnitudes of the block 223 changes to the intensities of the dose-change beamlets 164 may be a function of (e.g. correlated with or proportional to) the block 220 desired dose modification magnitude(s). As discussed briefly above, initialization method 20 may optionally include a procedure (block 47) which establishes an approximate relationship between the intensities of beamlet(s) 164 having ray line(s) 163 that intersect a particular voxel (e.g. dose-change beamlets 164 that intersect a dose modification voxel) and the corresponding dose delivered to the particular voxel. While this approximate relationship is shown as being determined in block 47 of the illustrated embodiment, this is not necessary and this approximate relationship may be determined as a part of one or more other procedures, including, possibly, separate procedures. This approximate relationship may be used as a part of the block 223 determination of changes to the intensities of the dose-change beamlets 164. The approximate relationship between the intensities of dose-change beamlets 164 and the magnitude of a dose change to a dose modification voxel may have a form $D=gni$ where D is the dose (or dose change) for the dose modification voxel, i is an approximate intensity (or intensity change) value for a dose-change beamlet 164, n represents the number of dose-change beamlets 164 for the dose modification voxel and g is a scaling variable. The scaling variable g may be determined in block 47. Thus, for a particular magnitude D of block 220 desired dose modification, the adjustments i to the intensity values of the dose-change beamlets 164 may be determined in accordance with this approximate relationship.

Restrictions may be applied to the block 223 intensity changes to the dose-change beamlets 164. Such restrictions may be related to practical considerations—e.g. to more accurately reflect dose distributions which are achievable in practice. By way of non-limiting example, such intensity-change restrictions may include:

- the intensities of the dose-change beamlets 164 (after the block 223 changes) must be greater than a minimum threshold (e.g. negative intensities are not permitted);
- the intensities of the dose-change beamlets 164 (after the block 223 changes) must be less than a maximum threshold;
- the intensities of the dose-change beamlets 164 (after the block 223 changes) must be controlled such that spatial variations are limited over the two-dimensional extent of a corresponding dose distribution 165 or a dose distribution grid 162 (see FIG. 6). For example, such a restriction may limit the maximum (magnitude or percentage) change in intensity between immediately adjacent (or some range of adjacent) beamlets 164 in a particular dose distribution 165; and/or
- the like.

If it is determined, in block 223, that a prospective intensity change to one or more dose-change beamlets 164 would violate an intensity-change restriction, then a variety of strategies may be employed in block 223 to overcome such a violation. By way of non-limiting example, such strategies may involve:

rejecting the block 220 desired dose modification;

adjusting the block 220 desired dose modification magnitude;

the one or more beams 159 corresponding to dose-change beamlets 164 resulting in intensity limit violations may be omitted from subsequent dose estimation (discussed further below);

the intensity changes to one or more beamlets 164 associated with secondary dose modification voxels may be omitted or the marginal region of secondary dose modification voxels may be reduced;

the magnitudes of one or more intensity changes applied to one or more corresponding dose-change beamlets 164 may be modified until the intensity-change restriction is no longer violated;

a combination of two or more of the above strategies; and/or the like.

Once it is assured that no intensity-change restrictions are violated by the prospective block 223 intensity changes, then the intensities of the dose-change beamlets 164 are modified as discussed above.

In some embodiments, block 221 may involve identifying secondary dose-change beamlets 164 and block 223 may involve adjusting the intensity values of secondary dose-change beamlets 164 in addition to the identification and intensity value adjustment of the primary dose-change beamlets 164 in accordance with the techniques discussed above. Secondary dose-change beamlets 164 may be identified in marginal regions proximate to the primary dose-change beamlets 164. By way of non-limiting example, such secondary dose-change beamlets 164 could be identified to be in a marginal region less than or equal to a threshold number of beamlets away from a primary dose-change beamlet. The threshold number of beamlets that define the marginal region may be operator-configurable, may be a system parameter which may be determined by one or more suitable calibration procedures, may be a system parameter which may be determined based on empirical testing and/or data and/or the like.

The block 223 intensity adjustments to the secondary dose-change beamlets 164 may be less than corresponding adjustments to the primary dose-change beamlets 164. For example, the block 223 intensity adjustments to secondary dose-change beamlets 164 may be a fraction a of the intensity adjustments to the primary dose-change beamlets (where $0<=a<=1$). This fraction may be a function of the distance between a given secondary dose-change beamlet and its corresponding primary dose-change beamlet—e.g. within a marginal region of 3 beamlets around a primary dose-change beamlet, the fraction a may be relatively high for the secondary dose-change beamlets that are nearest neighbors to the primary dose-change beamlet; lower for the secondary dose-change beamlets that are spaced by one beamlet from the primary dose-change beamlet; and lowest for the secondary dose-change beamlets that are spaced by two beamlets from the primary dose-change beamlet.

In other respects (e.g. for the purposes of other procedures involved in the methods and systems described herein), secondary dose-change beamlets 164 may be treated, for the most part, in the same manner as primary dose-change beamlets 164. Accordingly, both primary dose-change beamlets and secondary dose-change beamlets may be referred to simply as dose-change beamlets.

Method 18 (FIG. 4B) then proceeds to block 224 which involves determining changes in the achievable dose distribution based on the block 223 changes to the intensities of the dose-change beamlets 164 and updating the dose distribution accordingly. It will be appreciated that modifying the intensities of the dose-change beamlets 164 will not only impact the estimated dose delivered to the desired dose modification voxels identified in block 220, but will also impact the estimated dose delivered to other voxels (e.g. voxels in and around the paths of the dose-change ray lines 163). Typically, the maximum changes to the achievable dose distribution (caused by changes to the intensities of the dose-change beamlets 164) will occur in the desired dose modification voxels and the changes to the achievable dose distribution will be somewhat less in voxels surrounding the desired dose modification voxels.

The block 224 estimation of the changes in the dose distribution may involve the use of known dose estimation techniques such as, Monte Carlo, collapsed cone convolution, pencil beam, anisotropic analytical algorithm, Boltzman equation solvers and/or the like. The block 224 estimation of dose distribution may involve one or more of the rapid dose distribution estimation techniques described herein. It is generally desirable that the block 224 dose estimation technique be computationally efficient. Block 224 may involve using dose estimation techniques that are able to update dose estimates resulting from intensity changes to particular dose-change beamlets 164 along individual dose-change ray lines 163 which may be more computationally efficient. The resulting changes in the dose estimates may then be added (or subtracted in the case of a dose reduction) to the existing dose distribution estimate. In this regard, block 224 need only involve updating the achievable dose distribution for the dose-change beamlets 164 whose intensities were modified in block 223—i.e. it is not necessary to recalculate the entire dose distribution estimate in block 223. Typically, the number of dose-change beamlets 164 having their intensities modified in block 223 will be a relatively small subset of the beamlets 164 associated with a given beam 159. In accordance with some dose estimation techniques, the block 224 dose estimation update may therefore consume a relatively small amount of computational resources compared to a full dose distribution estimate.

Figure 4D:
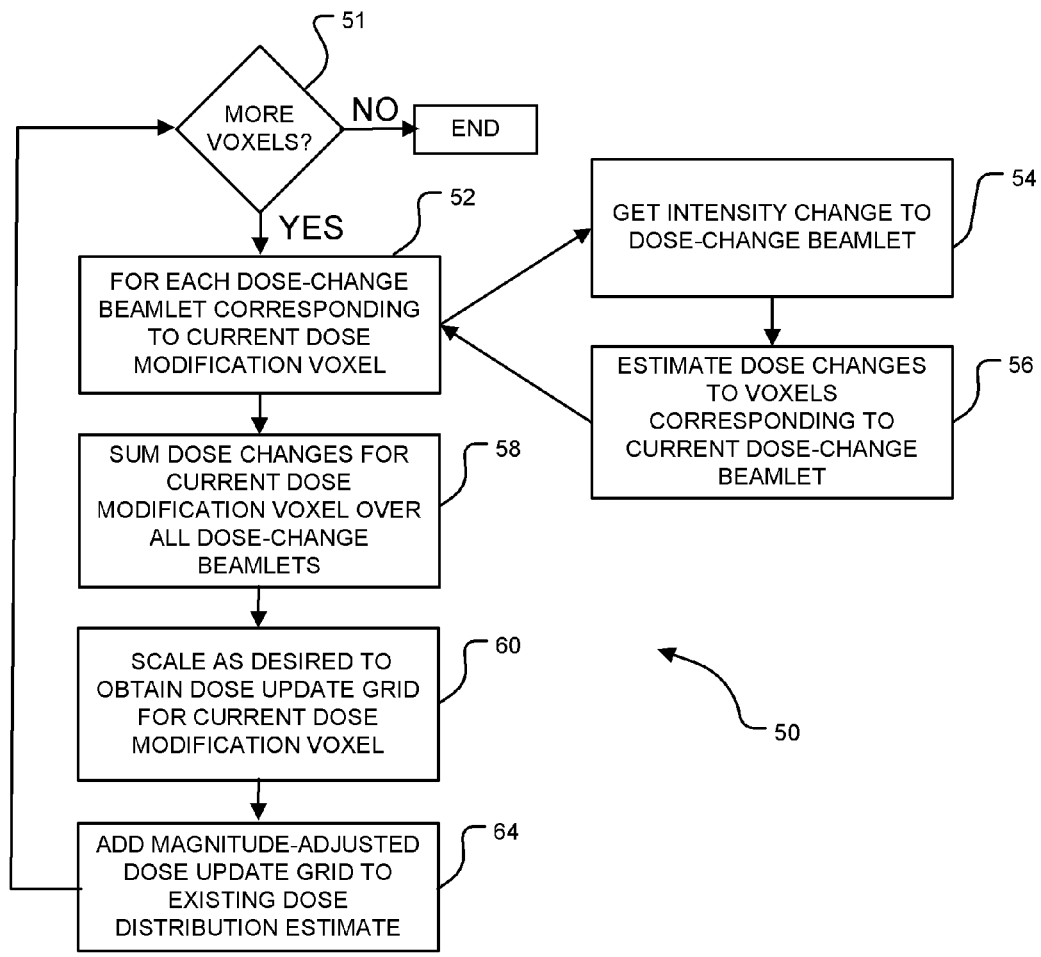
FIG. 4D is a flowchart depicting a dose-estimation update method for determining the changes in estimated dose distribution which may be used with the method of FIG. 4B according to a particular embodiment.

FIG. 4D depicts a dose-estimation update method 50 for determining the changes in achievable dose distribution which may be used in block 224 according to a particular embodiment. Dose-estimation update method 50 of the illustrated embodiment assumes that a plurality of dose modification voxels were specified in block 220 (e.g. the dose distribution changes requested by an operator in block 220 resulted in modifications to the dose at a plurality of coordinates/voxels). Dose-estimation update method 50 begins in block 51 which involves an inquiry into whether there are more dose-modification voxels to be considered in the dose-estimation update. In the first loop through method 50, the block 51 inquiry will typically be positive (block 51 YES update path) and method 50 will proceed to block 52. Before proceeding to block 52, block 51 may also involve selecting one dose modification voxel to be the current dose modification voxel for this iteration of the method 50 dose-estimation update loop.

Block 52 of the illustrated embodiment involves identifying the dose-change beamlets 164 which correspond to the current dose modification voxel. Such dose-change beamlets 164 may be those identified in block 221 (FIG. 4B) as having corresponding dose-change ray lines 163 that intersect the current dose modification voxel. For each such dose-change beamlet 164, method 50 involves obtaining the intensity change for that beamlet 164 (in block 54) and estimating the dose contribution attributable to the intensity change for that beamlet 164 (in block 56). The block 56 estimation of the dose contribution attributable to the intensity change for a particular dose-change beamlet 164 may involve the use of known dose estimation techniques such as, Monte Carlo, collapsed cone convolution, pencil beam, anisotropic analytical algorithm, Boltzman equation solvers and/or the like. The block 56 dose estimation may additionally or alternative involve one or more of the rapid dose distribution estimation techniques described further below.

Method 50 of the illustrated embodiment then proceeds to block 58 which involves summing the block 56 estimated dose contributions for all of the dose-change beamlets 164 corresponding to the current dose modification voxel to obtain an estimated dose distribution update for the current dose modification voxel. In block 60, the block 58 dose distribution update for the current dose modification voxel may optionally be scaled to provide a scaled dose update grid corresponding to the current dose modification voxel. The term dose update grid may be used interchangeably with dose update distribution or dose modification distribution. As discussed above, an approximate relationship may be established (e.g. in block 47 of initialization method 20) between the dose change to a dose modification voxel and the corresponding intensity changes to the dose-change beamlets 164 and, in accordance with this approximate relationship, changes to the intensities of the dose-change beamlets 164 may be established in block 223. However, this relationship is only approximate. Consequently, the block 58 sum of the dose change contributions for each of the dose-change beamlets 164 may not yield the desired magnitude (e.g. the block 220 desired magnitude) of dose change to the dose modification voxel. In such cases, the block 58 sum of the dose change contributions for each of the dose-change beamlets 164 may be scaled in block 60 to obtain a scaled dose update grid which achieves the desired magnitude of dose change (e.g. the block 220 desired dose change magnitude). The block 60 scaling of the dose update grid may also be accompanied by corresponding scaling to the intensities of the dose-change beamlets. The dose-change beamlets may be scaled by a similar factor. For example, if the block 60 scaling of the dose change grid involves a scaling factor s, then the intensities of the dose-change beamlets may be scaled by the same scaling factor s.

Since there may be an approximate relationship established between the dose change to the dose modification voxel and the corresponding intensity changes to the dose-change beamlets 164, the block 60 scaling may be minimal. In some embodiments, block 60 scaling is not used. In some instances, even where block 60 scaling is used, it may be desirable to limit the amount of block 60 scaling. For example, it may be undesirable to scale in a manner which may result in one or more beamlet intensities that violate beam restrictions, such as any of the beam restrictions discussed above. In some cases (e.g. because scaling is not used or is limited in amount), it may not be possible to achieve the desired dose change magnitude (e.g. the block 220 dose modification magnitude) in the dose modification voxel. This circumstance is permissible.

Figure 12:
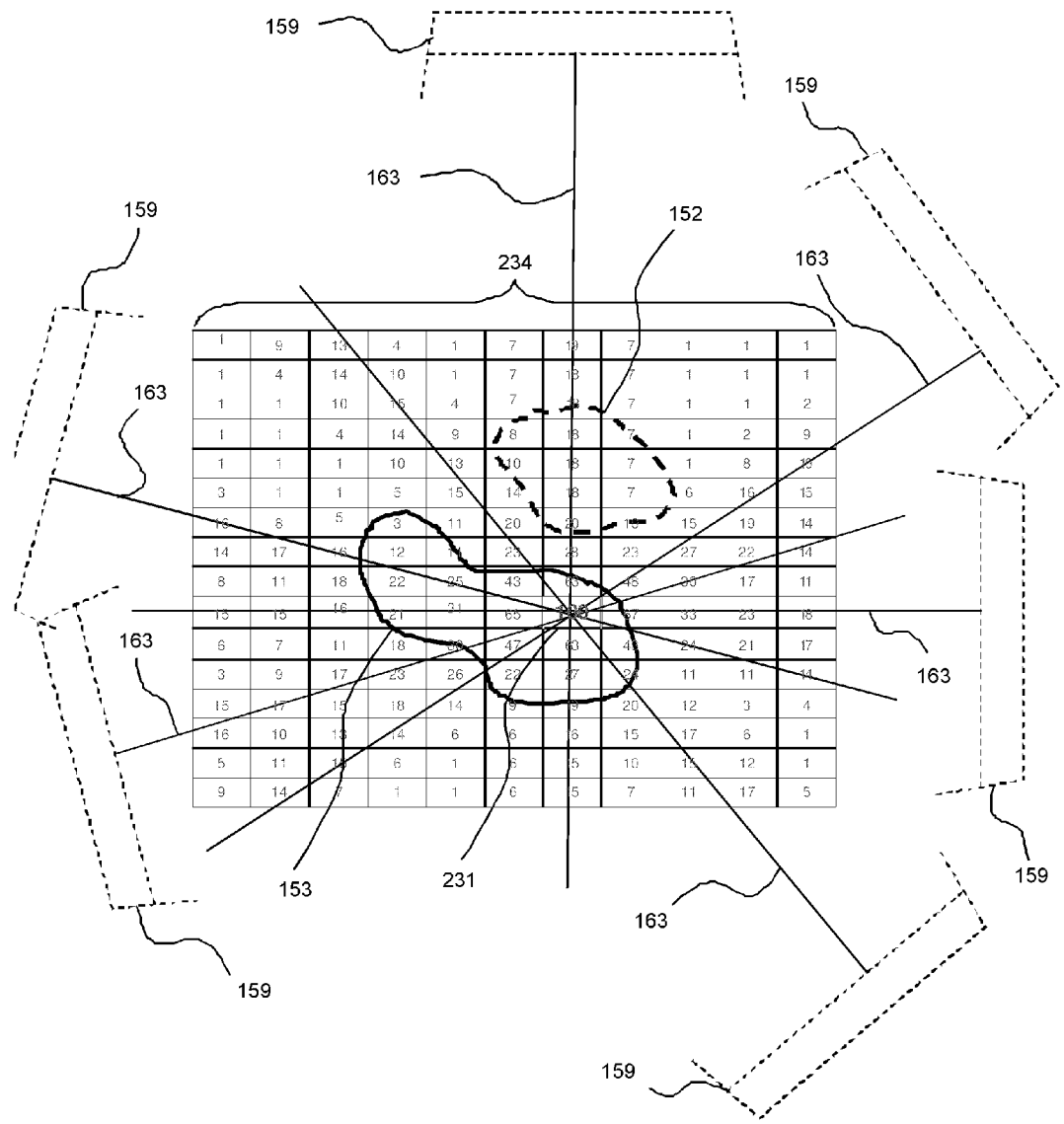
FIG. 12 schematically depicts an example of a dose update grid illustrative of a technique which may be used to update the dose distribution as part of the method of FIG. 4B according to a particular embodiment.

FIG. 12 schematically depicts an example of a scaled dose update grid 234 corresponding to a particular dose modification voxel 231 according to a particular embodiment. In the FIG. 12 depiction, the current dose modification coordinate is voxel 231 in target tissue structure 153. Referring to FIGS. 4B, 4D and 12, block 221 identifies the illustrated ray lines 163 (and corresponding beamlets 164) for a series of beams 159 to be the dose-change ray lines 163 and dose-change beamlets 164. The changes to the intensity values of the corresponding dose-change beamlets 163 (determined in block 223 of FIG. 4B) are obtained in each iteration of block 54 (FIG. 4D) and their respective dose distribution contributions are estimated in each iteration of block 56 (FIG. 4D). These block 56 dose distribution contributions are summed in block 58 and optionally scaled in block 60 to obtain scaled dose update grid 234 illustrated in FIG. 12.

FIG. 12 shows a dose-update grid 234 comprising dose update values. The dose update values determined for particular voxels in grid 234 are represented by the numerical values shown in the boxes of dose-update grid 234. The dose update values for grid 234 are expressed in terms of scaled dose update values—i.e. the dose update value of 100% at the current dose modification voxel 231 represents a dose update of 100% of the desired dose change magnitude (e.g. the block 220 desired dose change magnitude) and the dose update values of the other voxels around current dose modification voxel 231 represent lower percentages of the desired dose change magnitude. FIG. 12 shows that the maximum dose distribution change occurs at the current dose modification voxel 231 but that dose distribution changes also occur to a lesser extent in surrounding voxels. It will be appreciated that dose-update grid 234 shown in FIG. 12 is a two-dimensional representation, but that in practice the dose-update grid determined in accordance with method 50 will be three-dimensional.

The block 60 dose-update grid 234 may represent an amount of dose to add to (or subtract from) an overall achievable dose distribution in block 64. As discussed above, an initial overall achievable dose distribution may be determined in block 46 (FIG. 4C). The block 46 initial estimate of the overall dose distribution may be updated in one or more previous iterations of method 18 (FIG. 4B). Block 64 may involve adding the dose update values of dose-update grid 234 to the overall dose distribution estimate. The overall dose distribution estimate will then be updated with the dose distribution contribution for the current dose modification voxel 231. Method 50 then loops back to block 51 to determine whether there are other dose modification voxels to be considered in the method 50 dose-estimation update. After one or more loops through blocks 52-64, the block 51 inquiry will be negative, terminating method 50.

It will be appreciated by those skilled in the art that dose-estimation update method 50 of the FIG. 4D embodiment represents one particular method of updating dose estimates as a part of block 223 (FIG. 4B). In other embodiments, equivalent dose-estimation updates could be determined using different orders of operations. By way of non-limiting example, rather than looping through dose modification voxels and dose-change beamlets, the same or similar dose-estimation update results could be obtained by identifying all dose modification voxels, summing the intensity changes to the dose-change beamlets resulting from all of the dose modification voxels and then estimating the dose changes corresponding to all of the dose-change beamlets in a single dose estimation process. Other orders of operations are conceivable for estimating dose updates as a part of block 224 (FIG. 4B). In some embodiments, the scaling and multiplication operations of blocks 60 and 62 are not required as the magnitude of the desired dose change for a particular dose modification voxel (see block 220 of FIG. 4B) may already be taken into account in the amount of the intensity changes to the dose-change beamlets 164. In some embodiments, where all dose modification voxels are simultaneously updated, scaling may occur at some level that is a combination (e.g. some type of average) of the desired scaling for all of the dose modification voxels.

Method 50 of the illustrated embodiment involves obtaining individual intensity changes to dose-change beamlets (in block 54), estimating dose changes (in blocks 56, 58, 60, 62) and then adding (or subtracting) dose changes to the existing dose distribution (in block 62) to obtain the block 224 (FIG. 4B) updated dose distribution. This illustrated embodiment works with changes to intensities and doses and is possible because many dose estimation techniques obey the principal of superposition. In other embodiments, dose-estimation update methods which may be used in block 224 of method 18 (FIG. 4B) may involve discarding an existing dose distribution (or part(s) thereof) and then estimating a replacement dose distribution (or replacement part(s) thereof). Such replacement dose distributions (or replacement part(s) thereof) may be based on the absolute values of the adjusted intensities of the dose-change beamlets 164 (i.e. rather than the changes to the intensities of the dose change beamlets 164).

In one example of such an embodiment, the parts of an existing dose distribution which could be discarded comprise the parts of the existing dose distribution contributed by the previous values of dose-change beamlets 164, in which case the estimated replacement parts of the updated dose distribution estimate would be the dose contributions from the new intensity values of the dose-change beamlets 164. In another example of such an embodiment, the parts of an existing dose distribution which could be discarded comprise the parts of the existing dose distribution contributed by the intensity distributions 165 of beams 159 (e.g. intensity distributions 165 having one or more dose-change beamlets 164), in which case the replacement parts of the updated dose distribution estimate would be the dose contributions from the modified intensity distributions 165 of beams 159 (e.g. intensity distributions 165 modified by updated intensity values for one or more dose-change beamlets 164). In another example of such an embodiment, the entire existing dose distribution could be discarded and a replacement dose distribution could be estimated based on dose contributions from all of the updated intensity distributions 165 of all of the beams 159. These techniques of discarding parts of existing dose distributions and estimating replacement parts for the updated dose distribution estimate may be particularly useful where they are used in conjunction with the convolution technique for rapid estimation of achievable dose distribution which is discussed further below.

At the conclusion of method 50 and/or block 224 (FIG. 4B), the achievable dose distribution has been updated to accommodate the desired block 220 dose distribution changes (e.g. operator-requested dose distribution changes). Those skilled in the art will appreciate from the discussion above, that there are a variety of techniques in which to update the achievable dose distribution in block 224. While some such techniques have been discussed above, there may still be other suitable techniques which may be modifications of those discussed above or which may be different from those discussed above. Nevertheless, at the conclusion of block 224, the achievable dose distribution has been updated to accommodate the desired block 220 dose distribution changes. The updated estimate of the dose distribution at the conclusion of block 224 may be displayed for the operator. Returning to FIG. 4B, method 18 may optionally proceed to block 225 where one or more dose quality metrics may be updated on the basis of the block 224 updated dose distribution. Such dose quality metrics may also be displayed for the operator.

FIG. 7B shows a cross-section of the updated dose distribution estimate 173 (determined in block 224) as a result of the FIG. 7A desired dose change obtained or otherwise determined in block 220. Recalling that the FIG. 7A dose change corresponded to a desired reduction in the dose delivered to voxel 171 of healthy tissue structure 152, FIG. 7B shows that the maximum dose reduction occurs at voxel 171. However, updated dose distribution estimate 173 of FIG. 7B also shows that the dose estimate was reduced for voxels surrounding voxel 171. The updated dose distribution shown in FIG. 7B may be displayed to an operator in block 224.

Figure 8B:
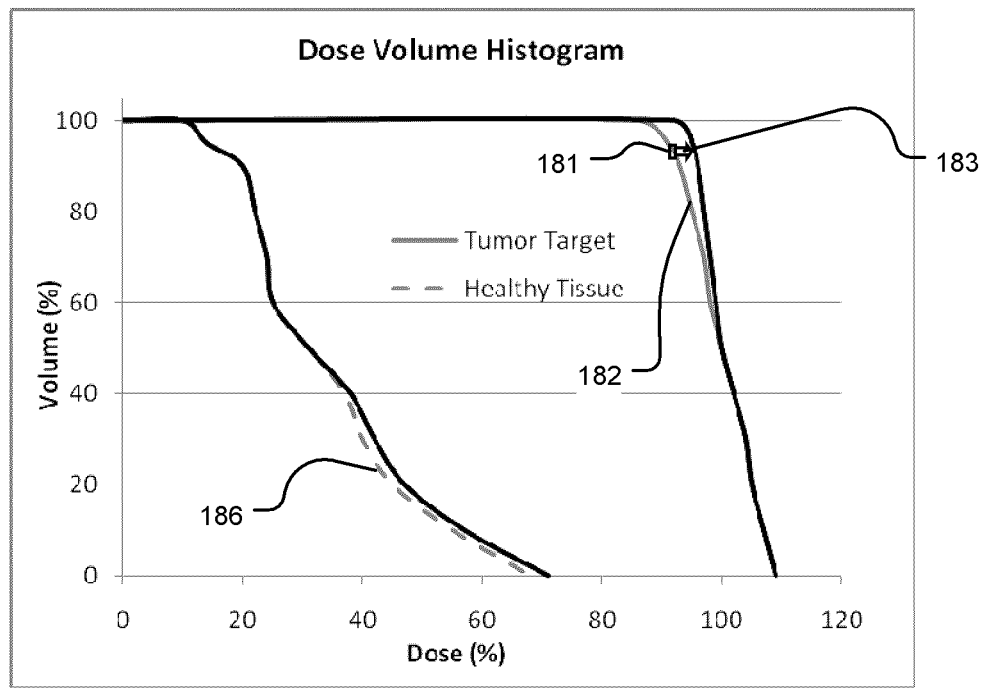
FIG. 8B shows the updated DVH determined in accordance with the method of FIG. 4B as a result of the FIG. 8A desired dose change.

FIG. 9B shows a cross-section of the updated dose distribution estimate 193 (determined in block 224) as a result of the FIG. 9A desired dose change determined in block 220. As discussed above, the FIG. 9A desired dose change corresponds to a desired change in the FIG. 8A DVH which involves an increase in the dose delivered to target tissue structure 153 and corresponding increases to the dose delivered to dose modification voxels 191. FIG. 9B shows that the maximum dose increases occur at dose modification voxels 191, but that dose increases also occur for voxels surrounding voxels 191. The updated dose distribution shown in FIG. 9B may be displayed to an operator in block 224. FIG. 8B shows the updated DVHs corresponding to the updated dose distribution estimate of FIG. 9B. The FIG. 8B DVHs may be determined and displayed to an operator in block 225. FIG. 8B shows that the target tissue DVH 182 changes most near the desired change point 181, but that smaller changes also occur to healthy tissue DVH 186.

Figure 11B:
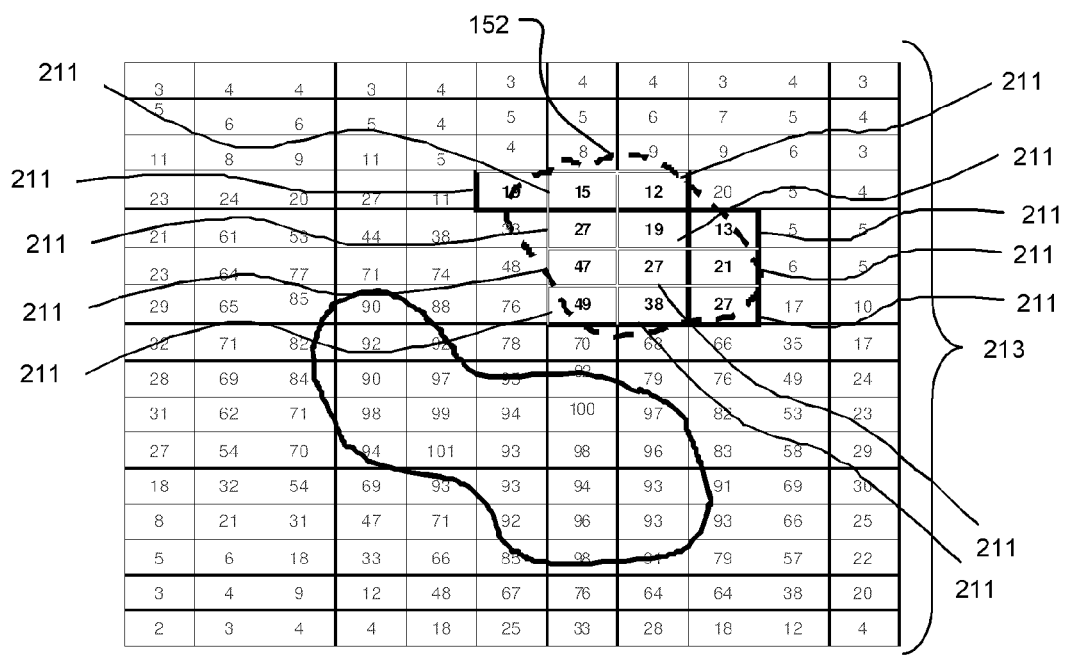
FIG. 11B shows a cross-section of the updated dose distribution determined in accordance with the method of FIG. 4B as a result of the FIG. 11A desired dose change.

FIG. 11B shows a cross-section of the updated dose distribution estimate 213 (determined in block 224) as a result of the FIG. 11A desired dose change determined in block 220. As discussed above, the FIG. 11A desired dose change corresponds to a desired change in the FIG. 10 NTCP biological index which involves a decrease in the dose delivered to healthy tissue structure 152 and corresponding decreases to the dose delivered to dose modification voxels 211. FIG. 11B shows that the maximum dose decreases occur at dose modification voxels 211, but that dose decreases also occur for voxels surrounding voxels 211. The updated dose distribution shown in FIG. 11B may be displayed to an operator in block 224. Although not expressly shown in the drawings, updated biological indices may be determined and displayed to an operator in block 225.

In some embodiments, method 18 and/or portions thereof may be performed in loops. For example, at the conclusion of blocks 224 and/or 225, method 18 may loop back to block 220 to permit additional dose changes (e.g. operator input of additional desired dose changes). In some embodiments, dose estimation updates (block 224) and/or updates to dose quality metrics (block 225) may be performed and/or displayed periodically. The periods between such computation and/or display updates (which need not be temporal periods) may be defined using a variety of techniques. By way of non-limiting example, updates may be performed:

- each time that a block 220 desired dose modification is requested or otherwise determined;
- after multiple block 220 desired dose modifications are requested or otherwise determined;
- after a time interval;
- if several block 220 desired dose modifications are requested, it may be desirable to display a result which includes some subset of the requested dose modifications;

after an achievable dose distribution and/or dose quality metric has changed by a threshold amount;

a combination of the above (e.g. after a time interval or a threshold number of desired dose modifications are requested); and/or the like.

Some of the procedures of method 18 may overlap with one another. For example, an operator may request multiple desired dose modifications (block 220) prior to the completion of the remainder of method 18. As desired dose modifications are communicated by the operator (or otherwise obtained in block 220), the rest of method 18 may be carried out, so that modifications may be continuously applied and the achievable dose distribution may be continuously updated. It may occur that one or more further desired dose modifications are requested prior to completion of the rest of method 18 for a previous desired dose modification update. Further desired dose modifications may be places in a queue so that, once method 18 is completed for a particular desired dose modification, method 18 may be completed for the next desired dose modification in the queue. In this way all desired dose modification request changes will eventually be processed. In other embodiments, further desired dose modification requests may only be permitted after method 18 has completed for a previous desired dose modification request. Additional example schemes for addressing further desired dose modification requests while method 18 is being carried out for previous desired dose modification requests include, but are not limited to, rejection of every 2nd, 3rd or $N^{th}$ request (where N is an integer) while the remaining requests are placed in a queue.

During method 18 (e.g. as a part of block 224 and/or method 50 (FIG. 4D)), it may be desirable to prohibit or restrict certain desired dose modification requests (e.g. block 220 desired dose modification requests). For example, reducing dose to target tissue structures 153 below a threshold or increasing dose to healthy tissue structures 152 above a threshold may be considered undesirable. Such thresholds may comprise operator-specified thresholds, system threshold parameters and/or the like, for example.

Restrictions (e.g. thresholds) may be specified for the dose distribution estimate itself and/or for one or more dose quality metrics. As part of method 18, proposed updates to the achievable dose distribution and/or proposed updates to one or more dose quality metrics may be evaluated with respect to one or more such restrictions. In the event that such a restriction is violated, a variety of actions may be taken. By way of non-limiting example:

the block 220 desired dose modification request corresponding to the restriction violation may be rejected;

the magnitude of the block 220 desired dose modification request may be adjusted so that the restriction is no longer violated;

one or more additional changes to the block 220 desired dose modification request may be made in attempt to overcome the violation of the restriction; and/or the like.

In the event that one or more additional changes to the block 220 desired dose modification request are changes in attempt to overcome violation of the restriction, the following exemplary procedure may be used:

restriction violating coordinates (e.g. voxels) corresponding to the voxels in the dose distribution that violate the restriction may be determined. Such restriction violating coordinates may be determined in a manner similar to the determination of the block 220 dose modification coordinates (e.g. for dose quality metrics).

dose modifications may be applied to the restriction violating coordinates and a resulting dose distribution estimates may be obtained in accordance with method 18 of FIG. 4B.

after the new dose distribution estimates are calculated for the changes to the restriction violating coordinates, the new dose distribution estimates may be evaluated for restriction violations.

If one or more restrictions remains violated, then the procedure can be repeated until there are no longer restriction violations.

At the conclusion of method 18 (any loops or any portions thereof), method 18 yields an achievable dose distribution and/or an estimated dose quality metric. Preferably, such achievable dose distribution and/or estimated dose quality metric will meet the operator's treatment objectives. The achievable dose distribution and/or dose quality metrics may be output for use by another method or system. Such methods or systems may comprise, for example, a computerized database, a treatment plan optimization system, a radiation delivery apparatus and/or as an input to any other system or device used in radiation treatment. The corresponding beamlet intensities and/or dose restrictions associated with the FIG. 18 dose distribution estimation may also be output for use by any such method or system.

By way of non-limiting example, as discussed above, method 18 of FIG. 4B may comprise a method for implementing the block 142 generation and manipulation of achievable dose distribution as a part of radiation delivery method 16 (FIG. 4A). In such an embodiment, the block 224 dose distribution estimates and the corresponding beamlet intensities may be used in block 143 of radiation delivery method 18 to perform an iterative optimization process or the like to derive radiation delivery parameters (e.g. beam configuration parameters and/or beam delivery parameters). If iterative optimization is used in block 143, the dose estimation process involved in such optimization may (but not necessarily) be the same as the dose estimation process involved in the dose generation and manipulation procedure of block 142 (e.g. in block 46 of method 20 and block 56 of method 50). For example, in some embodiments, the dose estimation procedures used in dose generation and manipulation block 142 may comprise one or more of the rapid dose estimation techniques described in more detail below; however, the block 143 iterative optimization may involve one or more traditional methods of dose estimation (e.g. Monte Carlo, collapsed cone convolution, pencil beam, anisotropic analytical algorithm, Boltzman equation solvers and/or the like) which may be more accurate for determining radiation delivery parameters.

If iterative optimization is used in block 143, one or more outputs from the block 142 (method 18) generation and manipulation of estimated dose may be used to aid in the derivation of the block 143 radiation delivery parameters. By way of non-limiting example:

the block 224 achievable dose distribution and/or block 225 estimated dose quality metric(s) may be used in block 143 to define the optimization objectives (e.g. cost function or the like) of the optimization process;

the beamlet intensities determined in block 223 and corresponding to the final block 224 achievable dose distribution may be used to determine the beam intensity required of the radiation delivery apparatus;

other metrics derived from the block 224 achievable dose distribution may be used to define optimization objectives (e.g. a cost function or the like) of the block 143 optimization process; and/or the like.

Block 143 does not necessarily require the performance of an optimization process. In some embodiments, the output(s) of the block 142 generation and manipulation of achievable dose distributions (e.g. block 224 achievable dose distributions, block 225 dose quality metrics and/or block 223 beamlet intensities) may lead be convertible directly to radiation delivery parameters of sufficient accuracy. Such direct derivation of radiation delivery parameters (i.e. without iterative optimization) in block 143 may occur, for example, where the block 224 achievable dose distributions are calculated according to a sufficiently accurate estimation technique and various restrictions (e.g. on beamlet intensities and/or dose estimates) are sufficiently robust.

Radiation treatment method 16 may then proceed to block 144, where the block 143 radiation delivery parameters may be transferred to a radiation delivery apparatus. In block 145, a controller associated with the radiation delivery apparatus (equipped with the radiation delivery parameters) may then cause the radiation delivery apparatus to deliver radiation to the subject. The radiation received by the subject is preferably similar to the achievable dose distribution output predicted in blocks 142 (FIG. 4A) and/or 224 (FIG. 4B).

Systems and methods according to various embodiments described herein involve estimating dose distributions based on one or more beamlet intensities. Non-limiting examples of estimating dose distributions include: the block 218 initialization procedure of method 18 (FIG. 4B) and the corresponding estimate of the initial dose distribution in block 46 of initialization method 20 (FIG. 4C); the block 224 dose-estimation update procedure of method 18 (FIG. 4B) and the corresponding estimation at block 56 (FIG. 4D); and any dose distribution estimation that may take place in the block 143 procedure for deriving radiation delivery parameters (e.g. during iterative optimization). As discussed above, there are a variety of known techniques (e.g. Monte Carlo, collapsed cone convolution, pencil beam, anisotropic analytical algorithm, Boltzman equation solvers and/or the like) for estimating dose distribution based on beamlet intensities. Any such techniques could be used in any of the intensity distribution estimation procedures described herein, although it may be preferable that one technique is used consistently throughout block 142 and one technique is used consistently throughout block 143 of radiation treatment method 16.

One aspect of the invention provides different methods for estimation of achievable dose distributions. Such methods may be used to perform the dose distribution estimation procedures in any of the other methods and systems described herein. In some embodiments, methods for estimating achievable dose distributions are provided which are relatively rapid in comparison to currently available dose estimation techniques, such as Monte Carlo, collapsed cone convolution, pencil beam, anisotropic analytical algorithm, Boltzman equation solvers and/or the like. Dose distributions estimated in accordance with the inventive methods described herein may be referred to as rapid dose distribution estimates to contrast them with traditional dose distribution estimates obtained using known techniques. Methods of estimating achievable dose distributions according to various embodiments of the invention may involve simplifications based on ray lines 163 (and corresponding beamlets 164 of intensity distributions 165) emanating from radiation source 161 and knowledge of how such ray lines 163 interact with calculation grids which are used to map three-dimensional space in subject 160 (see FIG. 6). By way of non-limiting example, such simplifications may involve:

using simplified models of radiation scatter and/or radiation transport as compared to traditional dose distribution estimation techniques;

omitting the effects of inhomogeneous subject density;

omitting attenuation of beams 159 as a function of depth in subject 160;

ignoring the distance from the radiation source to the subject 160;

a combination of the above; and/or the like.

Given a set of beams 159 with known intensity distributions 165, rapid estimates of achievable dose distributions (and corresponding dose quality metrics) determined in accordance with some of the inventive methods described herein may not yield the same achievable dose distributions (and corresponding dose quality metrics) as traditional dose estimation methods. However, where suitable limits are imposed on beams 159, corresponding intensity distributions 165 and the intensities of individual beamlets 164, rapid dose distribution estimation techniques described herein may yield dose distribution estimates that are reasonably close to those that are physically deliverable. Suitable examples of limitations on beams 159, corresponding intensity distributions 165 and the intensities of individual beamlets 164 are described above. In some embodiments, where rapid estimation of achievable dose distributions are used during the process of treatment planning and/or delivery (e.g. method 16 of FIG. 4A), iterative optimization procedures may be used (e.g. in block 143 of method 16) to determine radiation delivery parameters (e.g. physical system parameters) capable of delivering the desired fast dose distribution estimates.

Figure 13:
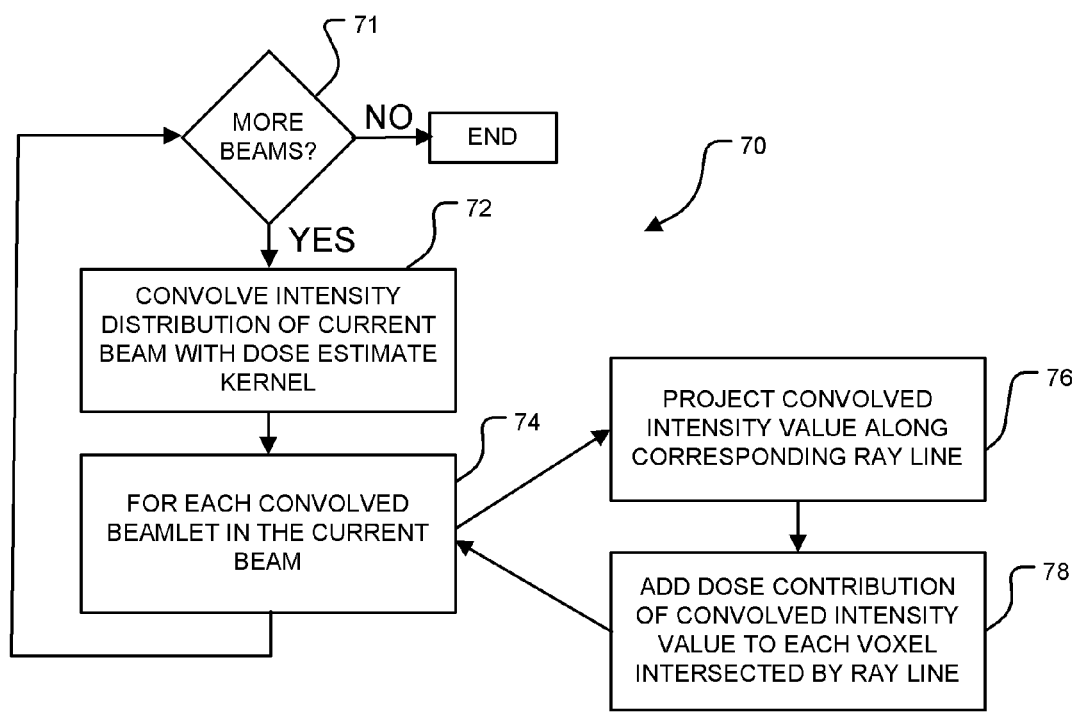
FIG. 13 is a schematic illustration of a method for rapid estimation of achievable dose distribution according to a particular embodiment.

FIG. 13 is a schematic illustration of a method 70 for rapid estimation of achievable dose distribution according to a particular embodiment. As discussed in more detail below, method 70 for rapid estimation of achievable dose distributions involves, for each beam 159 in a beam configuration, convolving the two-dimensional intensity distribution 165 i(x,y) associated with the beam 159 with a two-dimensional dose estimate kernel k(x,y) to obtain a convolved intensity distribution and, for each convolved beamlet in the convolved intensity distribution, projecting the convolved intensity value along the ray line 163 associated with the convolved beamlet. Estimating achievable dose distributions using a dose estimate kernel k(x,y) in accordance with method 70 may be an efficient way of estimating an achievable dose distribution based on an intensity distribution.

Rapid dose distribution estimation method 70 commences in block 71 which involves an inquiry into whether there are more beams to be considered in the rapid dose distribution estimation. In the first loop through method 70, the block 71 inquiry will typically be positive (block 71 YES update path) and method 70 will proceed to block 72. Before proceeding to block 72, block 71 may also involve selecting one beam to be the current beam for this iteration of the method 70 rapid dose distribution estimation loop. In block 72, method 70 involves performing a convolution operation which comprises convolving the two-dimensional intensity distribution i(x,y) associated with the current beam with a two-dimensional dose estimate kernel k(x,y) to obtain a two-dimensional convolved intensity distribution f(x,y). The coordinates x,y may be defined in the plane of grid 162 of the intensity distribution 165 (see FIG. 6). The resultant convolved intensity distribution f(x,y) may be defined for, or otherwise mapped to, the coordinates associated with the beamlets 164 of the current beam which may, in the context of the convolved intensity distribution f(x,y), be referred to as convolved beamlets 164.

As part of block 72, each convolved beamlet 164 is associated with a corresponding ray line 163 and a corresponding convolved intensity value.

The dose estimate kernel k(x,y) may be intended to approximate the amount of radiation scatter and energy transport resulting from radiation interacting with tissue. In some embodiments, the dose estimation kernel k(x,y) comprises a point spread function.

In some embodiments, the dose estimation kernel k(x,y) comprises a linear combination of a plurality of point spread functions. In one exemplary embodiment, the dose estimate kernel k(x,y) comprises a linear combination of one or more 2-dimensional Gaussian functions:

$$k(x,y) = A_1 e^{-(x^2-y^2)/\sigma_1^2} + A_2 e^{-(x^2-y^2)/\sigma_2^2} + \ldots + A_n e^{-(x^2-y^2)/\sigma_n^2} \quad (1)$$

where $A_i$ are magnitude variables of the various Gaussian functions and $\sigma_i$ are variables representative of the radial spread of the various Gaussian functions. The variables $A_i$ and $\sigma_i$ may be operator-configurable, may be system parameters which may be determined by one or more suitable calibration procedures, may be system parameters which may be determined based on empirical testing and/or data and/or the like. The variables $A_i$ and $\sigma_i$ may depend on the type of radiation. It will be appreciated by those skilled in the art that the equation (1) point spread function is merely an example point spread function and that dose estimation kernel k(x,y) may comprise a variety of other point spread functions and/or linear combinations of point spread functions. In some embodiments, the dose estimation kernel k(x,y) (or one or more parameters thereof) may be experimentally determined (e.g. from calibration type measurements and/or the like). In some embodiments, the dose estimation kernel k(x,y) (and/or its parameters) may be stored in accessible memory (e.g. in a look up table or the like).

Convolution operations can be computationally intensive and can consume relatively large amounts of processing resources. To reduce this burden on computational resources, the block 72 convolution may involve converting the two-dimensional intensity distribution i(x,y) and the two-dimensional dose estimate kernel k(x,y) to the Fourier domain. Advantageously, a convolution operation in the spatial domain may be implemented as a multiplication operation in the Fourier domain. The two-dimensional intensity distribution i(x,y) and the two-dimensional dose estimate kernel k(x,y) may be converted to the Fourier domain using any of a wide variety of known computational techniques for performing Fourier transforms (e.g. fast Fourier transforms (FFT) and/or the like). The convolved intensity distribution f(x,y) may therefore be calculated according to:

$$f(x,y) = \text{IFT}[\text{FT}[i(x,y)] \times \text{FT}[k(x,y)]] \quad (2)$$

where FT[●] and IFT[●] are respectively Fourier transform and inverse Fourier transform operators. It will be appreciated that, in absence of a change to the kernel function k(x,y), the Fourier transform of the kernel function FT[k(x,y)] need only be calculated once and the result may be stored (e.g. in a look up table in accessible memory and/or the like).

Method 70 then proceeds to block 74 which involves a loop for each convolved beamlet 164 in the current beam 159. For each convolved beamlet 164 in the current beam 159: block 76 involves projecting the ray line 163 corresponding to the convolved beamlet 164 into the calculation grid and identifying voxels in the calculation grid which are intersected by the ray line 163 and block 78 involves adding the convolved intensity value for the convolved beamlet 164 to each voxel identified in block 76. Method 70 then loops back to block 71 to determine whether there are more beams to be considered in the method 70 rapid dose estimation. After one or more loops through blocks 72-78, the block 71 inquiry will be negative, terminating method 70.

Rapid dose distribution estimation method 70 involves the principal of superposition. As discussed above in connection with dose estimation update method 50, dose estimation techniques which involve the principal of superposition may operate on changes (e.g. determining changes to dose distributions that result from changes to beam and/or beamlet intensities) or on absolute values (e.g. discarding dose contributions from previous values of beam and/or beamlet intensities and estimating new dose contributions based on the new absolute values of the beam and/or beamlet intensities).

The above-described method 70 for rapid dose distribution estimation may be augmented by incorporating an estimate for attenuation of radiation as it passes through the subject. For this purpose, in some embodiments, an additional attenuation function a(d) may be applied to account for such attenuation. Such an attenuation function a(d) may cause the block 72 convolved intensity values to decrease with distance d along the ray lines 163 which they are projected in block 76, so that their respective block 78 dose contributions decrease with distance d along their respective ray lines 163. By way of non-limiting example, an attenuation function a(d) may be multiplied to the dose contribution values in block 78 before such dose contribution values are added to each voxel intersected by ray lines 163. A variety of different decreasing attenuation functions a(d) are suitable to model this attenuation and the choice of particular attenuation function a(d) may depend on the characteristics of the radiation. In one particular embodiment, an attenuation function a(d) may be provided by an exponential function of the form:

$$a(d) = B e^{-kd} \quad (3)$$

where B is a magnitude variable, k is a variable characterizes the rate of attenuation with depth and d represents the distance along a particular ray line 163. In some embodiments, the variable d may represent the depth of penetration into the body of the subject—i.e. there is negligible attenuation prior to the radiation impinging on the body of the subject. The variables B and k may be operator-configurable, may be system parameters which may be determined by one or more suitable calibration procedures, may be system parameters which may be determined based on empirical testing and/or data and/or the like. Like the Fourier transform of the kernel function, the values of the attenuation factor (e.g. equation 3) may be pre-calculated and stored in a look up table or the like.

In some embodiments, beam configurations are contemplated which involve a plurality of beams 159 at a corresponding variety of locations along a trajectory which involves a 360° rotation of the radiation source with respect to the subject. In some embodiments, it is contemplated that the radiation source will move continuously with respect to the subject about the 360° trajectory. In such embodiments, the 360° trajectory can be approximated by a plurality of sample beams. For the purpose of this description, sample beams on a trajectory where it is contemplated that the radiation source will move continuously relative to the subject can be treated in the same manner as discrete beams 159.

Figure 14:
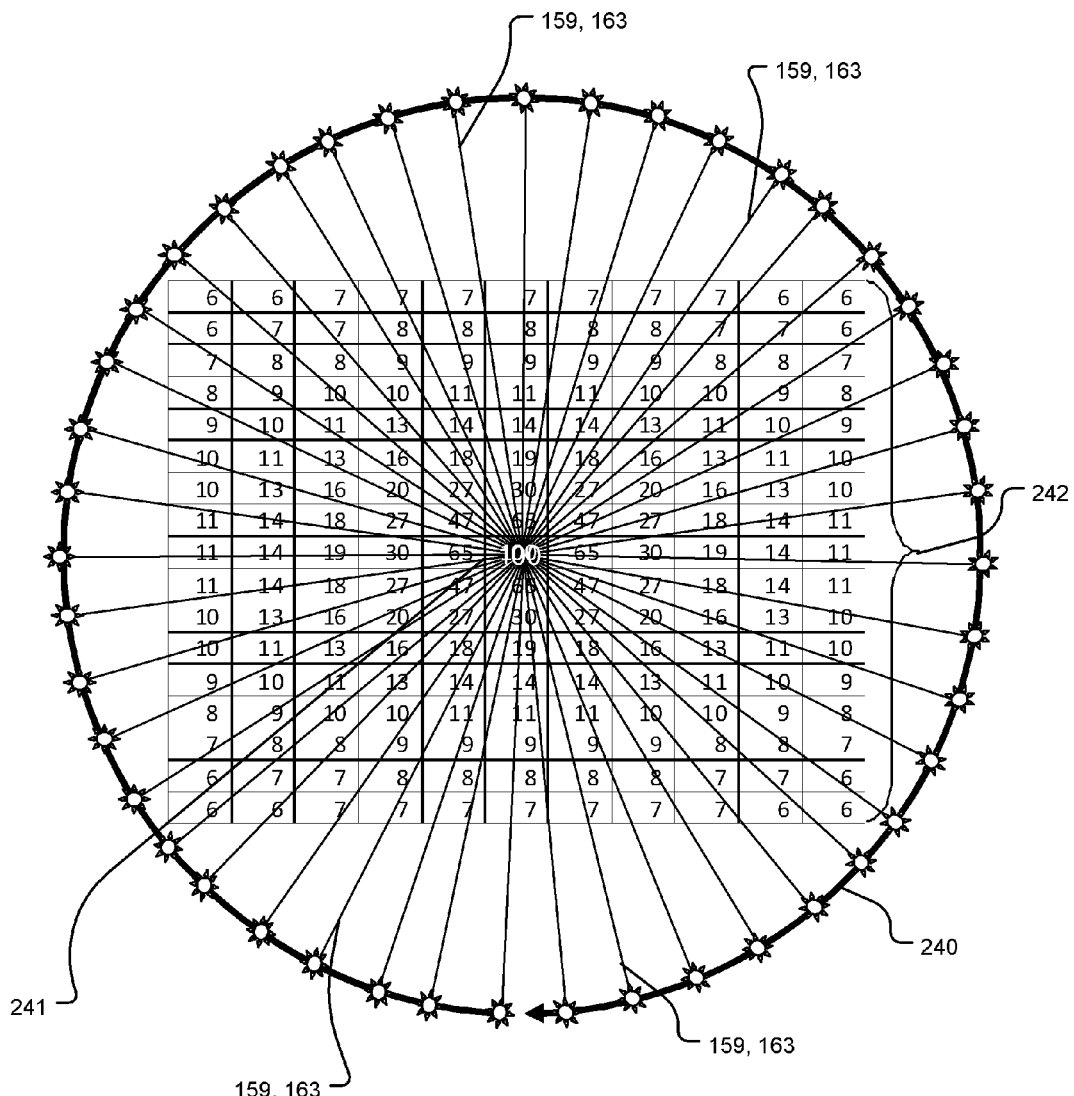
FIG. 14 schematically depicts a 360° trajectory, a plurality of beams at angularly evenly spaced locations around the trajectory, ray lines intersecting a centrally located voxel and a two-dimensional cross-section of a dose update grid estimated to be achievable by the plurality of beams.

FIG. 14 schematically depicts a 360° trajectory 240, a plurality of beams 159 at angularly evenly spaced locations around trajectory 240 and a two-dimensional cross-section of a dose update grid 242 estimated to be achievable by the plurality of beams 159. Beams 159 may be discrete beams or sample beams associated with a continuously moving radiation source. The achievable dose update grid 242 (having voxel dose contributions represented by the numbers in the boxes of the illustrated grid) has been scaled to a value of 100 at the dose modification voxel 241. The FIG. 14 dose update grid 242 may be obtained, for example, in accordance with block 60 of method 50 (FIG. 4D). The FIG. 14 dose update grid results from an equal intensity change to each of the beamlets associated with the ray lines 163 that intersect dose modification voxel 241.

Figure 15:
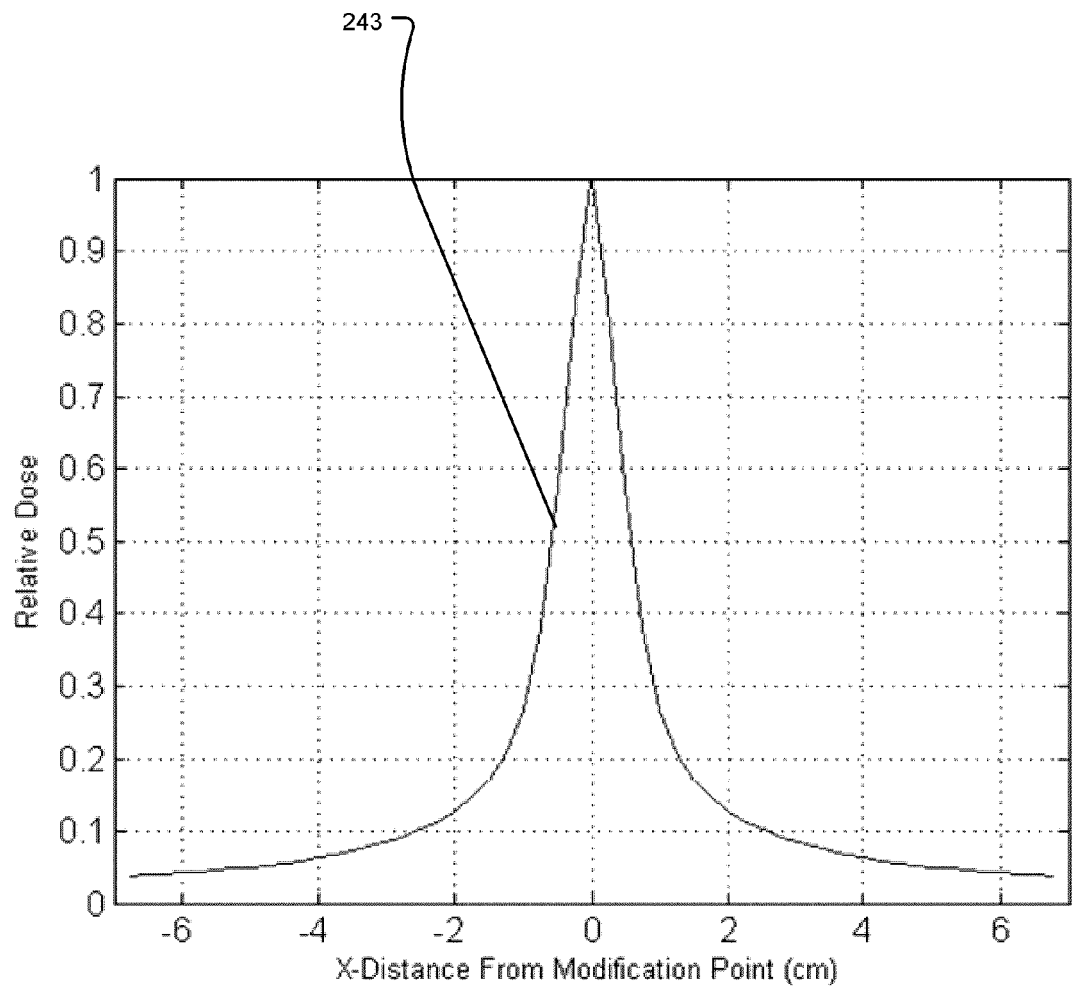
FIG. 15 depicts an example profile of the FIG. 14 achievable dose update grid intersects the dose modification voxel.

FIG. 15 depicts an example profile 243 of the FIG. 14 achievable dose update grid 242 that intersects dose modification voxel 241. The peak of the dose change depicted in example profile 243 occurs at the location of dose modification voxel 241 (x=0 in FIG. 15). Due to the 360° trajectory 240 and plurality of beams 159, the magnitude of the dose changes in areas surrounding dose modification voxel 241 decreases rapidly with distance from dose modification voxel 241. To achieve this property (i.e. where relatively small changes occur to the dose at locations away from particular dose modification voxels 241), it may be desirable that there be a relatively large number of beams 159 in 360° trajectory 240. As discussed above, in some embodiments, the radiation source moves continuously with respect to the subject and beams 159 are actually sample beams. In other embodiments, the angular separation between discrete beams 159 along the 360° trajectory 240 is less than 20°. In some embodiments, this angular separation is less than 15°.

Figure 16:
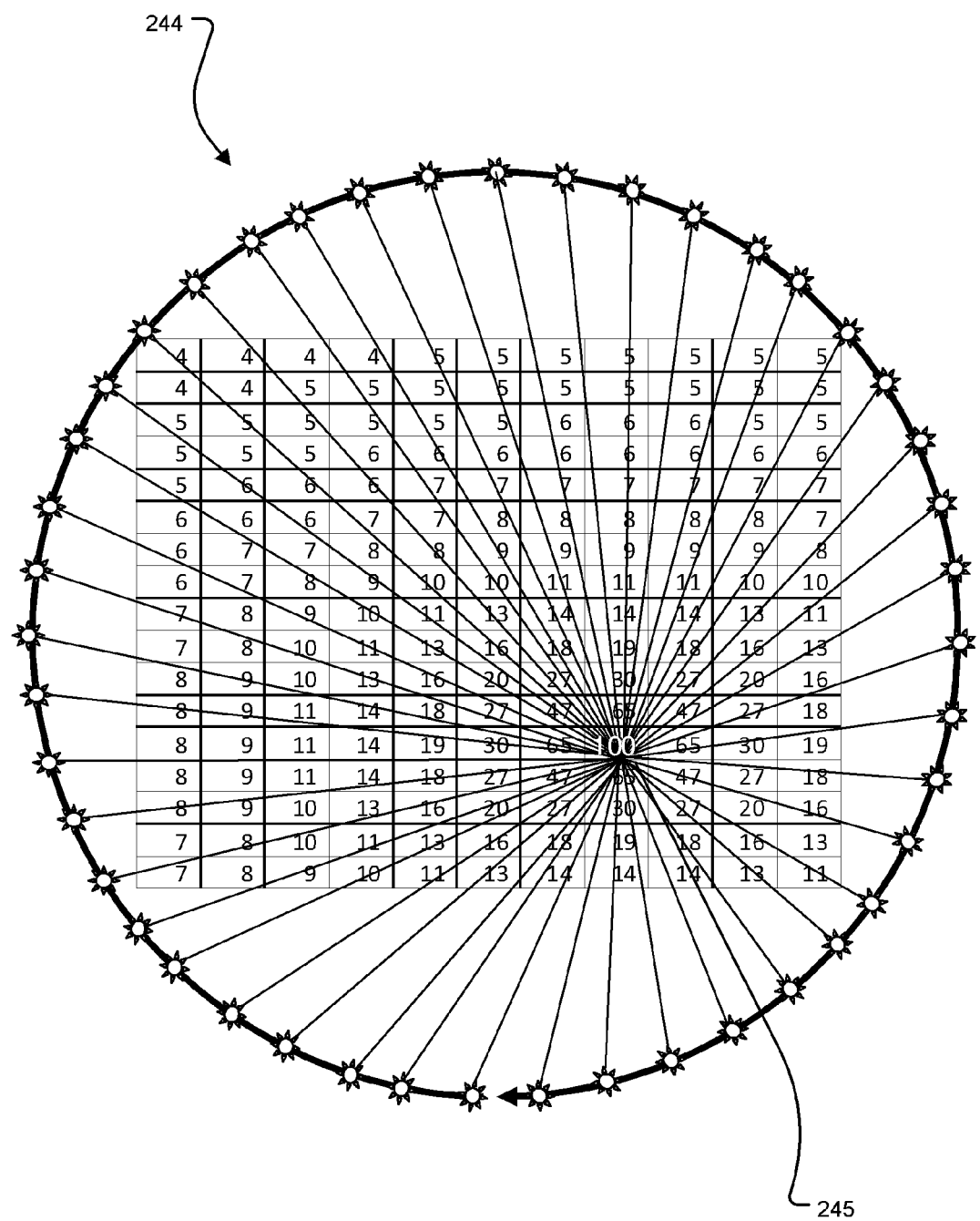
FIG. 16 depicts a dose update grid which is the same as the FIG. 14 dose update grid except that it has been translated to a different dose modification voxel.

An additional property of the 360° trajectory 240 and the corresponding dose update grid 242 is that the same dose update grid may be translated to any desired dose modification voxel. An example of this translatability is shown in FIG. 16 which depicts a dose update grid 244 which is the same as dose update grid 242 (FIG. 14) except that dose update grid 244 of FIG. 16 has been translated to a different dose modification voxel 245. The translatability of the dose update grid 242 for the 360° trajectory 240 may be permitted because every voxel in the plane of motion of the radiation source along trajectory 240 has a full 360° of ray lines which intersect the voxel and corresponding beamlets within beams 159. Some embodiments may achieve computational efficiency by determining the dose update grid 242 for a 360° trajectory 240 and storing the dose update grid 242 in accessible memory or the like (e.g. in a look up table). In this manner, the dose update grid 242 for a 360° trajectory 240 may be recalled from memory each time that it is used.

Figure 18A:
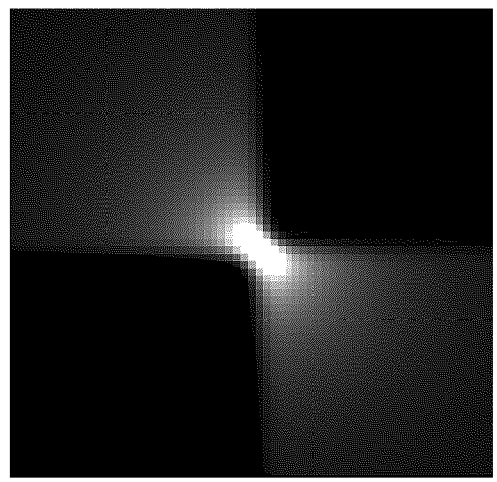
FIGS. 18A-18C schematically depict a number of radial modification dose (RMD) distributions and how various angular ranges of RMDs can be obtained by combining other angular ranges of RMDs.
Figure 18B:
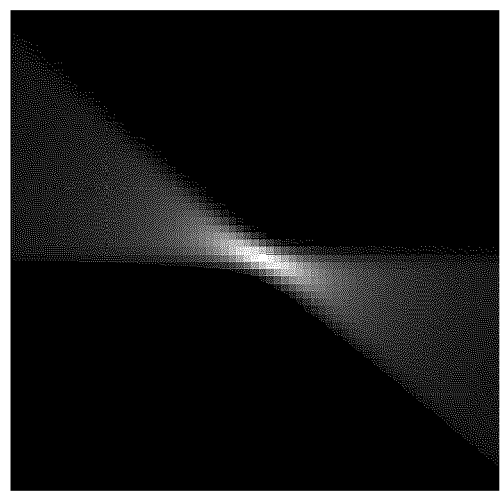
Figure 18C:
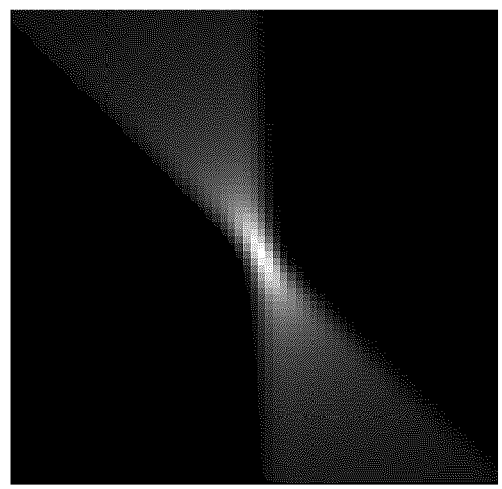

A 360° trajectory 240 is used as an example for illustration purposes. Beam configurations with other trajectories (e.g. other angular rotation ranges and/or other) motions may also be used. Furthermore, it may be desirable to use different angular ranges of beams when permitting manipulation of achievable dose (e.g. in block 142). For angular ranges of beams smaller than 360°, the corresponding angular range of ray lines 163 intersecting a dose distribution coordinate (e.g. a dose modification voxel) will be reduced. In some embodiments, dose update grids for alternative motion ranges may also be pre-calculated and stored (e.g. in a look up table in an accessible memory) for subsequent retrieval. A library of dose update grids referred to as radial modification dose (RMD) distributions may be stored in accessible memory. Such a library of RMDs may include RMDs for N incremental motion ranges from 0°-N°, for example, where N has incremental values going from 0°-360°. Specific angular ranges of beams may be determined by subtracting two dose modification distributions stored in the library. For example:

$$RMD(\theta \Rightarrow \phi) = RMD(0 \Rightarrow \phi) - RMD(0 \Rightarrow \theta) \quad (4)$$

Where $\theta \Rightarrow \phi$ indicates an angular range of beams going from angle $\theta$ to angle $\phi$. Using a subtraction operation like that of equation (4) reduces the number of actual RMDs that must be stored in memory. A graphical example is shown in FIGS. 18A, 18B, 18C, where RMD dose distributions are displayed as pixel map images, in which brighter pixels indicate higher doses. FIG. 18A represents a RMD for the angular range 0°-90° and FIG. 18B represents a RMD for 0°-45°. Both the FIGS. 18A and 18B RMDs may be stored in accessible memory. Assuming that it is desired to determine a RMD for the angular range 45°-90°, then the 0°-45° RMD (FIG. 18B) may be subtracted from the 0°-90° RMD (FIG. 18A) to yield the 45°-90° RMD shown in the representation of FIG. 18C.

Figure 17:
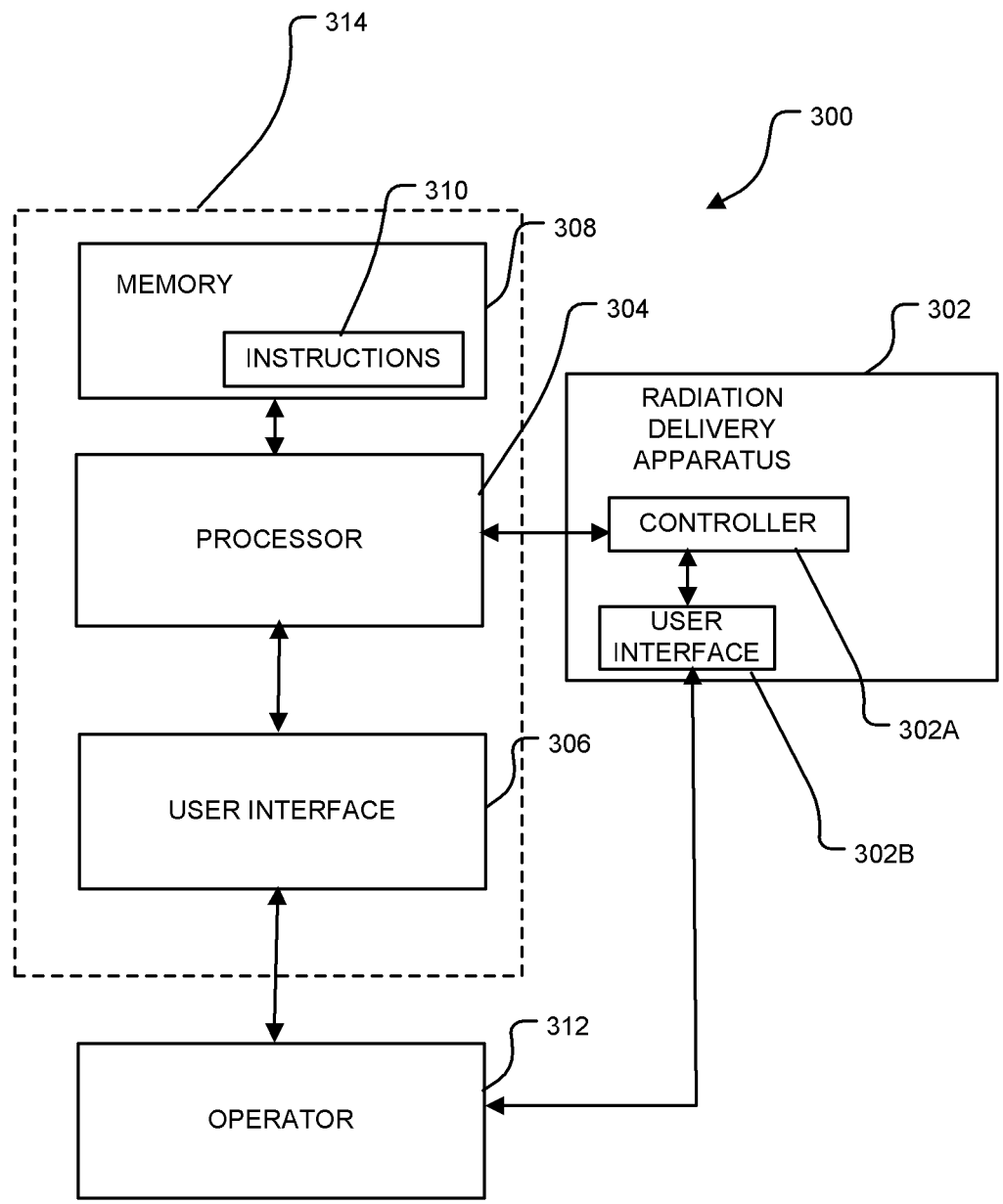
FIG. 17 is a schematic depiction of a system for estimation and manipulation of estimated dose according to a particular embodiment of the invention.

FIG. 17 schematically illustrates a system 300 according to a particular embodiment of the invention. System 300 (or portions thereof) may be used to perform some or any of the methods described above. System 300 comprises a radiation delivery apparatus 302 which may be similar to any of the radiation delivery apparatus described herein. Operator 312 may interact with radiation delivery apparatus 302 via user interface 302B which may include both hardware components and software components. In the illustrated embodiment, the operation of radiation delivery apparatus 302 is controlled by a controller 302A. In the illustrated embodiment, controller 302A receives radiation delivery parameters from an external processor 304. Processor 304 may comprise any suitable computer or digital processing unit(s). Processor 304 may carry out computer readable software instructions. Processor 304 may be in communication with radiation delivery apparatus 302 using any suitable communication hardware and/or software including network communication hardware and/or software. An operator 312 may interact with processor 304 using a suitable user interface 306 which may include both hardware components and software components.

Processor 304 of the illustrated embodiment has access to a computer-readable memory 308 which may house software instructions 310. In other embodiments, processor 304 may obtain instructions 310 from one or more other sources. When executed by processor 304, software instructions 310 may cause processor 304 to perform one of more of the methods described herein (e.g. radiation delivery method 16 (FIG. 4A), method 18 for generation and manipulation of achievable dose (FIG. 4B), dose estimation update method 50 (FIG. 4D), rapid dose estimation 70 (FIG. 13) and/or the like). In the illustrated embodiment, processor 304, user interface 306 and memory 308 are part of a computer system 314, although this is not necessary. In other embodiments, these components (or parts thereof) may be separately implemented.

In still other embodiments, one or more of the methods described herein may be performed by controller 302A (or some other suitable processor) that is part of radiation delivery apparatus 302. In such embodiments, radiation delivery apparatus 302 may comprise (or otherwise have access to) suitable memory which may comprise suitable computer software instructions.

EXAMPLES

The examples set out below represent non-limiting examples of methods, systems and various features of methods and systems according to various embodiments. These non-limiting examples are for illustrative purposes only and are not intended to represent limiting features unless otherwise claimed below.

Pseudocode Example

Figure 19A:
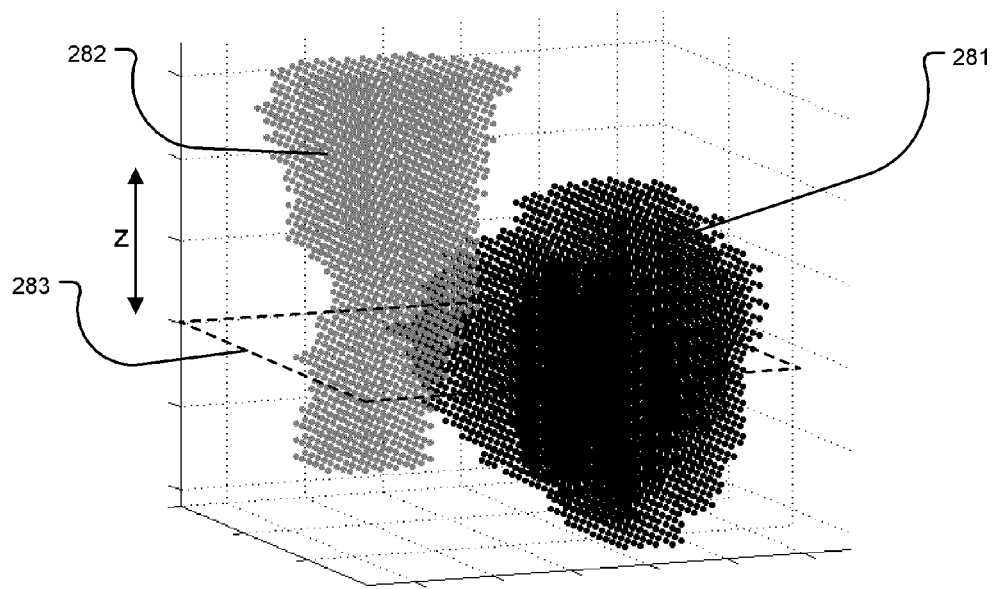
FIG. 19A is a three-dimensional rendering showing a target structure and a healthy tissue structure.
Figure 19B:
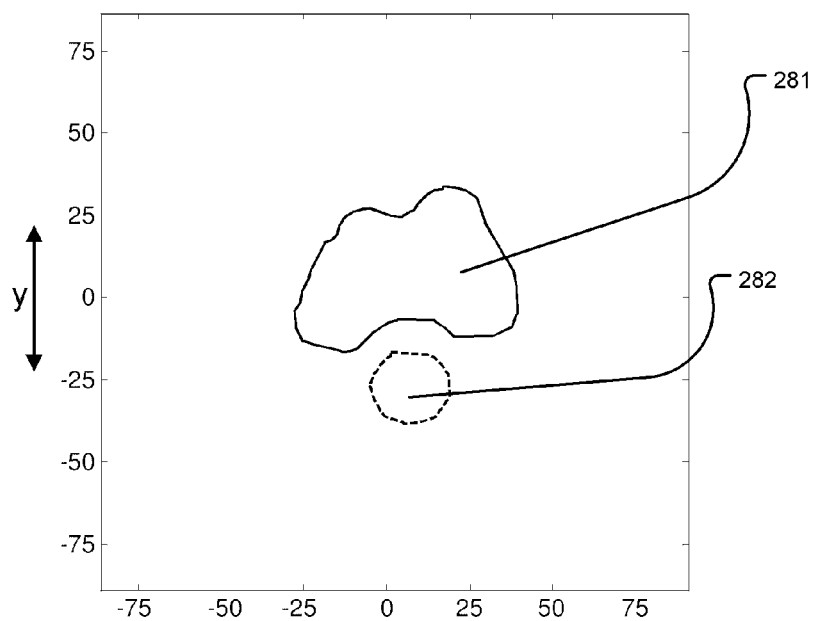
FIG. 19B is a cross-sectional view bisecting (and showing outlines of) the target structure and healthy tissue structure of FIG. 19A.

Setup Initialization
Import subject image and segmented tissue structure information (e.g. tumor target, healthy tissue structures (e.g. organs), other tissue of interest, target prescription)
Select dose estimate kernel (e.g. point spread function (PSF)) based on beam energy and associated scattering characteristic(s)
Calculate Fast Fourier Transform (FFT) of PSF and store in accessible memory for later use
Create voxel matrix (calculation grid) overlaid with image data from subject including tissue structure information
Identify voxels located within any structure(s) of interest
   identify voxels partially within a structure (e.g. at the edge of the structure) and assign partial volume values (e.g. in a range of 0-1) to those voxels for the purpose of calculating dose quality metrics based on such voxels
Select beam configuration (e.g. number, location and direction of beams)
   Desired beam configuration may include a number of fixed beams (e.g. 5 to 9 beams or other numbers of fixed beams)
   If desired beam configuration involves continuously moving beams, then a number of beam samples (e.g. 10 or more beam samples) along the trajectory may be used to represent dynamic source motion
Initialize beamlet intensities
Calculate estimated dose distribution resulting from initial beamlet intensities
Calculate initial dose volume histogram (DVH) (and/or other initial dose quality metric(s))
Display initial DVH(s) and/or initial dose distribution overlaid with image data from subject including tissue structure information
   dose may be represented via cross sectional view(s) of the image data
      dose can be represented as a color wash
      dose can be represented as an iso-line plot (line contours of constant dose)
      dose can be represented using any other suitable display technique
   three-dimensional dose display (so-called "dose cloud" displays) could additionally or alternatively be used
Beamlet Initialization
Create two-dimensional beamlet matrix for each beam
For each target structure:
   Target structure is projected onto the beamlet matrix
   A margin may be added to the projection to ensure proper coverage of the target structure by the resulting dose distribution
   Assign an intensity value to beamlets corresponding to target structure.
Such intensity value may be correlated with (e.g. proportional to) the prescription dose for the target structure
Optional:
   For target structures that overlap in a given beam projection, weight the beamlet intensities in the overlapping area with the overlapping target structure that has the highest prescription dose; or
   For target structures that overlap in a given beam projection, weight the beamlet intensities in the overlapping area with the overlapping target that has the lowest prescription dose Rapid Estimation of Achievable Dose Distribution
Estimate dose contribution—For each beam:
   Convolve beamlet intensity matrix by the dose estimate kernel (e.g. PSF)
      Perform convolution by: determining the FFT of the beamlet matrix; multiplying by the pre-calculated FFT of the dose estimate kernel; and determining the Inverse FFT of the result
Determine intersection of ray lines from beamlet matrix with voxels—For each voxel where the dose has not been previously determined:
   For each beam:
      Determine the location where any ray line passing through the voxel intersects with the beamlet matrix
      Store the beamlet intersection location in accessible memory for use in subsequent dose calculations (so that the beamlet intersection location only needs to be determined once)
      Achievable dose estimation may be limited to voxels of interest. For example:
         For DVH calculation, achievable dose estimation may be limited to voxels within target and healthy tissue structure(s)
         In the case where a dose plane cross section is being displayed, achievable dose estimation may be limited to voxels in that plane
Calculate total dose—For each voxel:
   Extract the dose contribution—For each beam:
      Extract the convolved intensity value from the convolved intensity distribution at the location of the previously determined beamlet matrix intersection
   Sum the contribution from each beam
Permit Dose Volume Histogram Manipulation
Operator selects a point on a DVH curve of a particular structure and requests a change of the curve shape at that point
   Identify the dose and volume coordinate values of the selected point (D_selected, V_selected)
   The request may be communicated by selecting the DVH with a mouse or similar computer pointing device click and then moving the mouse or similar computer pointing device
      movement left and/or down indicates may indicate a dose reduction (desired dose change is negative)
      movement right and/or up may indicate a dose increase (desired dose change is positive)
   Determining a magnitude of the desired dose change may involve, for example:
      A fraction of the D_selected value
      A fraction of the maximum dose for that structure
      A fraction of a prescription dose assigned to that structure
      A fraction of the maximum prescription dose assigned to all structures
      A fraction correlated with (e.g. proportional to) the amount of mouse or similar computer pointing device movement
      A quantity set by the operator
      A fixed quantity which may be an operator-configurable parameter or may be a "hard coded" constant
      A combination of the above
For the selected structure, voxels having dose values close to D_selected may be identified as dose modification voxels Voxels may be identified as dose modification voxels if the voxels have values falling within D_selected+/−Δ
  Δ may be a fixed value (which may be operator-selectable) or a fraction of D_selected (which may be an operator-selectable fraction)
If no voxels are identified to be dose modification voxels then Δ may be expanded and voxels may be re-identified
  This process repeats until at least one voxel is identified as a dose modification voxel
If a large number of voxels (e.g. all voxels for that structure or a number of voxels greater than a threshold number or a threshold percentage of the voxels in a structure) are identified to be dose modification voxels, then A may be reduced and voxels may be re-identified
In some embodiments, all voxels inside the structure for which the DVH is changed may be identified as dose modification voxels
Optional: identification of secondary dose modification voxels in marginal region around primary dose modification voxels and assignment of suitable magnitude of dose modification to secondary dose modification voxels
Dose modification is performed for voxels identified as dose modification voxels (see Dose Modification below)
Once Dose Modification is performed, DVH is re-calculated based on new estimated dose
Check whether any dose restrictions are violated (see Dose Manipulation Under Dose Restrictions)
Display is updated with new DVH
Dose Modification
For each voxel identified to be a dose modification voxel (Vox_identified) and for each beam:
  Determine the location(s) where ray line(s) passing through Vox_identified intersect with the beamlet matrix
  Modify intensity values of beamlet(s) at intersection point(s) (dose-change beamlets) using a default quantity
    The default quantity may be correlated with (e.g. proportional to) the magnitude of the desired dose change and may also depend on the number of dose-change beamlets who ray lines intersect Vox_identified
  Optional: identify and determine intensity value adjustment for secondary dose-change beamlets in a marginal region around primary dose-change beamlets
Modified beamlets are evaluated for possible intensity restriction violations. By way of non-limiting example:
  Intensity values that are less than a minimum threshold
    Corrected by increasing violating beamlet intensities to minimum threshold
  Intensity values greater than a maximum threshold
    Corrected by decreasing violating beamlet intensities to maximum threshold
  Variations in intensity over the two dimensional extent of the beamlet matrix may also be limited (e.g. a maximum variation of a fixed percentage from one beamlet to an adjacent beamlet)
    Corrected by increasing or decreasing the intensities of modified beamlets so that variation restriction is no longer violated
Dose is estimated at voxels for all beams using Rapid Estimation of Achievable Dose Distribution
  Dose may be calculated for only a subset of voxels. For example:
    Voxels of the selected structure only
    Voxels of all structures
    Voxels of all structures plus currently displayed cross sectional plane
  Estimated dose for each dose modification voxel (Vox_identified) is compared to dose requested by operator:
    Determine difference between the mean estimated dose and mean operator-requested dose for all dose modification voxels Vox_identified
    Rescale magnitude of intensity modification for all dose-change beamlets is rescaled so that mean dose for each dose modification voxel (Vox_identified) is equal to mean operator-requested dose requested by operator unless the rescaling of the dose-change beamlets results in a violation of the beamlet intensity restrictions
Dose Manipulation Under Dose Restrictions
Restrictions on the shape of DVH curves (or other restrictions on the dose distribution itself or on other dose quality metrics) may be designated by the operator or may be otherwise incorporated into the procedure (e.g. as global parameters of the system/method). For example:
  No voxels within a structure can be below a specified dose threshold
  No voxels within a structure can exceed a specified dose threshold
  A specified percentage of volume of a structure cannot exceed a specified dose threshold
  A specified percentage of volume of a structure cannot exceed a specified dose threshold
When a dose manipulation is performed (through DVH or otherwise) the dose distribution is evaluated for potential dose restriction violations
Violations are detected by comparing the estimated dose distribution and/or dose quality metrics (e.g. DVH) with the dose restrictions
  Voxels contributing to the violation are identified
  The magnitude of dose change required for each violating voxel to satisfy the restriction is calculated
  Perform Dose Modification (see above) using the violating voxels and voxel dose change requirements as inputs
  Repeat as necessary until there are no further dose restriction violations Example Application The following non-limiting example is meant to provide further understanding of how various aspects and features of the invention could be used in practice. FIG. 19A is a three-dimensional rendering of a target structure 281 and healthy tissue structure 282 and FIG. 19B is a cross-sectional view bisecting (and showing outlines of) target structure 281 and healthy tissue structure 282 along the plane 283. FIG. 19B shows the x and y axes scales in millimeters.

Figure 20A:
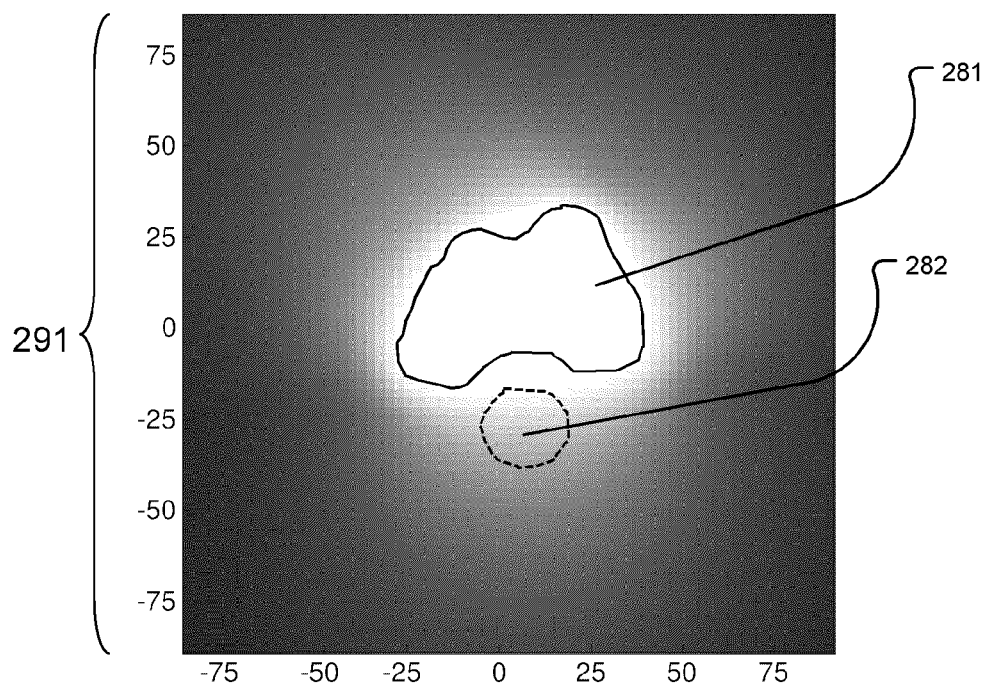
FIG. 20A shows a representation of a cross-section of an initial estimated dose distribution for the FIG. 19A tissue structures.
Figure 20B:
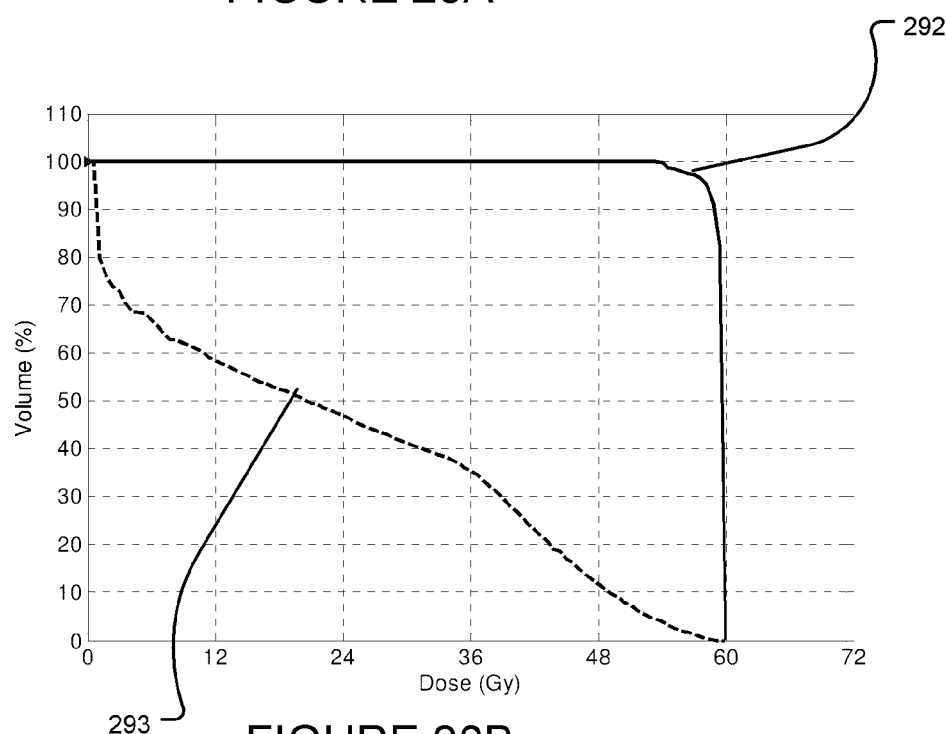
FIG. 20B shows an initial DVH for the FIG. 19A tissue structures.

The beam configuration used in this particular example comprises a 360° degree rotation of the radiation source with respect to the subject. Such a beam configuration could be implemented using the radiation delivery apparatus of FIG. 1 or 2, for example. In this example, it is assume that the radiation source moves in the x-y plane of FIGS. 19A, 19B. The initial estimated dose (e.g. block 46) is generated using 180 beams distributed along the path of the radiation source. The initial estimate of the dose distribution is determined using initial intensity distributions (e.g. block 44) wherein the initial beamlet intensities are proportional to the target prescription dose for ray lines that project through target structure 281 and zero otherwise. In this example, the target prescription dose is 60 Gy. The initial dose is estimated using the convolution based rapid dose estimation technique described above, with the dose estimate kernel according to equation (1) and using the inverse Fourier transform method of equation (2). At each voxel, the total estimated dose is the sum of dose contributions from each beam to that voxel. FIG. 20A shows a representation of a cross-section 291 of the initial estimated dose distribution for the FIG. 19A target tissue structure 281 and healthy tissue structure 282. FIG. 20B shows the DVH for the full three-dimensional target structure 292 and healthy tissue structure 293. The FIG. 20A dose distribution 291 is depicted as a grayscale pixel map, with lighter pixels indicating higher dose. The initial dose estimate 291 is fairly uniform in the volume of target structure 281 with the healthy tissue structure 282 receiving substantial dose in the region adjacent to target structure 281.

Figure 21A:
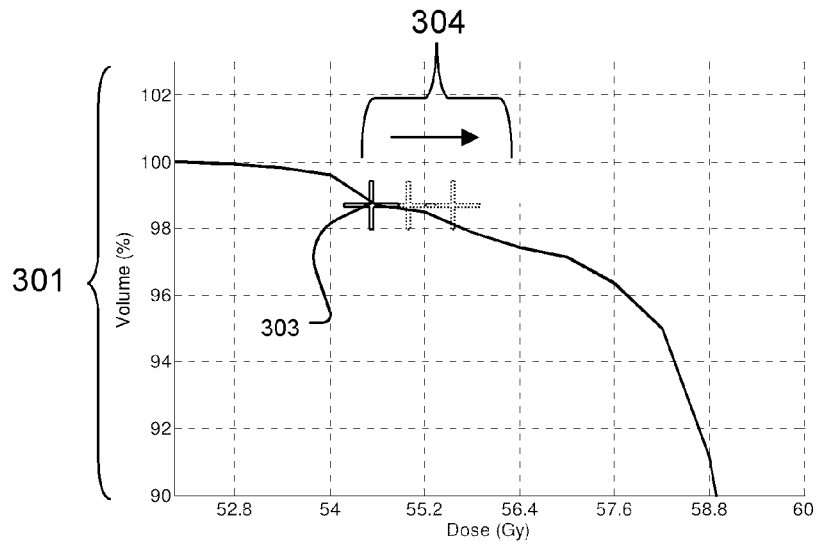
FIG. 21A shows a magnified portion of the FIG. 20B target structure DVH and operator manipulation thereof.
Figure 21B:
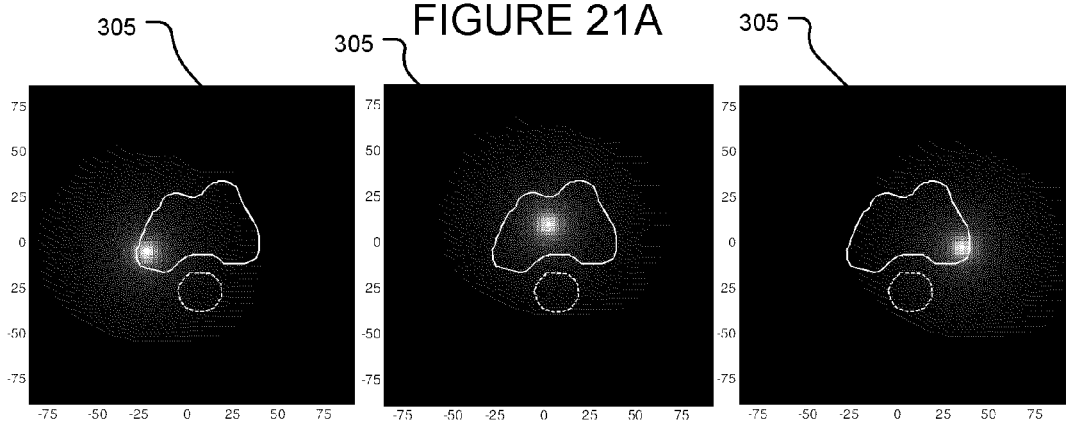
FIG. 21B shows a number of dose modification distributions resulting from the FIG. 21A operator manipulations.
Figure 21C:
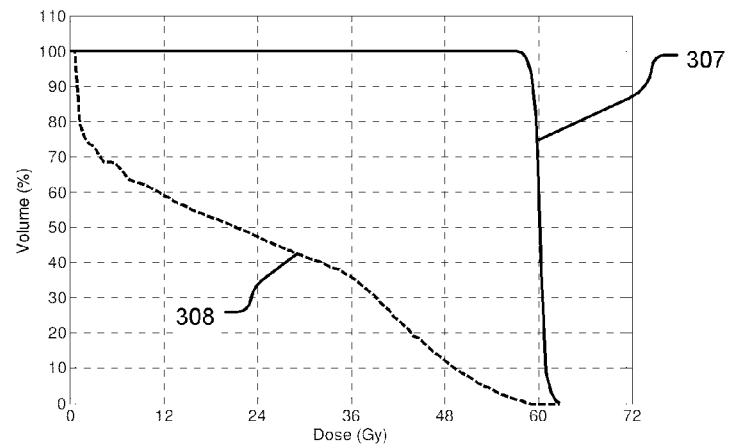
FIG. 21C shows an updated dose distribution and updated target and healthy structure DVHs after the FIG. 21A manipulation.

Once the initial dose estimate is established, manipulation of the estimated dose distribution may be permitted (e.g. by an operator). The operator may desire to establish adequate volumetric coverage of target structure 281 with the prescription dose. This may be accomplished by increasing the minimum dose to target tissue structure 281 through manipulation of the DVH. FIGS. 21A, 21B and 21C show an example of increasing the minimum dose to target structure 281 through DVH manipulation. FIG. 21A shows a magnified portion 301 of the FIG. 19B DVH plot 292. The operator may select the DVH curve near a low dose point 303 on the curve 301 (e.g. using the computer mouse or similar computer pointing device), depress the mouse button, and then translate curve 301 to the left (towards lower dose) or to the right (towards higher dose). In this example, the operator increases the dose by moving the selected point 303 on DVH curve 301 to the right as shown at 304. When the operator moves the DVH curve in this manner, the dose modification voxels (and corresponding dose modification magnitudes) are determined and a dose modification is applied to those dose modification voxels. In this example, the FIG. 21A manipulation corresponds to three dose modification voxels. When the dose modification is applied to these three dose modification, voxels it is determined that no intensity limits will be violated. FIG. 21B shows examples of three dose modification distributions 305 resulting from the FIG. 21A dose modification request communicated by the operator (i.e. from the three dose modification voxels). In the FIG. 21B representations, lighter grayscale indicates higher dose. It may be observed that each modification 305 is well localized to specific areas of the dose distribution. FIG. 21C shows an updated dose distribution and correspondingly updated DVHs for the target structure 307 and healthy tissue structure 308. The updated target structure DVH 307 of FIG. 21C shows that the minimum dose to the target structure 281 is higher than it was preceding the modification (see DVH 292 of FIG. 20B). Also, it may be observed that healthy tissue DVH 308 has not changed substantially (compare to healthy tissue structure DVH 293 of FIG. 20B), which is a result of the changes being localized to target structure 281 during dose modification.

Figure 22A:
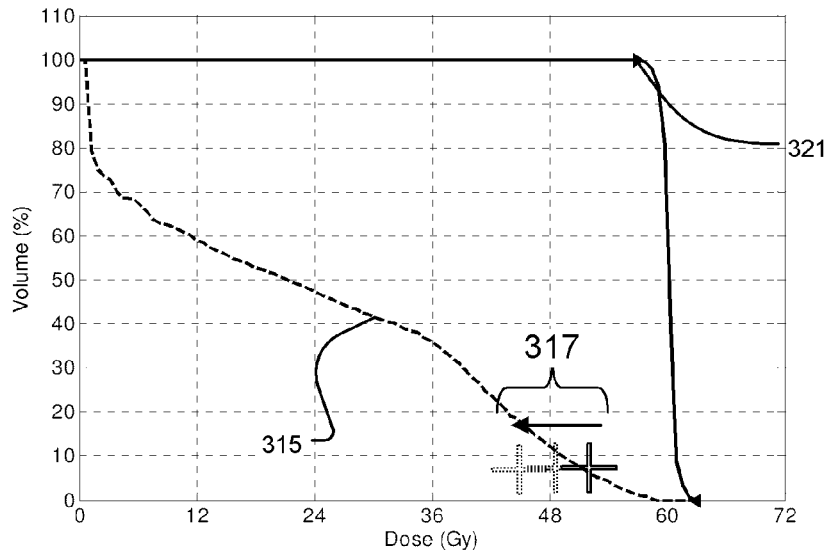
FIG. 22A shows operator manipulation of the FIG. 20B healthy tissue DVH.
Figure 22B:
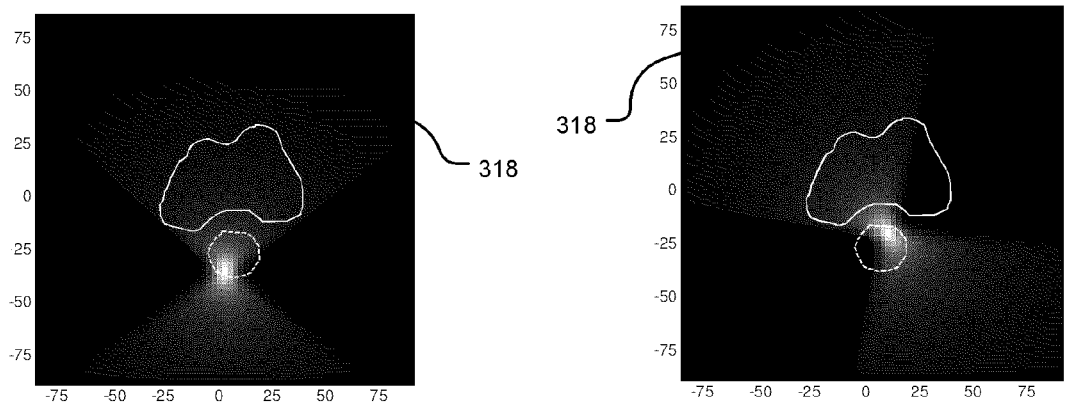
FIG. 22B shows a number of dose modification distributions resulting from the FIG. 22A operator manipulations.
Figure 22C:
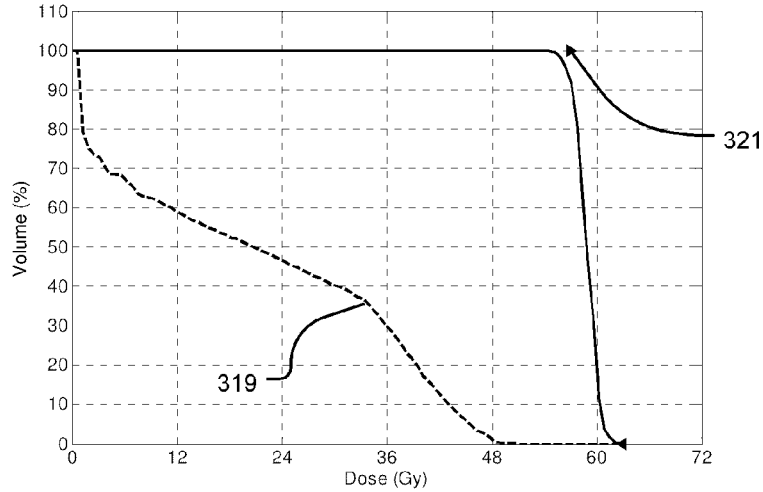
FIG. 22C shows updated target and healthy structure DVHs after the FIG. 22A manipulation.

Now that the operator has established an acceptable dose distribution for target structure 281, it may be desirable to place restrictions on DVH manipulation so that the acceptable dose distribution is maintained during further dose modification. For example, such a restriction could be that 100% of the target structure 281 should receive 57 Gy and 0% of the target structure 281 should receive more than 63 Gy. The operator may then proceed with modifying the DVH 315 corresponding to healthy tissue structure 282 by selecting a point on DVH 315 and dragging the mouse or similar computer pointing device to the left 317 (for dose reduction). Once the dose modification voxels corresponding to this desired DVH modification have been determined, a dose modification is applied to each dose modification voxel. In this case restrictions on the intensity changes necessitate the use of a smaller number of beamlets. FIG. 22B shows corresponding dose modification distributions 318 which may be different from those of FIG. 21B due to the smaller number of beamlets used. Note that the dose modification distributions 318 are well localized inside the healthy tissue structure 282. FIG. 22C shows the updated DVH 319. FIG. 22C shows that the dose to healthy tissue structure 282 has been reduced as desired.

Figure 23A:
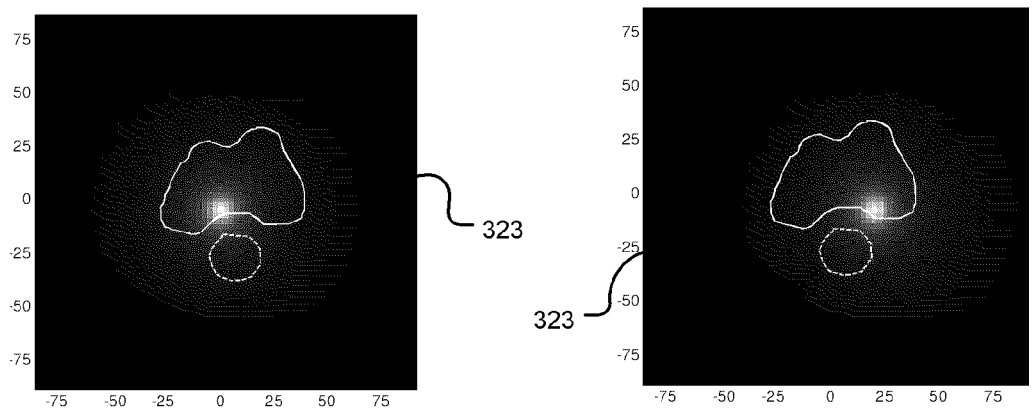
FIG. 23A shows two example dose modification distributions used to correct the FIG. 22C violation of the constraint on the target dose distribution.
Figure 23B:
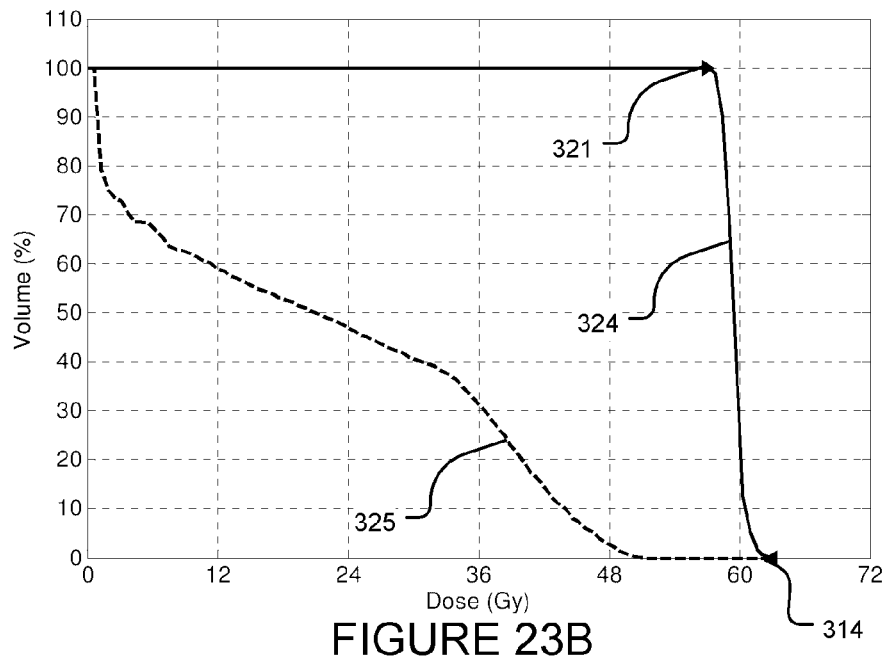
FIG. 23B shows target structure DVH after application of the FIG. 23A dose modification distributions.
Figure 23C:
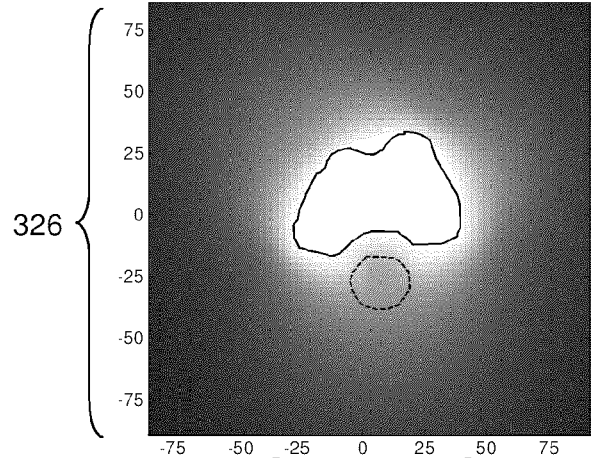
FIG. 23C shows a representation of the resultant cross-sectional dose distribution.

With the healthy tissue dose reduction illustrated in FIG. 22C, the restriction 321 placed on the minimum dose for target tissue structure 281 is violated (see FIG. 22C). A corrective dose modification may be automatically applied to bring the target structure DVH back within the constraint 321. The dose modification voxels where the dose distribution causes the violation of the DVH constraint 321 are determined and dose modifications are applied at those dose modification voxels. FIG. 23A shows two example dose modification distributions 323 used to correct the violation of constraint 321 on the target dose distribution. FIG. 23A shows that in this case the dose modification is applied at the edge of target structure 281 close to healthy tissue structure 282 where the FIG. 22 dose decrease was applied. Again the dose modification distributions are well localized so that areas surrounding the dose modification voxels are not substantially impacted. FIG. 23B shows target structure DVH 324 after application of the FIG. 23A dose modification 323 and how target structure DVH 324 is now within the restrictions (321 and 314). The healthy tissue structure DVH 325 has changed only slightly from that of FIG. 22C due to the dose changes being localized primarily within the target structure 281. FIG. 23C shows a representation of the resultant cross-sectional dose distribution 326 which shows a reduction in dose to the healthy tissue structure compared to that of FIG. 21C, as was originally desired by the operator.

Figure 24A:
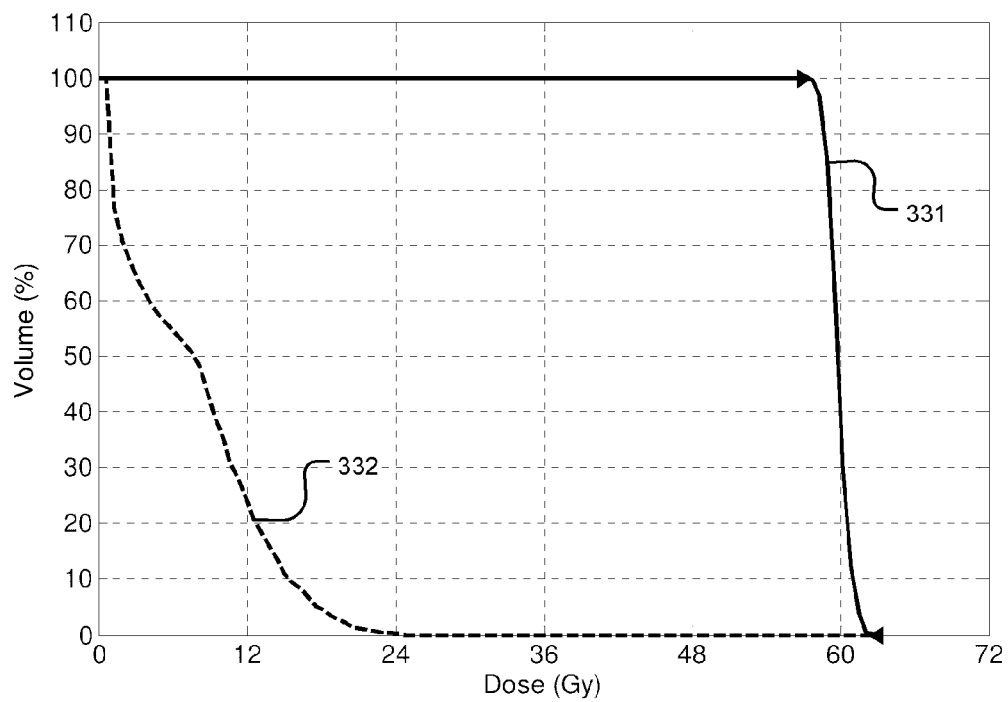
FIG. 24A shows DVHs for target and healthy tissue structures at the conclusion of a series of dose modifications by the operator.
Figure 24B:
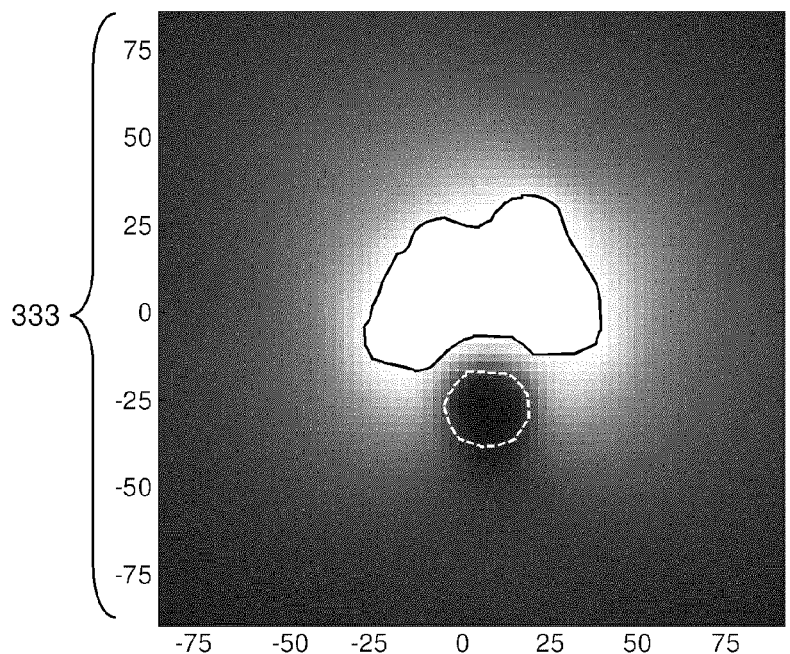
FIG. 24B shows a cross-sectional estimated dose distribution corresponding to the DVHs of FIG. 24A.

Further dose modifications may be imposed by the operator by repeating in a similar fashion the process described above. For example, further reductions in the healthy tissue structure dose may be applied under the constraints 321 and 314 (FIG. 23B). Eventually an equilibrium will be reached where further reduction in healthy tissue structure dose cannot be achieved without violating the restrictions on the target dose. FIG. 24A shows the DVH for the target 331 and healthy tissue structure 332 at the end result of a series of dose modifications by the operator. FIG. 24B shows the corresponding cross-sectional estimated dose distribution 333 corresponding to these modifications. The DVH 332 and estimated cross-sectional dose distribution 333 for the healthy tissue structure 282 have been reduced considerably as compare to the initial DVH 293 (FIG. 20B) and dose distribution 291 (FIG. 20A). A high uniform dose is maintained in the target as seen in the final target DVH 331 (FIG. 24A) and cross-sectional dose distribution 333 (FIG. 24B).

After the dose manipulation is complete the radiation delivery parameters for the beam configuration may be determined. The radiation delivery parameters may then be transferred to the control system and computer of the radiation delivery apparatus. The radiation may then be delivered to the subject, thereby delivering a dose distribution in the subject substantially similar to that derived from the dose manipulation.

\* \* \*

Embodiments of the present invention include various operations, which are described herein. These operations may be performed by hardware components, software, firmware, or a combination thereof.

Certain embodiments may be implemented as a computer program product that may include instructions stored on a machine-readable medium. These instructions may be used to program a general-purpose or special-purpose processor to perform the described operations. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

Computer processing components used in implementation of various embodiments of the invention include one or more general-purpose processing devices such as a microprocessor or central processing unit, a controller, graphical processing unit (GPU), cell computer, or the like. Alternatively, such digital processing components may include one or more special-purpose processing devices such as a digital signal processor (DSP), an application specific integrated circuit (ASIC), a field programmable gate array (FPGA), or the like. In particular embodiments, for example, the digital processing device may be a network processor having multiple processors including a core unit and multiple microengines. Additionally, the digital processing device may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in light of the foregoing disclosure, many alterations and modifications are possible in the practice of this invention without departing from the spirit or scope thereof. For example:

The above-described embodiments describe several features which may be characteristics of each beam 159. By way of non-limiting example, the procedures of block 72-78 for each loop of method 70 (FIG. 13) are performed for each beam 159 and FIG. 12 shows a number of beams 159. In some embodiments, radiation delivery may involve continuous movement of the radiation source with respect to the subject over a given trajectory. In such embodiments, the trajectory of movement of the radiation source with respect to the subject may be described by a number of discrete sample beams from along trajectory. Such sample beams may be sampled sufficiently closely to one another such that the sum of the dose contributions of the sample beams is representative of the sum of the dose contributions from the continuously moving radiation source. Such sample beams may be used in a manner similar to that described herein for conventional discrete beams and unless specifically described as being discrete, any references to beam(s) herein should be understood to include sample beams.

Referring to FIG. 4A, it will be appreciated by those skilled in the art that the number of beam 159 is not required to be the same in blocks 142 and 143. For example, it can be computationally more efficient to have a relatively small number of beams 159 when permitting manipulation of the estimated dose in block 142. Then, in block 143, a larger number of beams 159 can be used to accurately determine the radiation delivery parameters. In some embodiments, the number and/or location of beams 159 may be one of the variables that is permitted to change in a block 143 optimization process.

The discussion presented above suggests that there is a one to one relationship between beamlets 164 and ray lines 163—i.e. each beamlet 164 has a corresponding ray line 163. Such ray lines 163 may pass through the center of their corresponding beamlets 164. Using such ray lines 163, a relationship can be established between particular beamlets and particular voxels—e.g. dose-change beamlets can be identified as those beamlets that have corresponding ray lines that project through a dose modification voxel (see discussion of block 221 above). It will be appreciated, however, that beamlets actually have a two-dimensional shape. In some embodiments, it may be desirable to model this two dimensional beamlet shape by accounting for the impact of a beamlet on voxels other than merely the particular voxels through which its corresponding ray line passes. For example, in some rapid dose estimation embodiments (e.g. in some embodiments of method 70 of FIG. 13) the ray lines associated with particular convolved intensity values may impinge on particular voxels at locations away from the centers of the particular voxels and the dose contributions from those convolved intensity values may be fractionally divided as between the particular voxels and one or more of their neighboring voxels. The fractional division of dose contributions between the particular voxels and neighboring voxels may depend on the location where the ray line impinges on the particular voxels. For example, most of the fractional dose contribution may be added to a particular voxel intersected by a ray line and the remaining dose contribution may be divided between the neighboring voxels, with neighboring voxels relatively close to the location of intersection receiving a greater dose contribution than neighboring voxels that are relatively far from the location of intersection.

In some rapid dose estimation embodiments (e.g. in some embodiments of method 70 of FIG. 13), it may be the case that multiple ray lines 163 from a single beam of convolved intensities impinge on a single voxel. In such cases, the dose contribution added to the voxel may be some form of average or interpolation of the dose contributions that would be predicted by each of the individual convolved intensity values.

The discussion presented above suggests that there is a one to one relationship between beamlets 164 and ray lines 163—i.e. each beamlet 164 has a corresponding ray line 163 which may pass through its center. However, in other embodiments, for each beam, ray lines could additionally or alternatively have a one to one relationship with voxels—i.e. each voxel could have a corresponding ray line that extends from the center of the voxel toward the radiation source location for that particular beam. In such embodiments, the block 221 (FIG. 4B) process for identification of dose-change beamlets could involve tracing rays from the block 220 dose modification voxels onto the two-dimensional grids 162 of beamlets 164—i.e. dose-change beamlets could be identified as those through which a ray line projects. In some embodiments, it may be desirable to model the three-dimensional voxel shape by accounting for the impact of a voxel on beamlets other than merely the particular beamlets through which its corresponding ray line passes. For example, in some embodiments of method 18 (FIG. 4B), the ray lines associated with particular dose modification voxels may impinge on particular beamlets at locations away from the centers of the particular beamlets and the block 223 intensity value adjustments may be fractionally divided as between the particular beamlets and one or more of their neighboring beamlets. The fractional division of intensity adjustments between the particular beamlets and neighboring beamlets may depend on the location where the ray line impinges on the particular beamlets. For example, most of the fractional intensity value adjustment may be made to a particular beamlet intersected by a ray line and the remaining intensity value adjustment may be divided between the neighboring beamlets, with neighboring beamlets relatively close to the location of intersection receiving a greater fraction of the intensity value adjustment than neighboring beamlets that are relatively far from the location of intersection.

In some embodiments, ray lines for each beam may have a one to one association with voxels and ray lines may extend from the center of voxels to the radiation source location for that particular beam. In such embodiments, it may be the case (e.g. in block 221 of method 18 (FIG. 4B)) that multiple ray lines from multiple voxels impinge on a single beamlet. In such cases, the block 223 intensity value adjustment to the beamlet may be some form of average or interpolation of the intensity value adjustments that would be applied by each of the individual voxels.

One technique for rapid estimation of achievable dose described above involves convolving a two-dimensional intensity distribution $i(x,y)$ and the two-dimensional dose estimate kernel $k(x,y)$ and then projecting the convolved intensity values of the resultant two-dimensional convolved intensity distribution $f(x,y)$ along corresponding ray lines by adding the convolved intensity values as dose contributions to voxels intersected by the ray lines. In some embodiments, it may be desirable to compute convolved intensity distributions $f_1(x,y)$, $f_2(x,y)$, ... for a number of different dose estimate kernels $k_1(x,y)$, $k_2(x,y)$, ..., where the different dose estimate kernels can be used to model different tissue densities and their corresponding different scattering patterns. Then, when estimating achievable dose for a particular voxel (e.g. when adding convolved intensity values as dose contributions to the particular voxel), the tissue density of the particular voxel p can be used to select convolved intensity values from a convolved intensity distribution $f_p(x,y)$ computed using a dose estimate kernel $k_p(x,y)$ which corresponds to the tissue density.

In the foregoing description, the invention has been described with reference to specific exemplary embodiments thereof. It will, however, be evident that various modifications and changes may be made thereto without departing from the broader spirit and scope of the invention. The description and drawings are, accordingly, to be regarded in an illustrative sense rather than a restrictive sense. While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for permitting manipulation of an achievable dose distribution estimate deliverable by a radiation delivery apparatus for proposed treatment of a subject, the achievable dose distribution estimate defined over a three-dimensional range of voxels with a dose value for each voxel, the method comprising:
   (a) determining a dose modification voxel for which it is desired to modify the dose value and determining a corresponding magnitude of desired dose modification;
   (b) receiving the achievable dose distribution estimate, the dose modification voxel and the corresponding magnitude of desired dose modification as input to a processor;
   (c) for each of a plurality of beams:
      (i) characterizing, using the processor, each beam as a two-dimensional array of beamlets, wherein each beamlet is associated with a corresponding intensity value and a ray line representing a projection of the beamlet into space; and
      (ii) identifying, using the processor, one or more dose-change beamlets which have associated ray lines that intersect the dose modification voxel;
   (d) modifying, using the processor, the intensity values of the one or more identified dose-change beamlets based on the magnitude of desired dose modification, wherein modifying the intensity values of the one or more identified dose-change beamlets comprises, for each of the one or more identified dose-change beamlets, modifying the intensity value of each identified dose-change beamlet by a corresponding amount, the corresponding amount based on the magnitude of the desired dose modification;
   (e) updating, using the processor, the achievable dose distribution estimate to account for the modified intensity values of the identified dose-change beamlets; and
   (f) outputting, from the processor, the updated achievable dose distribution estimate.

2. A method according to claim 1 wherein determining the dose modification voxel comprises:
   receiving, as input to the processor, a requested modification to a dose quality metric; and using the requested modification to the dose quality metric to determine, using the processor, the dose modification voxel.

3. A method according to claim 2 wherein using the requested modification to the dose quality metric to determine, using the processor, the dose modification voxel comprises solving an inverted dose quality metric function that expresses coordinates and magnitudes of dose in terms of values of the dose quality metric.

4. A method according to claim 2 wherein the dose quality metric comprises a DVH curve associated with a tissue structure in the subject and wherein using the requested modification to the dose quality metric to determine, using the processor, the dose modification voxel comprises identifying a voxel in the tissue structure of the subject to be the dose modification voxel.

5. A method according to claim 4 wherein identifying the voxel in the tissue structure of the subject to be the dose modification voxel comprises identifying all of the voxels in the tissue structure of the subject to be dose modification voxels and performing steps (b), (c) and (d) for each of the dose modification voxels.

6. A method according to claim 4 wherein identifying the voxel in the tissue structure of the subject to be the dose modification voxel comprises:
receiving image data for the subject, the image data comprising an image of the tissue structure; and
associating particular voxels with the tissue structure based on the image data.

7. A method according to claim 2 wherein the dose quality metric comprises a DVH curve and wherein using the requested modification to the dose quality metric to determine, using the processor, the dose modification voxel comprises:
identifying a location of the requested modification on the DVH curve to have a dose value D_selected; and
identifying a voxel in the achievable dose distribution estimate having a dose value in a range D_selected±Δ to be the dose modification voxel, where Δ is a range parameter.

8. A method according to claim 7 wherein using the requested modification to the dose quality metric to determine, using the processor, the dose modification voxel comprises: unsuccessfully attempting to identify the voxel in the achievable dose distribution estimate having the dose value in the range D_selected±Δ and, increasing the range parameter Δ and repeating the attempt to identify the voxel with the increased range parameter Δ.

9. A method according to claim 7 wherein identifying the voxel in the achievable dose distribution estimate having the dose value in the range D_selected±Δ to be the dose modification voxel comprises identifying a plurality of candidate dose modification voxels having dose values in the range D_selected±Δ.

10. A method according to claim 9 wherein the plurality of candidate dose modification voxels comprise a number of candidate dose modification voxels that is greater than a threshold number $V_{max}$, and the method comprises decreasing the range parameter Δ and repeating the attempt to identify the voxel in the achievable dose distribution estimate having the dose value in the range D_selected±Δ to be the dose modification voxel with the decreased range parameter Δ.

11. A method according to claim 1 comprising determining, using the processor, one or more secondary dose modification voxels and corresponding magnitudes of desired dose modification for the one or more secondary dose modification voxels and treating secondary dose modification values as dose modification voxels when performing steps (b), (c) and (d).

12. A method according to claim 11 wherein determining, using the processor, the one or more secondary dose modification voxels comprises determining the one or more secondary dose modification voxels to be in a marginal region proximate to the dose modification voxel.

13. A method according to claim 11 wherein the corresponding magnitudes of desired dose modification for the one or more secondary dose modification voxels are less than the magnitude of the desired dose modification for the dose modification voxel.

14. A method according to claim 1 wherein determining the magnitude of the desired dose modification comprises determining the magnitude to be one or more of: a fraction f (0≤f≤1) of the dose value for the dose modification voxel; a fraction f (0≤f≤1) of a maximum dose restriction for a tissue structure at the location of the dose modification voxel; a fraction f (0≤f≤1) of a prescription dose amount for a target tissue structure at the location of the dose modification voxel; an amount proportional to movement of a computer pointing device; an amount input by an operator; an operator-configurable fixed amount; a fixed amount that is a parameter of a system on which the method is performed.

15. A method according to claim 1 wherein modifying, using the processor, the intensity values of the one or more of the dose-change beamlets comprises determining magnitudes of intensity value changes for the one or more dose-change beamlets according to a function that is dependent on the magnitude of desired dose modification and the number of the one or more dose-change beamlets, and wherein the function is proportional to the magnitude of desired dose modification and inversely proportional to the number of the one or more dose-change beamlets.

16. A method according claim 1 wherein modifying, using the processor, the intensity values of one or more of the dose-change beamlets comprises subjecting proposed intensity value modifications to one or more intensity restrictions.

17. A method according to claim 16 wherein the one or more intensity restrictions comprise one or more of: the intensity values of the one or more dose-change beamlets must be greater than a minimum threshold; the intensity values of the one or more dose-change beamlets must be less than a maximum threshold; a spatial variation between the intensity values of the one or more dose-change beamlets and the intensity values of one or more neighboring beamlets must be less than a maximum variation threshold.

18. A method according to claim 1 comprising, for each of the plurality of beams and for each of the one or more dose-change beamlets, determining, using the processor, one or more secondary dose-change beamlets and treating the one or more secondary dose-change beamlets as dose-change beamlets when performing steps (c) and (d).

19. A method according to claim 18 wherein, for each of the plurality of beams and for each of the one or more dose-change beamlets, determining, using the processor, one or more secondary dose-change beamlets comprises determining the one or more secondary dose-change beamlets to be in a marginal region proximate to each of the one or more dose-change beamlets.

20. A method according to claim 19 wherein modifying the intensity values of one or more of the dose-change beamlets comprises, for each of the one or more dose-change beamlets, modifying the intensity values of the secondary dose-change beamlets in the marginal region proximate to each of the one or more dose-change beamlets by magnitudes less than a magnitude of the change to each of the one or more dose-change beamlets.

21. A method according to claim 1 wherein updating, using the processor, the achievable dose distribution estimate comprises using a dose estimation technique to determine dose contributions attributable to the modified intensity values of the one or more dose-change beamlets, the dose estimation technique comprising one or more of: Monte Carlo, collapsed cone convolution, pencil beam, anisotropic analytical algorithm and Boltzman equation solvers.

22. A method according to claim 1 wherein updating, using the processor, the achievable dose distribution estimate comprises, for each of the plurality of beams comprising one or more dose change beamlets:
 convolving the intensity values of the two-dimensional array of beamlets with a two-dimensional dose estimate kernel to obtain a two-dimensional convolved intensity distribution, the two-dimensional convolved intensity distribution comprising a convolved intensity value for each beamlet; and
 for each beamlet in the two-dimensional array of beamlets: identifying voxels that are intersected by the ray line associated with the beamlet; and adding a dose contribution to the intersected voxels, the added dose contribution based on the convolved intensity value of the beamlet.

23. A method according to claim 22 wherein the dose estimate kernel comprises a two-dimensional point spread function.

24. A method according to claim 22 wherein the dose estimate kernel comprises a linear combination of two dimensional point spread functions.

25. A method according to claim 22 wherein convolving the intensity values of the two-dimensional array of beamlets with the two-dimensional dose estimate kernel comprises: multiplying a Fourier transform of the intensity values of the two-dimensional array of beamlets with a Fourier transform of the two-dimensional dose estimate kernel to obtain a Fourier multiplication result; and determining an inverse Fourier transform of the Fourier multiplication result to obtain the two-dimensional convolved intensity distribution.

26. A method according to claim 22 wherein, when a plurality of ray lines from a single beam intersect a particular voxel, adding the dose contribution to the particular voxel comprises adding the dose contribution based on a linear combination of the convolved intensity values of the plurality of beamlets corresponding to the plurality of ray lines.

27. A method according to claim 22 wherein, for each beamlet in the two-dimensional array of beamlets and for each intersected voxel, the added dose contribution is based on the convolved intensity value of the beamlet multiplied by an attenuation factor, the attenuation factor decreasing with a depth of the intersected voxel within the subject.

28. A method according to claim 1 wherein updating, using the processor, the achievable dose distribution estimate comprises, for each of the plurality of beams comprising one or more dose-change beamlets:
 convolving the intensity values of the two-dimensional array of beamlets with a plurality of two-dimensional dose estimate kernels to obtain a corresponding plurality of two-dimensional convolved intensity distributions, each two-dimensional convolved intensity distribution comprising a convolved intensity value for each beamlet, wherein each dose estimate kernel is associated with a different range of tissue densities; and
 for each beamlet in the two-dimensional array of beamlets: identifying voxels that are intersected by the ray line associated with the beamlet; and adding a dose contribution to the intersected voxels, the dose contribution for any one intersected voxel based on the convolved intensity value of the beamlet from one of the plurality of two-dimensional convolved intensity distributions, the one of the plurality of two-dimensional convolved intensity distributions selected based on tissue density of the one intersected voxel.

29. A method according to claim 1 comprising scaling the updated achievable dose distribution estimate such that the updated achievable dose distribution estimate more closely approximates the magnitude of desired dose modification corresponding to the dose modification voxel.

30. A method according to claim 1 comprising subjecting the updated achievable dose distribution to one or more dose restrictions.

31. A method according to claim 30 wherein the one or more dose restrictions comprise one or more of: the updated achievable dose distribution must not reduce dose in voxels corresponding to target tissue structures in the subject below a minimum target structure threshold; and the updated achievable dose distribution must not increase dose in voxels corresponding to healthy tissue structures in the subject above a maximum healthy structure threshold.

32. A method according to claim 30 wherein, subjecting the updated achievable dose distribution to one or more dose restrictions concludes that there is a violation of a dose restriction, and after concluding that there is a violation of a dose restriction, the method comprises addressing the violation of the dose restriction, wherein addressing the violation of the dose restriction comprises one or more of: rejecting the update to the achievable dose distribution estimate; and adjusting the magnitude of the desired dose modification corresponding to the dose modification voxel and repeating steps (b), (c) and (d) with the adjusted magnitude.

33. A method according to claim 30 wherein, subjecting the updated achievable dose distribution to one or more dose restrictions concludes that there is a violation of a dose restriction, and the method comprises:
 addressing the violation of the dose restriction, wherein addressing the violation of the dose restriction comprises: determining one or more restriction violating voxels which cause the updated dose distribution to violate the dose restriction and one or more corresponding desired dose change magnitudes; repeating steps (b), (c) and (d) with the one or more restriction violating voxels and the one or more corresponding desired dose change magnitudes in place of the dose modification voxel and the corresponding magnitude of the desired dose modification; re-subjecting the updated achievable dose distribution to the one or more dose restrictions; and
 repeating addressing the violation of the dose restriction until subjecting the updated achievable dose distribution to one or more dose restrictions concludes that there is not a violation of any dose restriction.

34. A method according to claim 1 comprising, after updating, using the processor, the achievable dose distribution estimate, determining, using the processor, one or more updated dose quality metrics using the updated achievable dose distribution estimate.

35. A method according to claim 34 wherein determining one or more updated dose quality metrics comprises subjecting at least one updated dose quality metric to one or more dose quality metric restrictions.

36. A method according to claim 35 wherein the one or more dose quality metric restrictions comprise one or more of: the at least one updated dose quality metric must have a minimum percentage volume of a target structure with dose above a minimum target structure threshold; and the at least one updated dose quality metric must have a minimum percentage volume of a healthy tissue structure with dose lower than a maximum healthy tissue structure threshold.

37. A method according to claim 1 further comprising, for each of the plurality of beams,
  initializing, using the processor, the intensity values of the beamlets in the two-dimensional array of beamlets, wherein initializing the intensity values of the beamlets in the two-dimensional array of beamlets comprises one or more of: setting all intensity values to zero;
  setting intensity values according to a random process;
  setting intensity values such that an approximate sphere of dose encompasses target tissue structures;
  setting intensity values for the beamlets having ray lines that intersect target structures to be a first positive value and setting intensity values for beamlets having raylines that do not intersect the target structures to have a lower value;
  setting intensity values such that a resultant dose distribution estimate has a maximum dose higher than a threshold; and
  setting intensity values for all or a subset of the beamlets having raylines based on a function of a prescription dose for a target structure.

38. A method according to claim 1 comprising, after updating, using the processor, the achievable dose distribution estimate, determining, using the processor, one or more radiation delivery parameters based on the updated achievable dose estimate, the one or more radiation delivery parameters suitable for use by the radiation delivery apparatus for treatment of the subject.

39. A method according to claim 38 wherein determining, using the processor, one or more radiation delivery parameters based on the updated achievable dose estimate comprises performing an iterative optimization process.

40. A method according to claim 39 wherein performing the iterative optimization process comprises optimizing the one or more radiation delivery parameters which will provide an optimized dose distribution estimate within an acceptable range to the updated achievable dose estimate.

41. A computer program product carrying instructions embodied in a non-transitory computer-readable medium, the instructions when executed by a suitable processor cause the processor to perform a method for permitting manipulation of an achievable dose distribution estimate deliverable by a radiation delivery apparatus for proposed treatment of a subject, the achievable dose distribution estimate defined over a three-dimensional range of voxels with a dose value for each voxel, the method comprising: the method of claim 1.

42. A method for permitting manipulation of an achievable dose distribution estimate deliverable by a radiation delivery apparatus for proposed treatment of a subject, the achievable dose distribution estimate defined over a three-dimensional range of voxels with a dose value for each voxel, the method comprising:
  (a) determining a dose modification voxel for which it is desired to modify the dose value and determining a corresponding magnitude of desired dose modification;
  (b) receiving the achievable dose distribution estimate, the dose modification voxel and the corresponding magnitude of desired dose modification as input to a processor;
  (c) for each of a plurality of beams:
    (i) characterizing, using the processor, each beam as a two-dimensional array of beamlets, wherein each beamlet is associated with a corresponding intensity value and a ray line representing a projection of the beamlet into space; and
    (ii) identifying, using the processor, one or more dose-change beamlets which have associated ray lines that intersect the dose modification voxel;
  (d) modifying, using the processor, the intensity values of the one or more identified dose-change beamlets based on the magnitude of desired dose modification, wherein modifying the intensity values of the one or more identified dose-change beamlets comprises, for each of the one or more identified dose-change beamlets, modifying the intensity value of each identified dose-change beamlet by a corresponding amount, the corresponding amount based on the magnitude of the desired dose modification; and
  (e) updating, using the processor, the achievable dose distribution estimate to account for the modified intensity values of the one or more identified dose-change beamlets and, after updating, using the processor, the achievable dose distribution estimate, determining, using the processor, one or more radiation delivery parameters based on the updated achievable dose estimate, the one or more radiation delivery parameters suitable for use by the radiation delivery apparatus for treatment of the subject;
  (f) outputting, from the processor, the updated achievable dose distribution estimate and the one or more radiation delivery parameters;
  wherein determining, using the processor, one or more radiation delivery parameters based on the updated achievable dose estimate comprises performing an iterative optimization process;
  wherein performing the iterative optimization process comprises estimating an optimized dose distribution over a three-dimensional range of voxels resulting from an optimization beam having a spatially varying two-dimensional optimization intensity distribution characterized by a two-dimensional array of optimization beamlets wherein each optimization beamlet is associated with a corresponding optimization intensity value, the estimating comprising:
    associating an optimization ray line with each optimization beamlet, the optimization ray line representing a projection of the optimization beamlet into space;
    convolving the two-dimensional optimization intensity distribution with a two-dimensional optimization dose estimate kernel to obtain a two-dimensional optimization convolved intensity distribution, the two-dimensional optimization convolved intensity distribution comprising an optimization convolved intensity value for each optimization beamlet; and
    for each optimization beamlet in the two-dimensional array of optimization beamlets: identifying voxels in the three- dimensional range of voxels that are intersected by the optimization ray line associated with the optimization beamlet; and adding an optimization dose contribution to the intersected voxels, the added optimization dose contribution based on the optimization convolved intensity value of the optimization beamlet.

43. A system for permitting manipulation of an achievable dose distribution estimate deliverable by a radiation delivery apparatus for proposed treatment of a subject, the achievable dose distribution estimate defined over a three-dimensional range of voxels with a dose value for each voxel, the system comprising a computer-based controller connectable to control a radiation delivery apparatus, the controller configured to:
  determine a dose modification voxel for which it is desired to modify the dose value and a corresponding magnitude of desired dose modification;

for each of a plurality of beams:
characterize each beam as a two-dimensional array of beamlets, wherein each beamlet is associated with a corresponding intensity value and a ray line representing a projection of the beamlet into space; and
identify one or more dose-change beamlets which have associated ray lines that intersect the dose modification voxel;
modify the intensity values of the one or more identified dose-change beamlets based on the magnitude of the desired dose modification, wherein the controller is configured to modify the intensity values of the one or more identified dose change beamlets by, for each of the one or more identified dose-change beamlets, modifying the intensity value of each identified dose-change beamlet by a corresponding amount, the corresponding amount based on the magnitude of the desired dose modification;
update the achievable dose distribution estimate to account for the modified intensity values of the identified dose-change beamlets.

44. A system according to claim 43 wherein the controller is configured to receive, as input, a requested modification to a dose quality metric; and to use the requested modification to the dose quality metric to determine the dose modification voxel; wherein the dose quality metric comprises a DVH curve associated with a tissue structure in the subject; and wherein the controller is configured to use the requested modification to the dose quality metric to determine the dose modification voxel by identifying a voxel in the tissue structure of the subject to be the dose modification voxel.

45. A system according to claim 43 wherein the controller is configured to receive, as input, a requested modification to a dose quality metric; and to use the requested modification to the dose quality metric to determine the dose modification voxel; wherein the dose quality metric comprises a DVH curve; and wherein the controller is configured to use the requested modification to the dose quality metric to determine the dose modification voxel by:
identifying a location of the requested modification on the DVH curve to have a dose value D_selected; and
identifying a voxel in the achievable dose distribution estimate having a dose value in a range D_selected±Δ to be the dose modification voxel, where Δ is a range parameter.

46. A system according to claim 43 wherein the controller is configured to subject the updated achievable dose distribution to one or more dose restrictions.

47. A system according to claim 43 wherein the controller is configured, after updating the achievable dose distribution estimate, to determine one or more updated dose quality metrics using the updated achievable dose distribution estimate.

48. A system according to claim 43 wherein the controller is configured comprising, after updating the achievable dose distribution estimate, to determine one or more radiation delivery parameters based on the updated achievable dose estimate, the one or more radiation delivery parameters suitable for use by the radiation delivery apparatus for treatment of the subject.

49. A system according to claim 43 wherein the controller is configured to determine one or more radiation delivery parameters based on the updated achievable dose estimate by performing an iterative optimization process and the controller is configured to perform by estimating an optimized dose distribution over a three-dimensional range of voxels resulting from an optimization beam having a spatially varying two-dimensional optimization intensity distribution characterized by a two-dimensional array of optimization beamlets wherein each optimization beamlet is associated with a corresponding optimization intensity value, and the controller is configured to estimate the the optimized dose distribution by:
associating an optimization ray line with each optimization beamlet, the optimization ray line representing a projection of the optimization beamlet into space;
convolving the two-dimensional optimization intensity distribution with a two-dimensional optimization dose estimate kernel to obtain a two-dimensional optimization convolved intensity distribution, the two-dimensional optimization convolved intensity distribution comprising an optimization convolved intensity value for each optimization beamlet; and
for each optimization beamlet in the two-dimensional array of optimization beamlets: identifying voxels in the three-dimensional range of voxels that are intersected by the optimization ray line associated with the optimization beamlet; and adding an optimization dose contribution to the intersected voxels, the added optimization dose contribution based on the optimization convolved intensity value of the optimization beamlet.

* * * * *